US012030052B2

(12) United States Patent
Pawell et al.

(10) Patent No.: US 12,030,052 B2
(45) Date of Patent: Jul. 9, 2024

(54) MICROFLUIDIC DELIVERY METHOD UTILIZING AN ELECTRIC FIELD

(71) Applicant: Indee. Pty. Ltd., Sydney (AU)

(72) Inventors: Ryan Pawell, San Francisco, CA (US); Amy Twite, Berkeley, CA (US); Geoff Facer, Redwood City, CA (US); Katherine Lau, Alameda, CA (US); Adrian Lievano, San Francisco, CA (US); Julyana Acevedo, Berkeley, CA (US)

( * ) Notice: Subject to any disclaimer, the term of this patent is extended or adjusted under 35 U.S.C. 154(b) by 434 days.

(21) Appl. No.: 17/367,619

(22) Filed: Jul. 5, 2021

(65) Prior Publication Data

US 2021/0339252 A1    Nov. 4, 2021

Related U.S. Application Data

(62) Division of application No. 16/474,996, filed as application No. PCT/AU2018/051190 on Nov. 2, 2018, now Pat. No. 11,052,394.

(60) Provisional application No. 62/580,922, filed on Nov. 2, 2017.

(51) Int. Cl.
| | |
|---|---|
| *B01L 3/00* | (2006.01) |
| *A61K 35/15* | (2015.01) |
| *A61K 35/17* | (2015.01) |
| *C12N 13/00* | (2006.01) |
| *C12N 15/64* | (2006.01) |
| *C12N 15/87* | (2006.01) |
| *C12N 15/90* | (2006.01) |

(52) U.S. Cl.
CPC ........ *B01L 3/502761* (2013.01); *A61K 35/15* (2013.01); *A61K 35/17* (2013.01); *B01L 3/502715* (2013.01); *B01L 3/502746* (2013.01); *C12N 13/00* (2013.01); *C12N 15/64* (2013.01); *C12N 15/87* (2013.01); *C12N 15/90* (2013.01); *B01L 2200/0647* (2013.01); *B01L 2400/0415* (2013.01); *B01L 2400/082* (2013.01)

(58) Field of Classification Search
None
See application file for complete search history.

(56) References Cited

U.S. PATENT DOCUMENTS

| | | | |
|---|---|---|---|
| 8,293,524 | B2 | 10/2012 | Ionescu-Zanetti et al. |
| 10,510,716 | B2 | 12/2019 | Pawell |
| 11,052,394 | B2 * | 7/2021 | Pawell .................. C12N 15/87 |
| 11,465,147 | B2 * | 10/2022 | Pawell ............. B01L 3/502715 |
| 2012/0064518 | A1 | 3/2012 | Diefenback |

FOREIGN PATENT DOCUMENTS

| | | |
|---|---|---|
| JP | 2004248653 | 9/2004 |
| JP | 2016526923 | 8/2016 |
| WO | WO2012106536 A2 | 8/2012 |
| WO | WO2016077761 A1 | 5/2016 |
| WO | WO2016109864 A1 | 7/2016 |
| WO | WO20168492 A1 | 10/2016 |
| WO | WO2017041050 A1 | 3/2017 |

OTHER PUBLICATIONS

Wanderley, et al. (2011) "A Three-Dimensional Numerical Simulation of the Free Surface Flow Around a Ship Hull", In book: Computational Simulations and Applications, By ResearchGate, Editor Jianping Zhu, London, UK, pp. 395-408. (Year: 2011).*
Zhao, et. al. (2016) "A flow-through cell electroporation device for rapidly and efficiently transfecting massive amounts of cells in vitro and ex vivo", Nature Scientific Rim, 6: article 18469, DOI:10.1038/srep 18469, 9 pages.
Chu, et al. (2009) "Conversion of MDCK cell line to suspension culture by transfecting human siat7e gene and its application for influenza virus production" Proceedings of the National Academy of Science, USA, 106(35): 14802-07, (Year: 2009).
Joergensen, et al. (2011) "Efficiency of Cellular Delivery of Antisense Peptide Nucleic Acid by Electroporation Depends on Change and Electroporation Geometry", Oligonucleotides, 21(1): 29-37. (Year: 2011).

* cited by examiner

*Primary Examiner* — Robert M Kelly
(74) *Attorney, Agent, or Firm* — Todd Martin

(57) ABSTRACT

A method and device for transfecting a cell to introduce an exogenous material into the cell. The method includes exposing the cell to a region of unsteady flow in the presence of an electric field to encourage introduction of the exogenous material into a cell without lysing the cell.

11 Claims, 27 Drawing Sheets

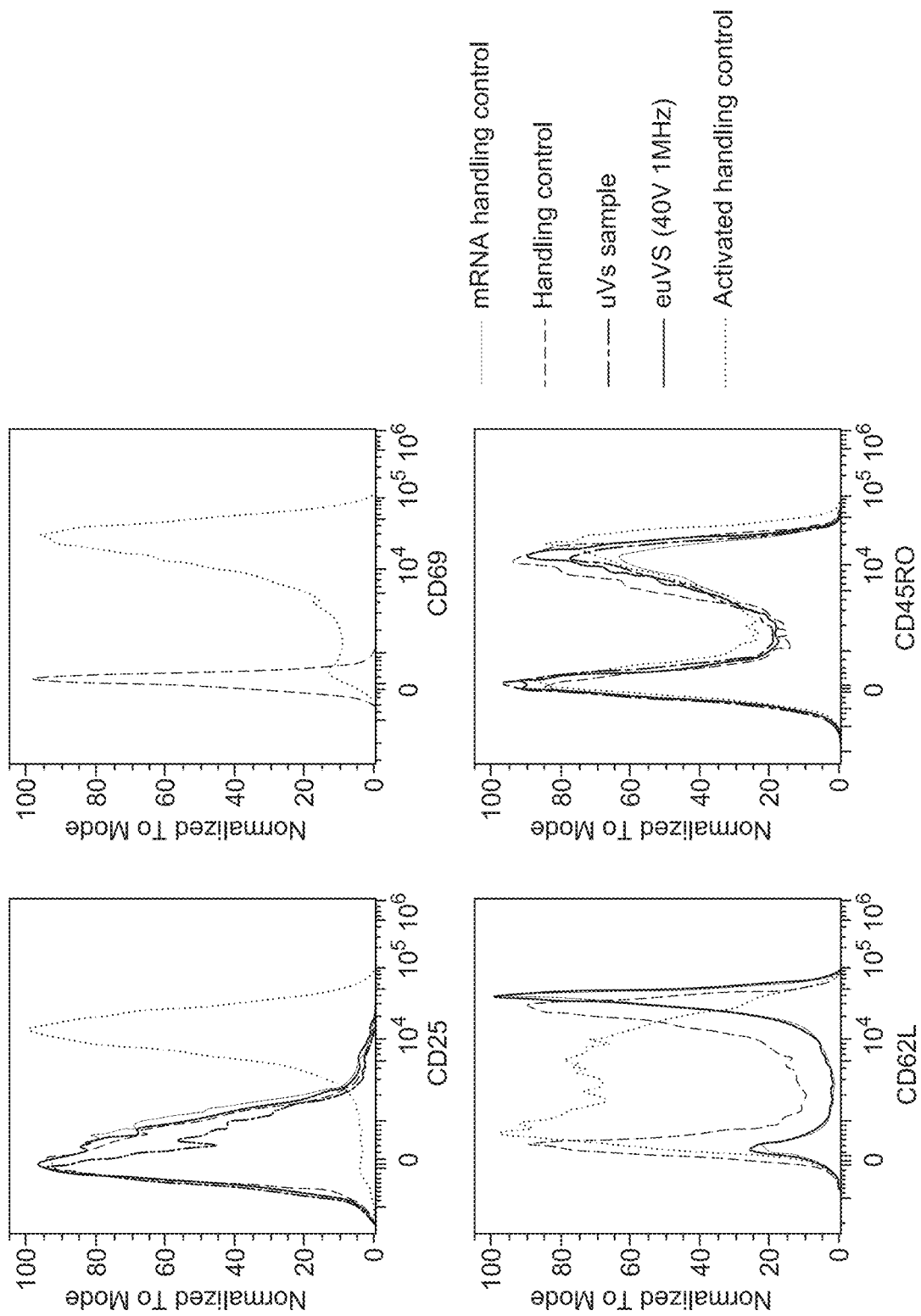

| CD4+ | Live | CD3+ | CD3+CD4+ | CD3+CD4+Tcm | CD3+CD4 +Teff-RA+-RO+- | CD3+CD4 CD3+CD4+Tem | CD45RO | CD45RA CD3+CD4+Tn |
|---|---|---|---|---|---|---|---|---|
| 0V.fcs | 91.7% | 91.0% | 68.6% | 3.38% | 3.09% | 55.8% | | 37.7% |
| eUVs 40v-1.fcs | 89.2% | 91.5% | 68.4% | 3.84% | 3.52% | 56.9% | | 35.7% |
| eUVs 40v-2.fcs | 88.8% | 91.6% | 68.9% | 3.63% | 3.17% | 57.6% | | 35.6% |
| eUVS 60.fcs | 74.4% | 89.6% | 66.2% | 2.64% | 1.86% | 70.2% | | 25.3% |
| eUVs 80v-1.fcs | 82.2% | 92.4% | 69.9% | 2.10% | 0.73% | 73.8% | | 23.3% |
| eUVs 80v-2.fcs | 79.9% | 92.1% | 71.1% | 2.59% | 1.05% | 70.6% | | 25.8% |
| eUVS100.fcs | 67.3% | 90.8% | 67.2% | 2.39% | 1.19% | 71.6% | | 24.8% |
| eUVs 120v-1.fcs | 76.8% | 91.7% | 70.6% | 1.25% | 0.47% | 75.2% | | 23.1% |
| eUVs 120v-2.fcs | 50.3% | 89.3% | 65.0% | 2.52% | 1.13% | 73.7% | | 22.7% |
| MRNA1.fcs | 92.9% | 89.3% | 64.7% | 3.63% | 3.99% | 51.2% | | 41.2% |
| MRNA2.fcs | 94.5% | 89.5% | 64.3% | 3.73% | 4.40% | 50.6% | | 41.3% |
| 0718 Handling control.fcs | 89.1% | 86.0% | 62.6% | 3.67% | 1.90% | 66.6% | | 27.8% |
| ACT handling control.fcs | 88.3% | 84.7% | 65.6% | 48.8% | 46.0% | 2.21% | | 2.93% |

| CD8+ | Live | CD3+ | CD3+CD8a+ | CD3+CD8a+Tcm | CD3+CD8a+ Tem-RA | CD45RA CD3+CD8a+Tn | CD45RO CD3+CD8a+Tem |
|---|---|---|---|---|---|---|---|
| 0V.fcs | 91.7% | 91.0% | 22.4% | 18.8% | 4.07% | 54.6% | 22.5% |
| eUVs 40v-1.fcs | 89.2% | 91.5% | 22.8% | 20.5% | 4.67% | 50.3% | 24.6% |
| eUVs 40v-2.fcs | 88.8% | 91.6% | 22.4% | 19.9% | 5.25% | 50.8% | 24.1% |
| eUVS 60.fcs | 74.4% | 89.6% | 19.3% | 23.8% | 6.69% | 33.9% | 35.6% |
| eUVs 80v-1.fcs | 82.2% | 92.4% | 14.8% | 24.0% | 11.3% | 19.5% | 45.2% |
| eUVs 80v-2.fcs | 79.9% | 92.1% | 15.6% | 21.5% | 11.2% | 28.3% | 39.0% |
| eUVS100.fcs | 67.3% | 90.8% | 15.0% | 18.2% | 8.90% | 35.5% | 37.4% |
| eUVs 120v-1.fcs | 76.8% | 91.7% | 11.5% | 19.2% | 13.1% | 21.2% | 46.4% |
| eUVs 120v-2.fcs | 50.3% | 89.3% | 15.3% | 18.5% | 7.93% | 38.8% | 34.7% |
| MRNA1.fcs | 92.9% | 89.3% | 27.2% | 16.4% | 3.93% | 61.7% | 17.9% |
| MRNA2.fcs | 94.5% | 89.5% | 27.5% | 17.4% | 3.83% | 60.7% | 18.0% |
| 0718 Handling control.fcs | 89.1% | 86.0% | 23.2% | 13.1% | 7.43% | 45.3% | 34.1% |
| ACT handling control.fcs | 88.3% | 84.7% | 24.4% | 20.8% | 11.2% | 47.2% | 20.7% |

Figure 15A

| CD4+ | | | | | |
|---|---|---|---|---|---|
|  | Live | CD3+ | CD3+CD4+ | CD3+CD4+ Tn-1 | CD3+CD4+ Tcm-1 |
| uVS 0V-1.fcs | 88.4 % | 86.1 % | 78.4 % | 39.7 % | 41.4 % |
| uVS 0V-2.fcs | 88.6 % | 84.6 % | 77.0 % | 38.3 % | 40.7 % |
| euVS 40V no off-1.fcs | 87.6 % | 85.7 % | 77.5 % | 33.8 % | 45.3 % |
| euVS 40V no off-2.fcs | 87.6 % | 84.1 % | 77.4 % | 33.6 % | 43.7 % |
| euVS 40V 10 off-1.fcs | 84.1 % | 83.5 % | 77.5 % | 31.3 % | 45.1 % |
| euVS 40V 10 off-2.fcs | 83.8 % | 82.0 % | 76.5 % | 29.4 % | 44.7 % |
| euVS 40V 20 off-1.fcs | 84.4 % | 83.4 % | 77.7 % | 27.9 % | 45.1 % |
| euVS 40V 20 off-2.fcs | 84.7 % | 82.8 % | 76.4 % | 35.1 % | 42.1 % |
| euVS 40V 30 off-1.fcs | 88.5 % | 84.3 % | 78.9 % | 39.4 % | 40.5 % |
| euVS 40V 30 off-2.fcs | 55.3 % | 73.4 % | 72.7 % | 15.7 % | 43.0 % |
| handling control.fcs | 87.6 % | 80.7 % | 77.2 % | 36.4 % | 27.3 % |
| mRNA1.fcs | 90.0 % | 84.6 % | 77.6 % | 23.8 % | 50.0 % |
| mRNA2.fcs | 91.2 % | 85.7 % | 77.0 % | 22.0 % | 42.0 % |
| Activated handling control.fcs | 85.9 % | 83.8 % | 69.4 % | 18.5 % | 38.9 % |
|  |  |  |  |  |  |
| CD8+ |  |  |  |  |  |
|  | Live | CD3+ | CD3+CD8a+ | CD3+CD8a+Tcm | CD3+CD8a+Tem-RA |
| uVS 0V-1.fcs | 88.40% | 86.10% | 13.10% | 17.20% | 7.96% |
| uVS 0V-2.fcs | 88.60% | 84.60% | 14.00% | 17.40% | 7.30% |
| euVS 40V no off-1.fcs | 87.60% | 85.70% | 13.80% | 18.00% | 8.19% |
| euVS 40V no off-2.fcs | 87.60% | 84.10% | 13.70% | 18.00% | 7.56% |
| euVS 40V 10 off-1.fcs | 84.10% | 83.50% | 13.90% | 17.00% | 7.74% |
| euVS 40V 10 off-2.fcs | 83.80% | 82.00% | 14.30% | 18.00% | 8.46% |
| euVS 40V 20 off-1.fcs | 84.40% | 83.40% | 13.60% | 16.80% | 8.82% |
| euVS 40V 20 off-2.fcs | 84.70% | 82.80% | 13.80% | 16.70% | 8.94% |
| euVS 40V 30 off-1.fcs | 88.50% | 84.30% | 13.00% | 16.50% | 7.42% |
| euVS 40V 30 off-2.fcs | 55.30% | 73.40% | 15.70% | 9.21% | 15.80% |
| handling control.fcs | 87.60% | 80.70% | 14.60% | 16.70% | 7.70% |
| mRNA1.fcs | 90.00% | 84.60% | 14.60% | 15.40% | 6.21% |
| mRNA2.fcs | 91.20% | 85.70% | 15.10% | 16.60% | 7.65% |
| Activated handling control.fcs | 85.90% | 83.80% | 13.90% | 6.21% | 40.10% |

Figure 17A

| CD3+CD4+ Tem-RA-1 | CD3+CD4+Tem-1 | CD3+CD4+ CD25+ | CD3+CD4+ CD69+ | CD3+CD4 +CD137+ | CD3+CD4+ GFP+ |
|---|---|---|---|---|---|
| 2.27 % | 16.6 % | 7.71 % | 1.49 % | 0.14 % | 28.8 % |
| 2.23 % | 18.7 % | 7.15 % | 1.76 % | 0.26 % | 29.8 % |
| 1.95 % | 19.0 % | 5.99 % | 1.40 % | 0.11 % | 37.9 % |
| 2.22 % | 20.6 % | 7.43 % | 1.75 % | 0.18 % | 36.4 % |
| 2.27 % | 21.3 % | 6.27 % | 1.30 % | 0.13 % | 41.5 % |
| 2.14 % | 23.8 % | 6.29 % | 1.66 % | 0.16 % | 42.6 % |
| 2.29 % | 24.7 % | 5.71 % | 1.56 % | 0.17 % | 44.2 % |
| 1.67 % | 21.2 % | 5.35 % | 1.67 % | 0.12 % | 43.4 % |
| 2.18 % | 17.9 % | 8.20 % | 1.73 % | 0.13 % | 33.7 % |
| 3.26 % | 38.1 % | 5.87 % | 2.84 % | 0.28 % | 73.9 % |
| 27.3 % | 9.09 % | 11.3 % | 3.52 % | 0.69 % | 0.22 % |
| 9.52 % | 16.7 % | 8.04 % | 1.58 % | 0.23 % | 0.28 % |
| 4.00 % | 32.0 % | 7.52 % | 1.24 % | 0.11 % | 0.33 % |
| 5.56 % | 37.0 % | 92.0 % | 98.1 % | 38.8 % | 0.95 % |
| | | | | | |
| CD3+CD8a +Tn | CD3+CD8a +Tem | CD3+CD8a +CD25+ | CD3+CD8a +CD69+ | CD3+CD8a +CD137+ | CD3+CD8a +GFP+ |
| 30.60% | 44.20% | 2.96% | 9.73% | 0.92% | 31.10% |
| 30.20% | 45.10% | 3.73% | 11.60% | 1.43% | 31.60% |
| 25.70% | 48.10% | 3.35% | 10.60% | 0.56% | 38.70% |
| 25.00% | 49.40% | 3.15% | 11.20% | 0.57% | 36.20% |
| 22.60% | 52.70% | 2.39% | 9.51% | 0.17% | 42.40% |
| 22.10% | 51.50% | 2.96% | 10.40% | 0.48% | 42.10% |
| 20.00% | 54.30% | 2.77% | 10.80% | 0.60% | 46.10% |
| 22.20% | 52.20% | 2.45% | 11.10% | 0.59% | 41.50% |
| 30.90% | 45.10% | 3.73% | 9.84% | 0.89% | 34.10% |
| 10.10% | 64.90% | 1.75% | 12.30% | 0% | 70.60% |
| 37.40% | 38.20% | 6.57% | 14.60% | 2.93% | 0.53% |
| 38.40% | 39.90% | 3.37% | 11.00% | 0.76% | 0.44% |
| 38.40% | 37.30% | 2.70% | 8.17% | 0.61% | 0.81% |
| 20.10% | 33.60% | 66.90% | 96.20% | 79.90% | 3.68% |

Figure 17B

| CD4+ | | | | | | |
|---|---|---|---|---|---|---|
| | Live | CD3+ | CD4+ | CCR7+ | CD25 | CD62L |
| 40V no off set 1MHz - 2 | 83.5 % | 63.7 % | 80.3 % | 93.4 % | 90.8 % | 69.4 % |
| 40V no off set 1MHz | 79.6 % | 67.0 % | 79.5 % | 94.6 % | 90.5 % | 73.9 % |
| 40V 10 off set parallel and series 1MHz - 2 | 78.0 % | 63.6 % | 80.7 % | 93.4 % | 90.1 % | 72.3 % |
| 40V 10 off set parallel and series 1MHz | 80.3 % | 63.8 % | 80.0 % | 94.4 % | 90.7 % | 72.6 % |
| 40V 10 off set 1MHz - 2 | 84.0 % | 63.1 % | 79.5 % | 93.5 % | 90.4 % | 69.8 % |
| 40V 10 off set 1MHz | 81.7 % | 64.0 % | 79.7 % | 94.5 % | 90.5 % | 73.0 % |
| 40V 10 off set 100KHz - 2 | 79.0 % | 60.9 % | 79.1 % | 93.0 % | 89.4 % | 68.5 % |
| 40V 10 off set 100KHz | 78.4 % | 61.0 % | 78.7 % | 93.6 % | 90.8 % | 71.1 % |
| 40V 10 off set 500KHz - 2 | 78.7 % | 55.4 % | 77.5 % | 91.8 % | 88.4 % | 63.3 % |
| 40V 10 off set 500KHz | 82.2 % | 63.4 % | 79.7 % | 94.1 % | 90.8 % | 71.9 % |
| Handling control | 85.2 % | 71.9 % | 81.0 % | 96.7 % | 89.6 % | 74.9 % |
| mRNA Ctrl 1 | 87.7 % | 73.5 % | 81.8 % | 96.2 % | 91.1 % | 77.7 % |
| mRNA Ctrl 2 | 84.7 % | 70.5 % | 81.4 % | 96.4 % | 90.3 % | 72.6 % |
| Handling control activated | 80.5 % | 24.9 % | 81.8 % | 81.3 % | 96.0 % | 51.4 % |
| | | | | | | |
| CD8+ | | | | | | |
| | Live | CD3+ | CD8a+ | CCR7+ | CD25+ | CD62L+ |
| 40V no off set 1MHz - 2 | 83.50% | 63.70% | 13.30% | 64.20% | 78.20% | 42.80% |
| 40V no off set 1MHz | 79.60% | 67.00% | 14.00% | 64.40% | 78.80% | 44.70% |
| 40V 10 off set parallel and series 1MHz - 2 | 78.00% | 63.60% | 12.90% | 63.70% | 79.50% | 45.40% |
| 40V 10 off set parallel and series 1MHz | 80.30% | 63.80% | 13.60% | 65.10% | 79.10% | 46.10% |
| 40V 10 off set 1MHz - 2 | 84.00% | 63.10% | 13.60% | 60.90% | 78.90% | 41.40% |
| 40V 10 off set 1MHz | 81.70% | 64.00% | 13.60% | 65.40% | 81.70% | 44.60% |
| 40V 10 off set 100KHz - 2 | 79.00% | 60.90% | 13.50% | 60.70% | 77.80% | 40.30% |
| 40V 10 off set 100KHz | 78.40% | 61.00% | 14.20% | 65.70% | 79.80% | 43.10% |
| 40V 10 off set 500KHz - 2 | 78.70% | 55.40% | 14.40% | 58.60% | 77.40% | 34.00% |
| 40V 10 off set 500KHz | 82.20% | 63.40% | 13.80% | 64.20% | 81.00% | 43.20% |
| Handling control | 85.20% | 71.90% | 13.30% | 75.30% | 84.00% | 60.20% |
| mRNA Ctrl 1 | 87.70% | 73.50% | 13.30% | 75.20% | 82.80% | 60.90% |
| mRNA Ctrl 2 | 84.70% | 70.50% | 12.60% | 71.80% | 79.90% | 57.00% |
| Handling control activated | 80.50% | 24.90% | 8.85% | 62.70% | 94.20% | 37.70% |

Figure 21A

| CD69+ | Tn CD45RA+, CD62L+ | Tcm CD45RO+, CD62L+ | GFP+ |
|---|---|---|---|
| 46.8 % | 30.3 % | 58.0 % | 47.9 % |
| 39.9 % | 32.3 % | 62.5 % | 46.2 % |
| 47.3 % | 31.3 % | 60.0 % | 46.4 % |
| 44.1 % | 32.4 % | 61.3 % | 45.2 % |
| 46.5 % | 30.7 % | 58.4 % | 45.5 % |
| 41.8 % | 32.3 % | 61.5 % | 51.7 % |
| 48.5 % | 28.5 % | 56.6 % | 51.6 % |
| 43.5 % | 29.9 % | 60.6 % | 51.6 % |
| 50.1 % | 24.7 % | 52.4 % | 48.9 % |
| 43.4 % | 30.1 % | 60.7 % | 51.9 % |
| 39.0 % | 37.7 % | 63.6 % | 0.073 % |
| 42.2 % | 40.2 % | 62.1 % | 0.26 % |
| 41.9 % | 36.2 % | 58.6 % | 0.41 % |
| 78.0 % | 26.7 % | 47.1 % | 0.045 % |

A

| CD69+ | Tn CD45RA+, CD62L+ | Tcm CD45RO+, CD62L+ | GFP+ |
|---|---|---|---|
| 53.20% | 35.30% | 23.40% | 42.70% |
| 48.00% | 38.60% | 25.10% | 39.90% |
| 53.70% | 39.20% | 20.20% | 39.40% |
| 49.90% | 37.40% | 24.00% | 39.80% |
| 54.90% | 33.70% | 24.40% | 37.10% |
| 52.90% | 35.00% | 25.50% | 45.00% |
| 57.00% | 32.00% | 21.50% | 43.30% |
| 52.20% | 35.90% | 23.30% | 46.80% |
| 55.90% | 26.40% | 18.30% | 43.00% |
| 50.50% | 35.50% | 22.60% | 45.40% |
| 40.10% | 52.50% | 27.40% | 0.60% |
| 40.90% | 54.80% | 24.40% | 1.31% |
| 46.00% | 50.10% | 22.80% | 1.33% |
| 69.40% | 37.10% | 29.20% | 2.69% |

Figure 21B

MICROFLUIDIC DELIVERY METHOD UTILIZING AN ELECTRIC FIELD

FIELD OF THE INVENTION

This present disclosure relates to a method for introducing exogenous material into a cell subjected to unsteady flow, including exposing the cell to an electric field, in the presence of the exogenous material.

BACKGROUND OF THE INVENTION

Biomicrofluidics may be used to separate or enrich (Shields et al. 2015), modify, culture, and qualify cells. Thus, biomicrofluidics lends itself to gene-modified cell therapy (GMCT) development and manufacturing where cells need to be separated or enriched, modified, cultured, and qualified. GMCTs based on modified T cells can provide substantially improved outcomes for patients with some hematological malignancies. Specifically, chimeric-antigen-receptor-T-cell (CAR-T) therapies targeting CD19 have demonstrated remarkable responses and possibly cures in patients with advanced acute lymphoblastic leukemia unresponsive to all prior therapies. Gene-modified CAR-T cells are the first cellular therapy to gain FDA (Food & Drug Administration) approval for treatment of cancer following demonstration of an 83% remission rate in acute lymphoblastic leukemia.

CAR-T cells are generated via genetic modification of human T cells that results in the modified human T cells displaying an extracellular single-chain variable fragment directed to a tumor target linked to a hinge region, on or more co-stimulatory domain(s), and an intracellular CD3-zeta activating domain. The manufacture of these therapies is costly, time consuming with relatively low throughput, and can have variable results depending on the cell type being modified. In addition, the most problematic step in GMCT manufacturing is the intracellular delivery of nucleic acids via transfection or transduction for expression of the CAR on the T cell surface. Viral transduction (such as retroviruses and lentiviruses) is the main method currently being used to generate CAR-T therapies for clinical trials. However these methods require significant amounts of hands on time during production and require extensive intra- and post-production safety testing to avoid infusion of replication competent viruses at the time of therapy administration.

Physical transfection methods, such as electroporation, are appealing alternatives for GMCT manufacturing. Electroporation does not require extensive safety or release precautions and can be used to deliver a broader range of exogenous materials into cells (e.g., DNA, RNA, proteins and/or various complexes), but can result in significant cell losses or alteration of normal cell function. Many alternative physical delivery methods are in development to address these issues. In general, microfluidic methods are shown to improve upon macroscale methods due to more uniform processing conditions—cell diameters and microfluidic channel geometries are on the same order of magnitude. Examples of physical microfluidic intracellular delivery methods include flow through electroporation, micro-needle injection, cell squeezing, fluid shear, along with electrosonic jet ejection. Though these methods offer promising and appealing alternatives to current GMCT production, they are limited by throughput, processing speeds, clogging, and/or cumbersome translation from a research platform to clinical production. It is further noted that conventional mechanoporation systems and methods typically require laminar or static flow conditions after mechanoporation.

The ideal intracellular delivery platforms for generation of GMCTs like CAR-T therapies should be flexible across different exogenous materials (e.g., DNA, RNA, protein and/or various complexes) and applicable to a variety of cell types with minimal perturbation of cell viability, recovery, and normal cell activity. Currently, T cells are being modified with a range of exogenous materials including plasmids, RNAs, and Cas9 ribonucleoprotein complexes (RNPs) for generation of GMCTs. RNA is of particular interest as it offers significant utility with a range of modification modalities after intracellular delivery to T cells. This includes exogenous materials to edit the genome of various T cells in a permanent, long lived and transient manner to express chimeric antigen receptors (CARs).

There are several practical metrics when considering microfluidic and physical intracellular delivery for GMCT development and manufacturing, including: (1) cell recovery, (2) cell viability, (3) delivery or expression efficiency, (4) throughput, and (5) maintenance of normal or desired cell state and function. Low cell recovery rates are not ideal due to the large number of cells required for GMCTs. High cell viability is also preferred as cells are frequently expanded after modification. Observationally, low cell viability or the presence of dead cells is known to reduce cell growth rates or halt growth completely. Additionally, non-viable cells can induce adverse immune response and regulators require justification for allowing administration of cell therapies with low cell viability at the time of infusion due to their potential for inducing infusional toxicity. Delivery efficiency should be sufficient to induce a therapeutic effect without altering the cell state and efficiency of cell modification needs to be sufficiently high to avoid the need for extra processing steps like dead cell removal. Electroporation has been used to transfect naïve T cells with CARs and found recovery rates to be less than 20% after 24 hours. In addition to greatly reducing viability, electroporation increased expression of T cell surface activation markers, which is undesirable as it can reduce therapeutic efficacy. Total throughput is important as is the rate at which cells can be processed—it is unlikely that single cell micro-needle injection will be useful for GMCT manufacturing if modifying $10^8$ cells prior to expansion requires at least $10^8$ seconds or approximately 3 years. Cumulatively, none of the microfluidic and physical intracellular delivery methods described above meet or exceed all the needs of GMCT development and manufacturing.

An advance in the field of microfluidic transfection is disclosed in PCT Publication No. WO 2016/109864 to Pawell, the entire description of which is incorporated by reference herein.

SUMMARY OF THE INVENTION

The present disclosure is broadly directed to methods and devices for intracellular delivery by use of fluid forces and electric fields. The present disclosure is further broadly directed to methods and devices of intracellular delivery by use of fluid forces and electrophoresis. The present disclosure also broadly relates to methods and devices of actively delivering a payload, cargo, or exogenous material via electrophoresis to a cell permeabilised by a fluid force.

In a broad form, the present disclosure relates to a method of introducing exogenous material into a cell by exposing the cell to an electric field and unsteady flow. In another broad form, the present disclosure relates to a method of improving introduction of an exogenous material into a cell by exposing the cell to an electric field and unsteady flow.

In a first aspect, there is provided a method of introducing an exogenous material into a cell, the method including exposing the cell, or the portion thereof, to: (i) at least one region of an unsteady flow; and (ii) an electric field, to thereby introduce the exogenous material into the cell.

In a second aspect, there is provided a method of improving introduction of an exogenous material into a cell, the method including exposing the cell to: (i) at least one region of an unsteady flow; and (ii) an electric field, to thereby improve introduction of the exogenous material to the cell.

In a third aspect, there is provided a device introducing an exogenous material a cell, or a portion thereof, the device including: an at least partially enclosed channel with dimensions configured to allow a flow of the cell and the exogenous material suspended in a liquid therethrough, wherein the channel is configured to include at least one region of unsteady flow; and a source or an emitter of an electric field.

Preferably, the device is a microfluidic device.

Suitably, at least a portion of the electric field is configured to introduce, deliver, or drive the exogenous material into a cell by electrophoresis. Preferably, the portion of the electric field has a strength sufficient to introduce, drive or deliver the exogenous material into the cell. In preferred embodiments, the electric field is an electrophoretic field. In certain embodiments, the entire electric field may be configured to introduce or deliver the exogenous material into a cell by electrophoresis.

Suitably, exposing includes exposure in the presence of the exogenous material.

In preferred embodiments, the exogenous material is driven through a perturbation in the outer membrane of the cell. Suitably, the perturbation may be substantially produced by unsteady flow. The perturbation may be at least one pore in a cell membrane or wall.

Preferably, the electric field is generated using an alternating current or a direct current, or a combination thereof. Suitably, the source or emitter is configured to generate an electric field using an alternating current or a direct current, or a combination thereof.

Suitably, the electric field is generated by one or more electrodes. Preferably, the, or each, electrode is a platinum electrode. Preferably, the, or each, electrode may be an anode or a cathode.

The, or each, electrode may include a material adapted to minimize degradation of the, or each, electrode when the electric field is applied. In preferred embodiments, the material may be a conductive material. Suitably, the conductive material may be platinum.

Suitably, the, or each, electrode may include one or more layers of the material adapted to minimize degradation of the, or each, electrode when the electric field is applied.

Preferably, the, or each, electrode may include one or more surfaces including the material adapted to minimize degradation of the, or each, electrode when the electric field is applied.

Suitable, the, or each, electrode may be adapted to enhance adhesion to a substrate.

Preferably, the electric field may be generated by a plurality of electrodes in an interdigitated array.

Suitably, the cell may be exposed to the electric field within at least a partially enclosed channel configured to allow a flow of the exogenous material. The channel may be configured to include the at least one region of unsteady flow, and more preferably, a plurality of regions of unsteady flow.

Preferably, the channel may include one or more flow diverters. Suitably, the at least one region of unsteady flow is downstream of the, or each, flow diverter.

In certain preferred embodiments, the cell that is exposed to at least one region of unsteady flow may also be exposed to a transient decrease in pressure. Suitably, the cell may be subjected to a transient decrease in pressure within the at least one region of unsteady flow. Preferably, the transient decrease in pressure is downstream of the, or each, flow diverter.

Suitably, the, or each, flow diverter is an obstacle, preferably a post.

Preferably, the cell is, or includes, a prokaryotic cell, an eukaryotic cell, an archae, a fungal cell, a plant cell or an insect cell, and any combination thereof. Suitably, the eukaryotic cell may be a mammalian cell or a yeast cell.

Suitably, the exogenous material is, or includes, one or more agents selected from the group including a small organic molecule, a nucleic acid, a plasmid, a microbial chromosome, a ribozyme, a DNAzyme, a ribosome, a nucleotide, a single stranded oligonucleotide, a double stranded oligonucleotide, a synthetic oligonucleotide, a virus-like particle, an enzyme, a plastid, a protein, an assembly containing multiple proteins (hetero or homo oligomers/tertiary structure), an aptamer, a DARPin (Designed Ankyrin Repeat Protein), a dendrimer, a linear synthetic polymer, a branched synthetic polymer, a peptide, a peptoid, an amino acid, a lipid, a carbohydrate, a polysaccharide, a charged synthetic polymer, an uncharged synthetic polymer, a liposome, a liposome with embedded protein, single walled unilamellar vesicle, a multiwalled unilamellar vesicle, a virus-like particle, a virus, a quantum dot, a carbon nanotube, a radionuclide, a metabolite, a magnetic bead, an inorganic nanoparticle, an organic nanoparticle, a magnetic nanoparticle, viral capsid, a metal particle (e.g., a gold particle), a monosaccharide, a cytokine, a chemokine, a drug molecule, a pharmaceutically relevant molecule(s), an organelle, a vitamin, and a steroid, and any combination thereof. Preferably, the exogenous material is, or includes, a nucleic acid. More preferably, the nucleic acid is a DNA and/or an RNA. Even more preferably, the RNA is an mRNA.

In a fourth aspect, there is provided a device according to the third aspect when used according to a method of any one of the aforementioned aspects.

In a fifth aspect, there is provided a cell produced according to a method of any one of the aforementioned aspects.

In a sixth aspect, there is provided a cell suspension including a cell of the fifth aspect.

In a seventh aspect, there is provided a pharmaceutical composition including a cell according to the fifth aspect, or a cell suspension according to the sixth aspect, and a pharmaceutically acceptable diluent, carrier or excipient.

In an eighth aspect, there is provided a kit including a device according to any one of the aforementioned aspects.

In a further aspect, there is provided a method for transfecting a cell to introduce an exogenous material into the cell. The method includes introducing a liquid including the cell and the exogenous material into a flow channel of a microfluidic device, the flow channel including at least one flow diverter; exposing the cell to an unsteady flow downstream of the at least one flow diverter when the cell flows past the at least one flow diverter to temporarily permeabilise a membrane of the cell without the cell becoming lysed; and exposing the cell to an electrical field to introduce the exogenous material into the cell while the membrane is permeabilized.

In an additional aspect, there is provided a method for introducing exogenous material into a cell. The method includes exposing the cell in suspension with the exogenous material to a pressure change under unsteady flow conditions to temporarily permeabilise a cell membrane without the cell becoming lysed; and exposing the cell to an electrical field to introduce the exogenous material into the cell while the membrane is permeabilised.

The electric field may be an electrophoretic field. The method may further include configuring the exogenous material with a charge. The exogenous material may be negatively charged, positively charged, or neutral. The electric field is at an electric field strength that facilitates delivery of the exogenous material while also being insufficient to adversely perturb the cell state.

In a further additional aspect, there is provided a microfluidic device for introducing exogenous material into a cell. The device includes a substrate including at least one flow channel, said flow channel having opposed sidewalls, a width from one of said sidewalls to the other of said sidewalls, and a length perpendicular to the width. The device also includes a plurality of flow diverters oriented in an array along the width of said flow channel, said flow diverters being oriented within said flow channel to cause an unsteady flow along a downstream portion of the length of the flow channel to temporarily permeabilise a membrane of the cell. The device also includes at least one electrode positioned downstream of said flow diverters, said at least one electrode being configured to emit an electric field to facilitate introduction of the exogenous material into the cell while the membrane is permeabilized.

In yet a further aspect, there is provided a modified cell containing exogenous material introduced into the cell by the process of inducing a pressure change under unsteady flow conditions to temporarily permeabilise a cell membrane without the cell becoming lysed; and generating an electrical field to introduce the exogenous material into the cell while the membrane is permeabilised.

In an additional aspect, there is provided a pharmaceutical composition including a cell modified by temporarily permeabilising a cell membrane and introducing an exogenous material into the cell while the cell is within an electric field and pulsed by an unsteady flow; and a pharmaceutically acceptable carrier.

It will be appreciated that reference herein to "preferred" or "preferably" is intended as exemplary only.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The articles "a" and "an" are used herein to refer to one or to more than one (i.e., to at least one) of the grammatical object of the article. By way of example, "an element" means one element or more than one element. As used herein, the use of the singular includes the plural (and vice versa) unless specifically stated otherwise.

By "about" is meant a quantity, level, value, number, frequency, percentage, dimension, size, amount, weight or length that varies by as much about 15, 14, 13, 12, 11, 10, 9, 8, 7, 6, 5, 4, 3, 2 or 1% to a reference quantity, level, value, number, frequency, percentage, dimension, size, amount, weight or length.

Unless the meaning is clearly to the contrary, all ranges set forth herein are deemed inclusive of the endpoints. Ranges are to be interpreted as being fully inclusive of all values between the limits.

Unless defined otherwise, all technical and scientific terms used herein have the same meaning as commonly understood by those of ordinary skill in the art to which the present disclosure belongs. Although any methods and materials similar or equivalent to those described herein can be used in the practice or testing of the present disclosure, preferred methods and materials are described.

BRIEF DESCRIPTION OF THE DRAWINGS

FIGS. 14A and 14B are graphical representations of representative histograms showing surface marker expression of µVS and eµVS processed samples of resting PBMCs at 48 hours after processing.

FIGS. 15A and 15B are representations of expression profiles of various activation or T cell lineage surface markers in CD3+ cells divided into CD4+ and CD8+ populations in resting PBMCs processed using µVS or eµVS at 48 hours.

FIGS. 17A and 17B are representations of expression profiles of various activation or T cell lineage surface markers in CD3+ cells divided into CD4+ and CD8+ populations in resting PBMCs processed using eµVS at 24 hours after processing.

FIGS. 21A and 21B are representations of expression profiles of various activation or T cell lineage surface markers in CD3+ cells divided into CD4+ and CD8+ populations in overnight activated PBMCs processed using eµVS after 24 hours.

DETAILED DESCRIPTION OF THE INVENTION

Figure 1:
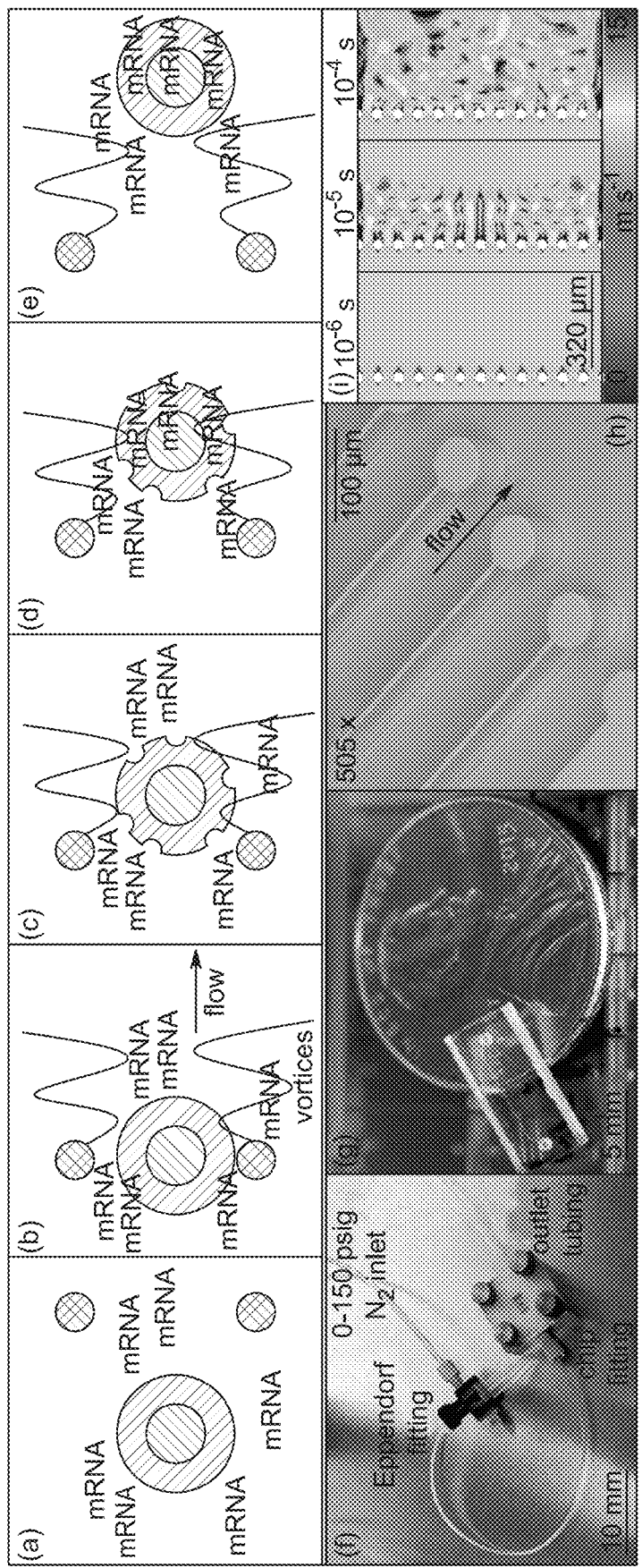
FIG. 1 is a schematic representation of a method for introducing exogenous material into a cell as herein disclosed.

Each embodiment described herein is to be applied mutatis mutandis to each and every embodiment unless specifically stated otherwise.

In a preferred aspect, the present disclosure relates to methods and devices for introducing exogenous material into a cell by exposing the cell to: (i) at least one region of unsteady flow; and (ii) an electric field. Without wishing to be bound by any particular theory, exposure of the cell to an electric field facilitates, drives, pushes, delivers, enhances, or otherwise transports the exogenous material into the cell. Suitably, the force and in particular, driving force, of the electric field enhances transport or translocation of the exogenous material into the cell, or one or more cellular and/or sub-cellular compartments such as, but not limited to, a nucleus or a mitochondrion. In certain preferred embodiments, the electric field is an electrophoretic field, and more preferably, a low-strength electrophoretic field.

Suitably, a low strength electric field may be sufficient to improve or facilitate uptake of extracellular material into cell(s) hydrodynamically porated with unsteady flow. A person of skill in the art will appreciate that the electric field strength for the intracellular delivery of an exogenous material to a cell, or a fraction thereof, may preferably be such that (1) uptake of the charged extracellular material is enhanced or promoted, preferably along with (2) expression, and if relevant, preferably (3) perturbation of the cell state is minimized, although without limitation thereto.

In the context of the present disclosure, introduction of an exogenous material into a target entity such as a cell by way of electroporation typically includes exposing the target entity to an electric field above a certain threshold. By way of example only, typical electric field strengths for electroporation are about 2 kV/cm to about 4 kV/cm for red blood cells, about 5 kV/cm to about 7 kV/cm for platelets and about 7 kV/cm to about 10 kV/cm for bacteria and yeast (non-limiting examples of which may be found in Crawford and Chronos, Semin Intery Cardiol. 1996 March; 1(1):91-102, which is incorporated by reference in its entirety).

Moreover, efficient or improved electroporation may include modulating, modifying, adjusting, or otherwise tuning the electric field. By way of example only, introducing inositol hexaphosphate (IHP) into red blood cells may be achieved using high voltage square pulses (e.g., about 2.13 kV/cm, about 2 ms) followed by lower voltage exponential pulses (e.g., about 1.5 to about 1.75 kV/cm, about 5 ms)—typically this leads to increased delivery of IHP to red blood cells of up to 50% when compared to the usual exponential pulse encapsulation (non-limiting examples of which may be found in U.S. Pat. No. 6,090,617, which is incorporated by reference in its entirety). Exponential pulses may be used for both electrophoretic delivery and electroporation. Moreover, in this case the exponential pulse may be well below the electroporation threshold, meaning, the efficient delivery may be attributed to electrophoresis caused by the low electric field strength exponential pulse and cell membrane.

The present disclosure broadly relates to methods and devices for electrohydrodynamic poration and delivery where membrane poration via unsteady fluid flow is coupled to electrophoretic delivery. The present disclosure also broadly relates to electrohydrodynamic delivery where an exogenous material is introduced into a cell by hydrodynamic poration of the cell using unsteady flow, and intracellular delivery of the exogenous material into the hydrodynamically porated cell is enhanced with exposure of the electric field. It is contemplated that suitably, an electric field as used in the methods and/or devices of the present disclosure is sufficient to improve intracellular introduction or delivery of an exogenous material to hydrodynamically porated cells, but not sufficient to adversely alter the cells, and in particular irreversibly modify or alter the cells.

In particular embodiments, the present disclosure may relate to a method of introducing an exogenous material into a cell, the method including the steps of exposing the cell to: (i) at least one region of an unsteady flow; and (ii) an electric field, to thereby introduce the exogenous material into the cell.

In other particular embodiments, the present disclosure may relate to a method of improving introduction of an exogenous material into a cell, the method including the steps of exposing the cell to (i) at least one region of an unsteady flow; and (ii) an electric field, to thereby improve introduction of the exogenous material to the cell.

In the context of "introducing an exogenous material into a cell" as recited herein, the term "introducing" means that the exogenous material is delivered into, travels into, translocates into, transfers into, or traverses at least the outermost barrier of a cell, i.e., into the cell wall or cell membrane. The exogenous material may travel beyond the outermost barrier of a cell, and pass through the cell wall or cell membrane to enter the cytoplasmic region of the cell. The exogenous material may travel into organelles or sub-cellular components within the cell. Specifically, the exogenous material may travel into the nucleus, or a mitochondrion, of the cell.

As used herein, the term "exogenous" means any material that exists outside of a cell prior to the cell being exposed to the methods described herein. It will be understood that the term "exogenous" relates to material that has been produced, generated, developed, grown, or originated outside the cell. Suitably, the step of exposing the cell includes exposing the cell in the presence of the exogenous material. The exogenous material may be naturally occurring or synthetic.

As used herein, the term "naturally occurring" (alternatively, "wild-type") insofar as it relates to a material means any material that exists in nature, and may include biologically active substances. The naturally occurring materials may be modified in ways that do not naturally occur in nature and are suitably isolated from nature.

In the context of the present disclosure, the term "synthetic" means not naturally occurring, but made through human technical intervention. In the context of synthetic proteins and nucleic acids, this encompasses molecules produced by recombinant, chemical synthetic, or combinatorial techniques. The synthetic material may be an imitation of a naturally occurring material, or may not be analogous to a material that exists in nature.

The exogenous material may be biologically active in the cell into which the material is introduced. Alternatively, the exogenous material may have no detectable effect on the cell after it is introduced.

Suitably, the exogenous material is, or may comprise, one or more agents. The term "agent" encompasses organic molecules, inorganic molecules, biological particles such as viruses (although without limitation thereto), small organic molecules, proteinaceous molecules such as peptides, polypeptides and proteins as well as compositions including them, nucleic acid molecules such as RNA, DNA, and mimetics and chemical analogs thereof. An "agent" may also be a combination of one or more different or heterogenous agents, by way of example an antibody labelled with a radionuclide, although without limitation thereto. The exogenous material may be a composition including one or more agents, in addition to a suitable carrier, buffer or excipient, or combinations of suitable carriers, buffers, and excipients. Non-limiting examples of a suitable carrier, buffer, or excipient include water, phosphate-buffered saline, a cell growth media, although without limitation thereto.

In particularly preferred embodiments, the exogenous material is, or may comprise, one or more agents selected from the group including a small organic molecule, a nucleic acid, a plasmid, a microbial chromosome, a ribozyme, a DNAzyme, a ribosome, a nucleotide, a single stranded oligonucleotide, a double stranded oligonucleotide, a synthetic oligonucleotide, a virus-like particle, an enzyme, a plastid, a protein, an assembly containing multiple proteins (hetero or homo oligomers/tertiary structure), an aptamer, a DARPin, a dendrimer, a linear synthetic polymer, a branched synthetic polymer, a peptide, a peptoid, an amino acid, a lipid, a carbohydrate, a polysaccharide, a charged synthetic polymer, an uncharged synthetic polymer, a liposome, a liposome with embedded protein, single walled unilamellar vesicle, a multiwalled unilamellar vesicle, a virus-like particle, a virus, a quantum dot, a carbon nanotube, a radionuclide, a metabolite, a magnetic bead, an inorganic nanoparticle, an organic nanoparticle, a magnetic nanoparticle, viral capsid, a metal particle (e.g., a gold particle), a monosaccharide, a cytokine, a chemokine, a drug molecule, a pharmaceutically relevant molecule(s), an organelle, a vitamin, and a steroid, and any combination thereof.

The, or each, agent, or exogenous material, may or may not be charged. A charge may be introduced to improve delivery using the methods of the present disclosure. In certain preferred embodiments, the exogenous material or the, or each, agent may be modified to increase a charge thereof. A modification may alter a net charge, or a relative charge. By way of example only, a proteinaceous molecule may be conjugated to a charged compound at a terminus or alternatively at an amino acid sidechain, to increase the net or relative charge of the proteinaceous molecule. In certain embodiments, the pH of a buffer or solution is adjusted to modify the charge of the exogenous material. In an alternative example, the charge of a polymer such as polyvinyl acetate, but not limited thereto, may altered, although without limitation thereto. Charge modification will be understood by a skilled addressee. The exogenous material may be positively charged. Alternatively, the exogenous material may be negatively charged. It is also contemplated that the exogenous material may be both positively and negatively charged. The exogenous material is preferably charged prior to introduction into the device. The pre-charging of the exogenous material may be performed, for example only, with negatively charged molecules, with positively charged molecules, or with the use of an electric field to enhance protons.

The exogenous material or agent may be isolated or purified. By "isolated," it is meant that material is substantially or essentially free from components that normally accompany it in its native state, or from components present during its production when purified or produced by synthetic means. Thus, the term "isolated" also includes within its scope purified or synthetic material.

As used herein, the term "purified" refers to material (e.g., a nucleic acid, peptide, or polypeptide) that is substantially free of cellular components or other contaminating material from the cell or tissue source from which the material is derived, or substantially free from chemical precursors or other chemicals when chemically synthesized. "Substantially free" means that a preparation of a material (e.g., a nucleic acid, peptide or polypeptide) is at least about 10%, 20%, 30%, 40%, 50%, 60%, 70%, 80%, 90%, 95%, 96%, 97%, 98%, 99% pure. In a preferred embodiment, the preparation of a material has less than about 40%, 30%, 20%, 10% and more suitably 5%, 4%, 3%, 2%, 1% (by dry weight), of non-material components or of chemical precursors or of non-material chemicals (also referred to herein as a "contaminating components"). When a material (e.g., a peptide or polypeptide is recombinantly produced, it is also suitably substantially free of culture medium, i.e., culture medium represents less than about 20%, 15%, 10%, 5%, 4%, 3%, 2%, 1% of the volume of the material preparation. The present disclosure may include isolated or purified preparations of at least about 0.001, 0.01, 0.1, 1.0, and 10 milligrams in dry weight.

In certain preferred embodiments, the exogenous material is, or may include a nucleic acid. Suitably, the nucleic acid is an isolated nucleic acid. The nucleic acid may be synthetic. The nucleic acid may be a chimeric molecule assembled, formed or otherwise synthesized from a plurality of different nucleic acids. The nucleic acid may be a peptide nucleic acid ("PNA") molecule, a deoxyribonucleic acid ("DNA") molecule, a locked nucleic acid, an unlocked nucleic acid, a phosphorothioate nucleic acid, an ribonucleic acid ("RNA") molecule, and any combination thereof. The RNA molecule may be a messenger RNA ("mRNA") molecule, a ribozyme, or an inhibitory RNA molecule. In particular embodiments that contemplate an inhibitor RNA molecule, the inhibitor RNA molecule may be microRNA ("miRNA") or a small (or short) interfering RNA ("siRNA").

The DNA molecule may be genomic DNA, cDNA, a naturally occurring chromosome or a portion thereof, a gene, a plasmid, a methylated DNA, an oligonucleotide, or an agent.

The term "gene" as used herein refers to any and all discrete coding regions of the cell's genome, as well as associated non-coding, and regulatory regions. The term is intended to mean the open reading frame encoding specific polypeptides, introns, and adjacent 5' and 3' non-coding nucleotide sequences involved in the regulation of expression. In this regard, the gene may further include control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, ribozymes, locked nucleic acids, unlocked nucleic acids, and the like. The exact size and/or strand of the molecule can vary depending on the particular application. An oligonucleotide is typically rather short in length, generally from about 10 to about 30 nucleotide residues, but the term can refer to molecules of any length, although the term "polynucleotide" or "nucleic acid" is typically used for large oligonucleotides.

The agent may be an agent for expressing a nucleic acid molecule. These exogenous materials generally include the nucleic acid molecule operably connected to a regulatory sequence, suitably for expression of a protein or a polypeptide of interest. In some embodiments, the agent further includes a sequence for transport of the protein to the cell surface or to the extracellular environment. The nucleic agent includes vectors such as viral or non-viral vectors, expression vectors and plasmids for expression in and secretion in a range of cells.

In particular embodiments, the agent is a vector and more preferably, an expression vector. An expression vector may be either self-replicating extra-chromosomal vector such as a plasmid, or a vector that integrates into a host genome. As used herein, the term "vector" refers to any molecule used as a vehicle to assist in the delivery or expression of a nucleic acid in a cell. Preferably, the vector expresses DNA, RNA, miRNA, siRNA or protein. By "vector," it is meant a polynucleotide molecule, suitably a DNA molecule derived, for example, from a plasmid, bacteriophage, a prokaryote, a fungus, virus, yeast or higher order eukaryote including plant, vertebrate or invertebrate animal, into which a polynucleotide can be inserted or cloned. A vector preferably contains one or more unique restriction sites and can be capable of autonomous replication in a defined host cell including a target cell or tissue or a progenitor cell or tissue thereof, or be integratable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can include a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In some embodiments, the vector is a viral or viral-derived vector, which is operably functional in vertebrate or invertebrate animal and suitably mammalian cells. Such vector may be derived from a poxvirus, a lentivirus, a retrovirus, an adenovirus or yeast. The vector can also include a selection marker such as an antibiotic resistance gene that can be used for selection of suitable transformants. Examples of such resistance genes are known to those of skill in the art and include the nptll gene that confers resistance to the antibiotics kanamycin and G418 (Geneticin®) and the hph gene, which confers resistance to the antibiotic hygromycin B.

In certain suitable embodiments, the present disclosure contemplates a agent encoding a chimeric antigen receptor (CAR), that preferably may be introduced or delivered to a T cell using methods and systems of the present disclosure. In some embodiments, the CAR is a fusion of an extracellular recognition domain (e.g., an antigen-binding domain), a transmembrane domain, and one or more intracellular signaling domains.

The present disclosure contemplates introduction of exogenous material for genome editing applications. According to these embodiments, the methods and devices of the present disclosure introduces one or more nucleases, and in particular engineered nucleases. Non-limiting examples of suitable nucleases include a meganuclease, a zinc finger nuclease (ZFNs), a transcription activator-like effector-based nuclease (TALEN), and the CRISPR-Cas9 system.

In other embodiments of the present disclosure, the vector is a viral vector, preferably a lentiviral vector or a retroviral vector. The vector may also be an artificial chromosome and preferably, a bacterial artificial chromosome or a yeast artificial chromosome. Alternatively, the vector may be a prokaryotic chromosome, and preferably may be a naturally-occurring prokaryotic chromosome. The naturally-occurring prokaryotic chromosome may be an isolated naturally-occurring prokaryotic chromosome.

The terms "polypeptide," "proteinaceous molecule," "peptide," and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations, and the like. Soluble forms of the subject proteinaceous molecules are particularly useful. Included within the definition are, for example, polypeptides containing one or more analogs of an amino acid including, for example, non-naturally occurring amino acids or polypeptides with substituted linkages. Also included are chimeric molecules including a plurality of amino acid sequences from different origins.

The present disclosure includes embodiments wherein at least a portion of the electric field is configured to deliver the exogenous material into a cell by electrophoresis. As would be understood by a skilled addressee, electrophoresis is the movement or motion of a molecule, and in particular a charged molecule, in an electric field.

Suitably, at least a portion of the electric field, and preferably where the electric field is an electrophoretic field, has a strength sufficient to drive the exogenous material into a cell. Preferably, the exogenous material is driven substantially through a perturbation of the cell, and more preferably through a perturbation of the cell caused by at least one region of unsteady flow. Even more preferably, the perturbation is caused by at least one region of unsteady flow and a transient decrease in pressure. Although not wishing to be bound by any particular theory, by subjecting a cell to fluid forces, and in particular unsteady flow, cells are susceptible to uptake of exogenous material, most likely through formation of pores or perturbations in the outer barrier of the cell. Preferably, this occurs without lysing the cell. The fluid forces, and in particular unsteady flow, may result in, produce or otherwise generate a transient decrease in pressure. The transient decrease in pressure may facilitate permeabilisation of the cell membrane without lysing the cell. A relatively sudden and temporary pressure drop across the cell membrane, whereby the intracellular pressure is greater than the extracellular pressure, may result in the temporary formation of pores in the membrane. In certain preferred embodiments, cell permeabilisation is not caused by passing the cell through a constriction to deform the cell, and thus cause pores or perturbations (so called "cell squeezing").

The present disclosure contemplates that in certain preferred embodiments, the electric field is generated using an alternating current ("AC"). In alternative embodiments, the electric field is generated using a direct current ("DC"). The AC may oscillate evenly, or may have oscillation such that there is a net direct for the force of the electric field. Asymmetric oscillation may be achieved by applying an alternating current to have a non-zero bias, although without limitation thereto. In other particular embodiments, the electric field may be generated by a combination of AC and DC. In those embodiments that contemplate a combination of AC and DC, the electric field may be generated by an AC current at incremental DC offsets, with or without DC current.

The present disclosure contemplates embodiments in which the cell is exposed to an electric field simultaneously to being exposed to at least one region of an unsteady flow. In alternative embodiments, these steps or treatments may occur sequentially, or step-wise. According to alternative embodiments that contemplate sequential or step-wise exposure or treatment, the cell may be exposed to at least one region of an unsteady flow prior to exposure to an electric field. Alternatively, the cell may be exposed to an electric field prior to exposure to at least one region of an unsteady flow.

It is contemplated that the present disclosure includes embodiments directed to methods which may include exposing a cell subjected to at least one region of an unsteady flow to an electric field.

The present disclosure further contemplates that the exposure to an electric field may occur in the same, or another compartment, flowcell or device to the subjecting the cell to unsteady flow, and preferably unsteady flow and a transient decrease in pressure.

In certain preferred embodiments, a cell is exposed to an electric field as the cell passes through a channel or device. The cell and the exogenous material may be contacted or mixed prior to exposure to the electric field. Alternatively, the cell may contact the exogenous material at the point of exposure to the electric field. It is also contemplated that in alternative embodiments, exposure to an electric field may occur when the cell and/or exogenous material is not in flow (i.e., is stationary, or temporarily stationary).

In particular embodiments of the present disclosure, the cell is a prokaryotic cell, a eukaryotic cell, a fungal cell, a gamete cell (e.g., a sperm cell or an ovum cell), a zygote, a protist cell, an archael cell, a plant cell or an insect cell. The eukaryotic cell may be a mammalian cell, or a yeast cell. It will be appreciated that the present disclosure also contemplates a progenitor cell and in particular a stem cell and more preferably, a hematopoetic stem cell or mesenchymal stem cell. The cell may be an immunogenic cell such as, but not limited to, a T cell or a B cell. The cell may be in culture, extracted from tissue samples and/or immortalized. It will be appreciated that in those embodiments that contemplate a plant cell, the cell wall may be completely or partially removed to form a protoplast, prior to treatment according to the methods of the present disclosure. The cell may be from a primary culture or may from a continuous (secondary) culture. The cell may be derived from any tissue type. The cell may or may not be terminally differentiated. Suitably, the cell may be an isolated cell.

It is contemplated that the cell may be a host cell. The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which includes a recombinant vector of the invention is a recombinant host cell.

As will be appreciated by a person of skill in the art, preferred starting cell densities may be dependent on the cell type and/or exogenous material. In preferred embodiments of the present disclosure and in particular preferred embodiments that relate to mammalian cells, the starting cell density is between about 10 thousand cells per mL to about 100 million cell per mL, and all integers in between.

The methods described herein may improve introduction of an exogenous material into a cell. By "improve", "improving" or "improvement", it is meant an enhancement, an enrichment, an increase or otherwise augmentation of one or more parameters or measures. This may be compared to methods employing one or a plurality of other physical, chemical or biological methods for introducing exogenous material into a cell. In certain preferred embodiments, the improvement of the methods of the present disclosure may be compared to methods for introducing exogenous material into a cell by exposing the cell at least one region of unsteady flow, optionally with a transient decrease in pressure. By way of example, an improvement may be an increase of substantially or about 1 to about 80%, about 1 to about 50%, about 1 to about 10%, or about 5, about 10, about 15, about 20, about 25, about 30, about 35, about 40, about 45, about 50, about 55, about 60, about 65, about 70, about 75 or about 80% or more of the, or each, parameter or measure, compared to a population of corresponding cells that are treated by a control, or comparator method (e.g., standard electroporation conditions, liposome-mediated transfection or a method subjecting cells to at least one region of unsteady flow only). The one or more parameters or measures may be qualitative or quantitative. The present disclosure contemplates an increase in an efficiency as measured by the number of cells that have, include or include the exogenous material. Alternatively, the number of molecules introduced into a cell may be measured. Cell survival or viability may be improved by using the methods described herein. The rate or number of pores introduced into a cell, or cell population, may be improved by the methods of the present disclosure. It will be appreciated that present disclosure contemplates an improvement may be measured by a combination of different parameters or measures. The improvement may be measure by any suitable technique or assay, as would be known by a skilled addressee. By way of example, a marker such as a green fluorescent protein (although without limitation thereto), may be used to measure or quantify the improvement. Alternatively, endogenous cellular markers may be used to monitor efficiency such as, but not limited to, one or more CD (cluster of differentiation) proteins.

The present disclosure contemplates that the strength of the electric field may vary. By way of example, the strength of the electric field may vary for different cell types and exogenous material for introduction into the cell. In certain preferred embodiments, the exposure time is between about 1 microsecond and about 1 second, and all integers therebetween.

Suitably, a strength generated by an electric field is sufficient to introduce the exogenous material into the cell. The voltage may be applied such that the strength or the pulse strength of the electric field may be in the range of about 0.001 volts per centimetre to about 100 kilovolt per centimetre ("kV/cm"). The strength or the pulse strength of the electric field may be in the range of about 0.01 kV/cm to about 1 kV/cm, about 0.05 kV/cm to about 0.5 kV/cm, about 0.1 kV/cm to about 0.3 kV/cm, and all integers therebetween.

The time that any one cell type can be exposed to the electric field will be determinable by the competent skilled addressee. Exposures that are too long may result in inefficiencies, while exposures that are too short may not allow for the introduction of the exogenous material into the cell. The optimum exposure times can be determined for a particular cell by reference to the examples of the present application.

Preferably, the cell is exposed to a transient decrease in pressure in the presence of the exogenous material for at least about 1 nanosecond, at least about 10 nanoseconds, at least about 100 nanoseconds, at least about 1 microsecond or at least about 1 millisecond. In certain embodiments of the present disclosure, the cell is exposed to a transient decrease in pressure for at least about 15 nanoseconds, at least about 20 nanoseconds, at least about 25 nanoseconds, at least about 30 nanoseconds, at least about 35 nanoseconds, at least about 40 nanoseconds, at least about 45 nanoseconds, at least about 50 nanoseconds, at least about 60 nanoseconds, at least about 70 nanoseconds, at least about 80 nanoseconds, at least about 90 nanoseconds, at least about 100 nanoseconds, at least about 150 nanoseconds, at least about 200 nanoseconds, at least about 250 nanoseconds, at least about 300 nanoseconds, at least about 350 nanoseconds, at least about 400 nanoseconds, at least about 450 nanoseconds, at least about 500 nanoseconds, at least about 550 nanoseconds, at least about 600 nanoseconds, at least about 650 nanoseconds, at least about 700 nanoseconds, at least about 750 nanoseconds, at least about 800 nanoseconds, at least about 850 nanoseconds at least about 900 nanoseconds, at least about 950 nanoseconds, at least about 1 microsecond, at least about 10 microseconds, at least about 50 microseconds, at least about 100 microseconds, at least about 200 microseconds, at least about 300 microseconds, at least about 400 microseconds, at least about 500 microseconds, at least about 600 microseconds, at least about 700 microseconds, at least about 800 microseconds, or at least about 900 microseconds, or more.

In certain embodiments, the strength or the pulse strength of the electric field is less than would be required to electroporate a cell. As would be understood, electroporation requires a sufficient strength to disrupt a cell membrane and result in a temporary increase in cell membrane permeability (e.g., by exceeding a threshold transmembrane voltage). By way of example, the strength or the pulse strength of the electric field may be about 50%, about 1% to about 50%, about 50% to about 99%, or about 1% to about 99% less than the strength necessary to adversely affect or significantly perturb the cell.

In certain preferred embodiments, the electric field used herein may be less than or equal to an intensity of a conventional electroporation technique. In other preferred embodiments, the electric field is an electrophoretic field. In the context of an electrophoretic field, it is meant that the electric field acts on a charged exogenous material thus causing the charged exogenous material to move. Suitably, the electric field is a strength of an electrophoretic field acts on a charged exogenous material thus causing the charged exogenous material to move. Preferably, the strength of an electrophoretic field is lower or less than the strength of an electroporative field or is lower of less than the strength required to significantly perturb the cell state. Preferably, the electrophoretic field strength is optimized based on cell type where the electrophoretic range perturbs the cells less than electroporation, or results in enhanced delivery of the agent relative to the electroporation without coupling.

Suitably, the electric field is generated by one or more electrodes. Suitably, the, or each, electrode includes a conductive medium. The, or each, electrode may be formed from a metal material, or a conductive polymer, or a combination thereof. The present disclosure contemplates that the, or each, electrode may be formed from the same or different materials. The metal material may be aluminium, gold, platinum, or any other suitable metal. In particular, metals which do not significantly degrade during operation may be preferred. Preferably, the metal used as in the surface layer of the electrode is platinum. Other metals or materials may be beneficial as adhesion layers between the surface metal and the substrate, such as, but not limited to, titanium, chromium, copper, silver, nickel, gold and indium. Also contemplated are combinations of a plurality of metals. Adhesion-promoting layers may also be compound materials such as silicon nitride, or elemental structures such as, but not limited to, graphene, tetrahedral amorphous carbon, amorphous silicon, or other compound materials. Non-limiting examples of suitable conductive polymers are poly (3,4-ethylenedioxythiophene), polynaphthalenes such as naphthalene-tetracarboxylic-dianhydride, polyanilines, or polyphenylenes including their sulphide-bearing derivatives. Non-limiting examples of conductive polymers may be found in Balint et al., Acta Biomaterialia, 2014. 10(6), 2341-2353, which is incorporated herein by reference in its entirety.

The present disclosure contemplates any suitable electrode pattern or configuration. In certain embodiments, the electrode pattern may be a plurality of electrode pairs configured into a first array of electrodes and a second array of electrodes. Accordingly, the first array of electrodes may be offset from the second array of electrodes. The present disclosure also contemplates an electrode pattern configured into an interdigitated (or comb-like) pattern.

As will be understood by a skilled addressee, this patterning may be achieved by any suitable means. In suitable embodiments, the electrodes may be integrated onto or into a quartz substrate, by (1) 100 nm amorphous silicon deposition to the DRIE quartz substrate; (2) 100 nm Platinum electrode deposition via sputter coating and lift off or e beam evaporation to the laser machined inlet-outlet substrate; and (3) anodic bonding of the lid and flow cell substrates. Other means of deposition include vapor deposition methods such as chemical vapor deposition and plasma enhanced chemical vapor deposition. Other means of patterning the electrodes include chemical etching, laser ablation, reactive ion etching, and focused ion beam patterning. Electrode patterns can also be achieved by pre-treating the substrate in the desired pattern, or its inverse, such that selective affinity of the conductive material is sufficient to produce the desired pattern during deposition.

Suitably, the, or each, electrode is arranged such that a uniform electric field is generated between electrodes. In one preferred embodiment, a ratio between electrode spacing and flow cell height generates a uniform electric field. Advantageously, the ratio between about 0.5 and about 5, more preferably is about 3, and more preferably about 3.1. In a preferred embodiment, interdigitated platinum electrode may span a microfluidic flow cell (flow-perpendicular) with an about 25-µm width (flow-wise) and an about 150-µm pitch resulting in an about 125-µm inter-electrode spacing. A wider range of ratios can also be employed, such as ratios between about 0.01 and about 100, with the consideration that uniformity may in some circumstances be reduced to capture benefits such as improved flow profiles. In more detail, one skilled in the art could determine the optimal ratio of electrode spacing to flow cell height that balances electric field uniformity with cell exposure time and flow profile to maximize delivery efficiency, cell viability and cell recovery.

The electrodes may be formed as part of the device, for example only, within the substrate, in a floor and/or ceiling portion of a flow channel, or surrounding the flow channel. The electrode may reside within a sidewall separating parallel flow channels. Alternatively, the electrodes may be a separate component of the system, and variably positioned along the length of the flow channel as desired. Where there is a second electrode, the electrodes may be arranged in a series and/or parallel relationship. The electrode is preferably configured to emit the electric field overlapping a zone of unsteady flow downstream of the flow diverter.

A power source, such as a voltage generator, DC generator, or AC generator, may be configured to energize the electrode. The power source may be configured with a means for adjusting an offset current. Such means may include a user interface.

Preferably, the cell exposed, or subjected to, at least one region of an unsteady flow, or alternatively, a plurality of regions of unsteady flow. The number of regions of unsteady flow may be suitably determined by a skilled address to suit particular needs, and may number 2, 3, 4, 5, 6, 7, 8, 9, 10, or more. A cell may be subjected to a plurality of regions of unsteady flow by movement throughout the channel. The region of unsteady flow, such as a localized region of unsteady flow, may have any suitable width. By way of example, a suitable width may be about 20 µm.

The present disclosure contemplates embodiments where the cell subjected to at least one region of unsteady flow is subjected to a transient change in pressure, and preferably a transient decrease in pressure. Although not wishing to be bound by any particular theory, in embodiments of the present disclosure wherein there is a localized region of unsteady flow substantially immediately downstream of a flow diverter, the cells may be exposed to a two-fold change in pressure as follows: (1) a localized increase in pressure caused by the unsteady flow; and (2) an increase in pressure following the transient decrease in pressure. This may create a pressure differential across the permeabilised cell membrane where the extracellular pressure is greater than the intracellular pressure and it may facilitate the active delivery of exogenous material near the cell membrane and/or exogenous material may be introduced into the cell by, for example, diffusion or flow from the local extracellular environment to the cytosol.

As used herein, the term "decrease in pressure" insofar as it relates to exposure of a cell to such a decrease means the cell is exposed to a zone of pressure that is relatively lower than the pressure immediately surrounding the zone. The pressure in the zone may be uniform or may have localized regions of varied pressure provided these localized regions still have a pressure that is lower relative to the pressure surrounding the zone. The pressure surrounding the zone may be uniform or may have localized regions of varied pressure provided these localized regions have a pressure that is higher relative to the zone. By "pressure" is meant the force per unit area exerted by a substance on its surroundings as is known in the art. The SI unit of pressure is the pascal (Pa). Other commonly used units for the measurement of pressure include kilopascals (kPa), pound forces/square inch (PSI), millimetres of mercury (mmHg), millibars (mbar), and atmospheres (atm) air pressure. Pressure specifically relating to a vacuum may be measured in torrs (Torr). In the present application when the term "kPa" is used, it refers to gauge pressure, not absolute pressure where a gauge pressure of 0 kPa refers to an absolute pressure of 101.325 kPa.

The transient decrease in pressure may be defined in the context of the pressure differential between a zone of lower pressure relative to the pressure of a surrounding zone. The transient decrease in pressure may also be defined in the context of the minimum pressure in the zone of lower pressure and the maximum pressure in the surrounding zones. For example, if the minimum pressure in the zone of lower pressure was about −10 kPa and the maximum pressure in the surrounding zone was about 100 kPa, then the pressure differential would be about 110 kPa. In another example, if the minimum pressure in the zone of lower pressure was about 20 kPa and the maximum pressure in the surrounding zone was about 500 kPa, then the pressure differential would be about 480 kPa. In a further example, the pressure differential between the zone of lower pressure and the surrounding zone may be about 200 kPa, which could be the result of the minimum pressure in the zone of lower pressure being in the range of about −100 kPa to about 1000 kPa and the maximum pressure in the surrounding zone being in the range of about 100 kPa to about 1200 kPa. In yet another example, the pressure differential between the zone of lower pressure and the surrounding zone may be about 50 kPa, which could be the result of the minimum pressure in the zone of lower pressure being in the range of about 0 kPa to about 150 kPa and the maximum pressure in the surrounding zone being in the range of about 50 kPa to about 200 kPa.

The maximum and minimum pressure that can be applied to any one cell type will be apparent to the competent skilled addressee. At pressures that are too low, the efficiency of the method may be compromised and at pressures that are too high, the cells may rupture. The optimum pressure differential may be identified for a particular cell by reference to the examples of the present application and through routine experimentation.

Preferably, the transient decrease in pressure that the cell is exposed to in the presence of the exogenous material is a decrease of at least about 10 kPa, at least about 100 kPa, at least about 500 kPa or at least about 1000 kPa. In certain embodiments, the transient decrease in pressure is a decrease in pressure (kPa) of at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950 or at least about 1000 kPa, or more.

The term "transient" in the context of a decrease in pressure means that the decrease in pressure occurs temporarily, in that after the cell is exposed to the decreased pressure, the pressure that the cell is exposed to afterwards will be of higher pressure. In some embodiments of the present disclosure, the transient decrease in pressure means that the cells are exposed to a minimum pressure reached during a particular exposure for at least about 10 nanoseconds, but no more than about 1 millisecond. It would be understood that this time is not inclusive of the time between when the cell is exposed to a maximum pressure in a surrounding zone to the moment when the cell is exposed to a minimum pressure in a zone of lower pressure relative to the pressure of the surrounding zone. This time is also not inclusive of the time between when the cell is exposed to a minimum pressure in a zone of lower pressure to the moment when the cell is exposed to a maximum pressure in a surrounding zone.

In preferred embodiments of the present disclosure, the cell subjected to at least one region of an unsteady flow is exposed to an electric field within a channel, preferably an enclosed channel, with dimensions configured to allow the flow of the liquid including the exogenous material and the cell therethrough. In the context of the present disclosure, by "channel" it is meant any component with a length and two or more ends, with a hollow space extending the length of the component that allows the flow of a liquid through the hollow space, and through openings at the two or more ends. The dimensions of the channel need only be configured to allow the flow of a relevant cell type in the liquid. A cross-section of the channel may have any shape. The channel preferably includes at least some enclosed sections but it is not necessarily sealed along the entirety of its length as long as there are areas within the channel in which the required pressure changes may occur. It would be understood that the flow of the liquid would essentially be from one end of the channel to the other, and the direction of the flow would determine the orientation of "upstream" and "downstream".

Flow through the channel may be caused by various means, including but not limited to hydrostatic pressure, hydrodynamic pressure and/or electro-osmotic flow. The flow of the liquid may be driven by a pressure source, including but not limited to, a pressure pump, a gas cylinder, a compressor pump, a vacuum pump, a syringe, a syringe pump, a peristaltic pump, a piston, a capillary pump, a heart, a muscle or gravity.

The flow of the liquid through the channel will have a velocity, and this velocity may be influenced by factors including, but not limited to, the configuration of the channel, the strength and nature of the pressure source, the viscosity of the liquid, the cell type and cell density in the liquid and/or the nature and amount of the exogenous material. The flow of the liquid may preferably be a cell velocity in a liquid. In certain preferred embodiments, the cell velocity in the liquid is estimated to be about 15 metres per second.

In preferred embodiments of the present disclosure, the velocity of the liquid fluctuates as it flows through the channel, and the fluctuating velocity may be defined in terms of a maximum velocity and a minimum velocity of the liquid as it flows through the channel. The velocity of the liquid may fluctuate between a particular maximum and minimum velocity as the liquid flows through the channel. Preferably, the fluctuating velocity of the liquid flowing through the channel has a minimum peak velocity of about 1 meter per second, or more preferably, about 5 meters per second. In other preferred embodiments of the present disclosure, the fluctuating velocity of the liquid flowing through the channel has a maximum velocity of about 10 meters per second, a maximum velocity of about 20 meters per second, a maximum velocity of about 30 meters per second, a maximum velocity of about 40 meters per second, a maximum velocity of about 50 meters per second, a maximum velocity of about 60 meters per second, a maximum velocity of about 70 meters per second, a maximum velocity of about 80 meters per second, a maximum velocity of about 90 meters per second or a maximum velocity of about 100 meters per second. Accordingly, it would be understood that the peak velocity of the liquid flowing through the channel may fluctuate between a range of about 1 meter per second to about 100 meters per second.

The present disclosure may also relate to devices for introducing exogenous material into a cell in a liquid including a channel with dimensions configured to allow the flow of the cell and exogenous material suspended in a liquid therethrough; and one or more flow diverters within the channel; wherein the flow diverter results in at least one region of decreased pressure immediately downstream of the flow diverter. In particular embodiments of the present disclosure, the device is a microfluidic device. In certain preferred embodiments, the device may be a device as substantially shown in FIG. 7 and/or FIG. 8.

It will be appreciated that a cell subjected to at least one region of unsteady flow may also be subjected to fluid forces in addition to unsteady flow. A skilled addressee will understand that unsteady flow refers to a laminar vortex street, a transitional vortex street, a turbulent vortex street, transitional flow or turbulent flow. The cell may be subjected to steady-state flow such as creeping flow or laminar flow. The skilled addressee would understand that creeping flow refers to a flow of liquid where the inertial forces of the liquid are significantly lower than the viscous forces of the liquid. Laminar flow refers to a flow of liquid where the inertial forces within the liquid are greater than or equal to the viscous forces of the liquid, but not great enough to induce transitional or turbulent flow in the liquid. The cell may be subjected to steady-state flow as it enters a channel, exits a channel, or both. In particular embodiments of the present disclosure, the channel is configured to influence the flow of the liquid such that there are one or more regions within the channel where the flow of the liquid is laminar, one or more regions within the channel where the flow of the liquid is creeping, and one or more regions within the channel where the flow of the liquid is unsteady.

As will be understood, the type of flow may be estimated by calculating two different Reynolds numbers: one for a particular flow through an enclosed channel (Rec) and/or region between a flow diverter, and one for flow around an object (Reo). For example, for creeping flow, Rec is significantly less than unity (Rec<<1) and for laminar flow, Rec is between unity and approximately two thousand three hundred (1<Rec<2300). Transitional flow commences at an Rec>2300. For example, for unsteady flow around an object, Reo is greater than approximately forty (Reo>40) or sufficient to induce unsteady flow. Rec may be defined as the ratio of the mean liquid velocity ($\bar{u}$) and the hydraulic diameter (Dh), to the kinematic viscosity (v) of the liquid, and this equation is defined as Rec=$\bar{u}$ Dh/v. For wide channels where the width is significantly greater than the height (or vice versa), Dh may be substituted with twice the length of the shorter distance. When calculating the channel Reynolds number (Rec) of flow between posts, this equation is used and the hydraulic diameter of the channel (Dh) refers to the hydraulic diameter of the channel between posts and the mean liquid velocity ($\bar{u}$) refers to the mean velocity between posts.

In preferred embodiments of the present disclosure, the flow of liquid is influenced by one or more flow diverters within the channel. It will be appreciated that the flow of the exogenous material past at least one flow diverter creates vortices or unsteady flow. In particular embodiments, the flow diverter is an obstacle placed in the channel. The term "obstacle" relates to any object placed within the channel that results in the flow of the liquid to be diverted around the object, resulting in a localized region of decreased pressure or decreased pressure coupled with unsteady flow substantially immediately downstream of the obstacle. The obstacle must be such that the cell can proceed through the channel beyond the obstacle. In preferred embodiments, the obstacle may extend outwards from an inner surface of the channel in a direction generally perpendicular to the length of the channel. The obstacle may extend from one side of the length of the channel to another side. Alternatively, the obstacle may only partially extend from one side of the length of the channel. In particular embodiments, the obstacle is a post. In the context of the present disclosure, an obstacle that is a "post" may be an obstacle that is a prism with a height greater than or equal to its greatest width. The post may be cylindrical, triangular, square, polygonal, wing-shaped or any other shape and the specific shape may be selected to tune the transient decrease in pressure for a given channel Reynolds number (Rec) and/or unsteady flow for a given object Reynolds number (Reo). In particularly preferred embodiments, the post is cylindrical.

Figure 7:
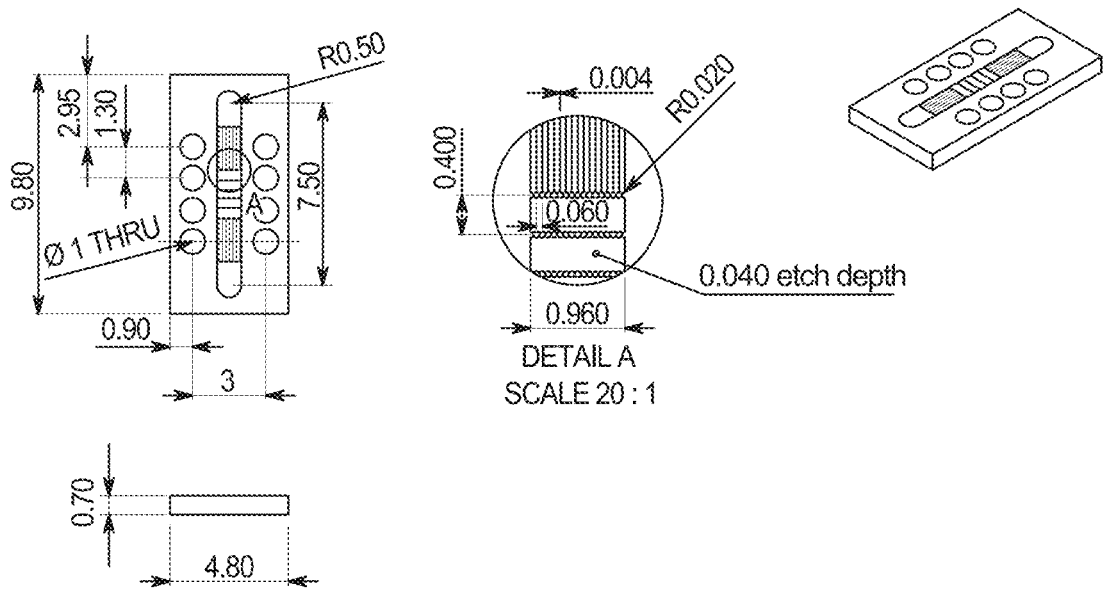
FIG. 7 is a schematic representation of a flow cell as disclosed herein.

Non-limiting examples of suitable channel configurations are provided in FIG. 1, FIG. 7 and Example 1. A preferred channel or device configuration includes approximately 5 mm×10 mm×1.4 mm (length×width×height or thickness) chip containing a 7.5 mm×1.5 mm×0.04 mm deep reactive ion etched microfluidic flow cell with a single inlet and single outlet. The inlet and outlet are laser machined with an approximately 700-µm inner diameter. In a preferred embodiment, the flow cell may include a post array having 5 rows (flow-wise) and 25 columns of posts (flow-perpendicular) where the posts have a diameter of 20-µm and a 40-µm height that is equal to flow cell depth. Post rows have a 500-µm (flow-wise pitch) and post columns have a 60-µm (flow-perpendicular) pitch.

The mean velocity of the flow through the channel and directly upstream of a flow diverter may be such that a transient decrease in pressure is induced just downstream of the flow diverter or a transient decrease in pressure and a localized region of unsteady flow is induced just downstream of the flow diverter. In embodiments of the present disclosure wherein the flow diverter is a post, appropriate inducing mean upstream velocities may be calculated using the Reynolds number for the flow of the liquid around the post (Reo). For the flow of a liquid around a cylindrical post, an Reo of at least forty (Reo≥40) is likely to be required to induce unsteady flow downstream of the post. For other post geometries, it is contemplated that the Reo required to generate unsteady flow may depend on the specific shape of post and the mean upstream liquid velocity would need to be tuned to create (1) a transient decrease in pressure of sufficient magnitude; or (2) unsteady flow and a transient decrease in pressure of sufficient magnitude. Reo is defined as the ratio of the mean upstream velocity ($\bar{u}$) and the characteristic length of the post (l) to the kinematic viscosity (v) of the fluid: Reo=$\bar{u}$ l/v.

In certain preferred embodiments, the object Reynolds number (Reo) of the flow of the liquid in at least one of the regions within the channel where the flow of the liquid is unsteady is at least about 40, but no more than about 150 to form a laminar vortex shedding. Alternatively, the object Reynolds number may be at least about 150, but no more than about 300 for transitional vortex shedding. The object Reynolds number may also be at least about 300 but no more than about 300,000 for turbulent vortex shedding or at least about 300,000, but no more than about 3,500,000 turbulent vortex shedding with a turbulent boundary layer or at least about 3,500,000 for re-established turbulent vortex shedding.

Although not wishing to be bound by any particular theory, in embodiments of the present disclosure there may be a localized region of unsteady flow substantially immediately downstream of a flow diverter, the cells may be exposed to a two-way increase in pressure as follows: (1) a localized increase in pressure caused by the unsteady flow; and (2) an increase in pressure following the transient decrease in pressure. This may create a pressure drop across the permeabilised cell membrane where the extracellular pressure is greater than the intracellular pressure and it may facilitate the active delivery of exogenous material near the cell membrane and/or exogenous material may be introduced into the cell by, for example, diffusion or flow from the local extracellular environment to the cytosol.

In other preferred embodiments, an unsteady flow is produced or induced by fluid inertia. According to these embodiments, a channel may be configured to induce turbulence by means of fluid inertia. In this embodiment the channel Reynolds number may be approximately greater than about 2,000 for transitional flow and may be approximately greater than about 4,000 for turbulent flow. In alternative preferred embodiments, surface roughness, geometry changes or a physical "trip" may be used to induce unsteady flow within an enclosed channel.

The method of the present disclosure may be used to introduce exogenous material to a population of cells, and within this population of cells, some cells may be lysed (and hence not viable), some cells may not be lysed but may not be viable, while others may be viable. Preferably, the substantially all of the cells are viable after treatment with the methods of the present disclosure.

The methods and devices of the present disclosure contemplate further including monitoring changes in temperature. Devices may include a thermocouple operatively connected to the flow path to monitor changes in temperature.

In embodiments of the present disclosure, the cell is exposed to an electric field in the presence of the exogenous material when both are in a liquid. The liquid may be any liquid that does not ordinarily result in lysis of the cell over the duration of the eµVS process and, in some embodiments of the present disclosure, is capable of maintaining the viability of the cell for the duration of the method. Preferably, the exogenous material would be soluble in, capable of being suspended in, or would be dispersible in, the liquid. By way of example, the liquid may be a cell growth media, or a buffered saline solution, such as phosphate buffered saline, or tris buffered saline. The liquid may be blood, plasma or serum or another bodily fluid, such as whole blood, cord marrow, bone marrow or adipose-derived fluids. The blood or bodily fluid may be fractionated, separated and/or diluted for improved processing. Although the fluid may contain agents or chemicals that promote the introduction of the exogenous material into the cell, the liquid need not necessarily contain any additional agents or chemicals to facilitate the introduction of the exogenous material into the cells. For example, in certain embodiments of the present disclosure, the liquid does not include any additional cationic lipids, cationic polymers, calcium ions (for example, in the form of calcium chloride or calcium phosphate), magnesium ions (for example, in the form of magnesium chloride), a charged polymer, or dendrimers. It would be understood that many of these chemicals and agents are toxic to cells, and the absence, or substantial absence of added amounts of these chemicals or agents in the liquid used in the method of the present disclosure may prevent unwanted cell lysis or cell death when performing the method of the present disclosure.

In embodiments that contemplate a cell suspension, it will be understood that the liquid of the suspension may be the liquid in a method of the present disclosure was performed on, with or without additional components. A cell suspension may also refer to a dessicated or alternatively, a freeze-dried formulation as is understood in the art.

By "additional" is meant any additional amount of the chemical or agent in addition to what may normally and/or naturally be present in the liquid. By way of example only, bodily fluids, such as blood, may naturally include calcium ions, but in particular embodiments of the present disclosure, no calcium phosphate would be added to the blood before being used as the liquid in a method of the present disclosure. In another example, a cell growth media may normally include magnesium ions, but in particular embodiments of the present disclosure, no magnesium chloride would be added to the growth media before being used as the liquid in the methods of the present disclosure.

The present disclosure contemplates pharmaceutical compositions. Suitably, the pharmaceutical compositions of the present disclosure include an appropriate pharmaceutically acceptable carrier, diluent, or excipient. Preferably the pharmaceutically acceptable carrier, diluent or excipient is suitable for administration to mammals and more preferably, to humans. By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. The present disclosure also contemplates pharmaceutical compositions including a cryoprotectant. Carriers may include excipients and other additives such as diluents, detergents, coloring agents, wetting or emulsifying agents, pH buffering agents, pH indicating reagent, preservatives, and the like. Useful reference describing pharmaceutically acceptable carriers, diluents and excipients is Remington's Pharmaceutical Sciences (Mack Publishing Co. N.J. USA, 1991) and Remington: The Science and Practice of Pharmacy (Pharmaceutical Press, London, 22nd Edition, 2012) which is incorporated herein by reference.

The methods of the present disclosure contemplate additional treatments or steps. By way of example, cell selection (e.g., fluorescently activated cell sorting or FACS) may be included to obtain high-purity genetically modified cell populations. In addition, there may be additional treatments or step interposed between the cell being exposed to at least one region of unsteady flow and exposure to an electric field.

In order that the present disclosure may be readily understood and put into practical effect, particular preferred embodiments will now be described by way of the following non-limiting examples.

EXAMPLES

Example 1

Microfluidics are being used to actively improve upon traditional intracellular delivery methods. However, a substantial need for a practical microfluidic intracellular delivery method remains, particularly within the scope of GMCT development and manufacturing. Here, the inventors detail a hydrodynamic intracellular delivery method based on µVS (shown in FIG. 6a-e), along with its optimization for enhanced green fluorescent protein (EGFP) mRNA delivery to human pan T cells. The following demonstrates that µVS results in high cell recovery (e.g., 96.3±1.1%, mean±stdev), high cell viability (e.g., 83.7±0.7%) and high EGFP expression efficiency (e.g., 57.4±6.8%) resulting a yield of 46.3±5.6% recovered, viable and EGFP expressing pan T cells after intracellular delivery via µVS. Indeed, it is also demonstrated that:

(1) µVS does not adversely affect T cell growth;
(2) µVS results in even EGFP expression profiles amongst T cell types; and
(3) µVS does not change T cell activation profiles.

This small-scale prototype also allows for processing rates of over 2 million cells s-1. Finally, this prototype is fabricated with industry standard semiconductor processes resulting in scalable device manufacturing with high yield (e.g., greater than 95%) and tight tolerances (e.g., less than 5%).

METHODS, DEVICE DESIGN & FABRICATION: Devices were designed with a 4.8 mm×9.8 mm footprint and contained a 960 µm wide by a 40 µm deep flow cell. This flow cell contained a post array of 40 µm diameter posts, with a pitch of 60 µm orthogonal to the bulk flow direction, and a 500 µm pitch in the bulk flow direction. An overview of the device is shown in FIGS. 1(b) and (c).

Device fabrication was achieved using industry standard semiconductor processes and fused silica wafers. The flow cell and array geometries were constructed through anisotropic deep reactive ion etching (see FIG. 1(c)). Deep reactive ion etched flow cells were thermally bonded to a fused silica lid containing approximately 700 μm diameter laser machined through holes for the inlet and outlet. After fabrication, device and feature geometries were verified using scanning electron microscopy (see FIG. 1(c)), white-light interferometry (not shown) and digital microscopy (not shown).

Experimental Rig Development: A purpose-built experimental rig was developed to operate microfluidic devices between 0 and 150 psig that could also measure flow rates ranging from 1 mL min$^{-1}$ to 1 mL s$^{-1}$. To accomplish this, a compressed nitrogen tank was regulated down to less than 150 psig using a calibrated two-stage regulator and filtered down to 5 μm using a compressed air filter (McMaster Carr, 4414K71). Compressed nitrogen flow was then controlled with a manual on/off valve (McMaster Carr, 4379K61) and volumetric flow rates were measured with a calibrated mass flow meter (Alicat Scientific, M-1SLPM-D). Compressed nitrogen was then used to pneumatically drive samples of suspended cells and agents through the microfluidic chip. The samples are housed in a 1.5 mL Eppendorf tube and placed in a tube adaptor (Elveflow, KRXS) which was coupled to an in-house fixture with outlet tubing for sample collection as seen in FIG. 1f.

Hydrodynamic Characterization & Simulation Non-dimensional equations were used to calculate the Reynolds number (Re) in channels and for flow around a cylindrical post. The equations are based on volumetric flow rate (Q), inematic viscosity of the fluid (v) and specific device geometries. Using the non-dimensional analysis, the following Reynolds numbers were found: flow cell (Re f c), inlet channels (Rec), gap between posts (Reg) and flow around an object (Reo) where the object is a cylindrical post. (Re f c), (Rec), and (Reg) were calculated as follows:

$$Re_{fc} = \frac{2Q}{v(h_{fc} + w_{fc})}$$

$$Re_c = \frac{2Q}{nv(h_{fc} + w_c)}$$

$$Re_g = \frac{2Q}{nv(h_{fc} + w_g)}$$

where Q is the device volumetric flow rate, hfc is the height of the flow cell and v is the kinematic viscosity of the fluid. The respective widths of the flow cell, channel and gap are $w_{fc}$, $w_c$, and $w_g$. n is the number of gaps or channels and is calculated by:

$$n = \frac{w_{fc}}{p_r}$$

where $p_r$ is the row pitch. $Re_o$ may be calculated as follows:

$$Re_o = \frac{v_\infty d}{v}$$

where $v_\infty$ is the free stream velocity and d is the post diameter. $v_\infty$ is calculated as follows:

$$v_\infty = \frac{Q}{h_{fc} w_{fc}}$$

$Re_o$ is then used to calculate the Strouhal number (St) for a smooth cylinder (Gerhardt et al. 2016) using the following equations:

$$St = 0.21\left(1 - \frac{21}{Re_o}\right) 40 < Re_o < 200$$

$$St = 0.198\left(1 - \frac{19.7}{Re_o}\right) 250 < Re_o < 2x10^5$$

St is then used to approximate the frequency (f) of vortex shedding using the following equation:

$$f = \frac{St v_\infty}{d}$$

The inventors also used two-dimensional computational fluid dynamics techniques and ANSYS Fluent to simulate hydrodynamic conditions in the unit array geometry using $v^\infty$ as the inlet velocity. This was done to assess μVS flow development time at representative hydrodynamic conditions. μVS flow development time was simulated by examining the transient drag coefficient (not shown) acting on the posts while also looking at velocity contours (see FIG. 1(i)).

Pan T Cell Culture: Cryopreserved, purified primary CD3$^+$ T cells were negatively selected from single donor PBMCs (denoted as pan T cells or T cells) using standard techniques and provided as a gift by Eureka Therapeutics. For revival and culture, 5 million pan T cells cell were thawed and seeded in X-VIVO10 with gentamycin and phenol red (Lonza). The cells were activated using CD3/28/2 T cell activator solution (StemCell Technologies) and 100 IU mL$^{-1}$ recombinant human IL-2 (PeproTech) on the day of thaw and cultured at 37° C. in 5% $CO_2$. Pan T cells were expanded for 16 days with addition of medium and IL-2 (final concentration 100 IU mL$^{-1}$) every two to three days to keep cell concentration at or below 1 million cells mL$^{-1}$. All data was collected between days 17 and 24 post-thaw and activation.

EGFP mRNA Delivery to Pan T cells at Different Concentrations: The solutions used on chip were filtered using 0.22 μm filtration prior to use to remove particulates that could lead to clogging. For on-chip cell processing, T cells were removed from culture and pelleted via centrifugation (5 min at 300×g). The supernatant was removed via aspiration and the cell pellet was suspended in 1× Dulbecco's phosphate buffered saline (DPBS, Gibco), pelleted via centrifugation again, and the supernatant was removed via aspiration. The rinsed cells were suspended in filtered processing medium composed of lmmunocult-XF (Stem Cell Technologies), 25 mM trehalose dihydrate NF (JT Baker, VWR) and 5% v/v DMSO (Corning Cellgro, Fisher Scientific) at a cell concentration around 20 million cells mL$^{-1}$. The cell concentration was enumerated using the Countess automated benchtop cell counter (Invitrogen) and trypan blue dye exclusion to assess viability. Three replicate samples of cell solutions were made for each of the eight conditions to be tested. To make the samples, 6.4 million cells were removed from the enumerated stock in processing medium, placed in Eppendorf Biopur 1.5 mL tubes, and diluted with processing medium to the final volume of 400 µL minus mRNA volume, which was added immediately before processing, for 16 million cells mL$^{-1}$ final cell concentration. These samples were filtered in two separate batches (160 µg mL-1 mRNA control, 10 µg mL$^{-1}$, 40 µg mL$^{-1}$, and 80 µg mL$^{-1}$ as the first set of samples, handling control, 120 µg mL$^{-1}$, 160 µg mL$^{-1}$ and no mRNA device processed control as the second set) to reduce cell clumping and cluster formation, which can lead to chip clogging.

The sample rig and tubing was sterilized before use via 70% ethanol wipe down and the tubing cleaned with an ethanol flush between runs. Immediately before processing, each sample was mixed with the appropriate volume of EGFP mRNA (1 mg mL$^{-1}$ TriLink BioTechnologies, San Diego CA, L-7601) at final concentrations ranging from 10 µg mL$^{-1}$ to µg mL$^{-1}$ (30 nM to 473 nM). The sample was mixed thoroughly using pipetting to evenly suspend cells, the sample tube mounted in the Eppendorf tube fitting, and the fitting tightly clamped shut. The Eppendorf tube with cells and mRNA was then exposed to 120 psig nitrogen pressure to drive the sample through the chip and induce intracellular mRNA uptake via µVS (see FIG. 6a-e). Processed sample was collected in a 15 mL conical tube and held on ice until the completion of the experiment, in order to sync expression time points between the different samples. After each run, the rig and tubing were flushed with 70% ethanol and a new microfluidic chip was replaced in the rig. Time equals zero for mRNA expression started when all samples were processed, removed from ice and returned to culture medium. All samples within a set were processed within 30 min and total time on ice for the samples ranged from thirty minutes to three hours, which was the length of time the 10 µg mL$^{-1}$ sample was held on ice. Control samples were set up in triplicate and allowed to sit at room temperature while the experimental samples were processed. Control samples that were not device processed consisted of 16 million cells mL$^{-1}$ in pure processing medium (handling control), which was used to normalize the cell viability and recovery for the experimental samples, and in processing medium containing 160 µg mL$^{-1}$ mRNA (mRNA control). Additional device control samples were set up at 16 million cells mL$^{-1}$ in pure processing medium and ran through the device to determine the impact of µVS on cell survival without additional external factors. Two triplicate handling control samples (the first including mRNA) were made for the two batches of filtered cell described previously.

After the last sample was processed and incubated on ice for 5 min, all samples were removed from ice, re-suspended, and a sample removed for post processing cell viability and concentration quantitation using the Countess and trypan blue dye. The remaining cells in processing medium were diluted 1 to 20 in X-VIVO10 at a concentration of around 8×10$^5$ cells mL$^{-1}$ with 100 IU mL$^{-1}$ IL-2. The cultures were added to 6 well non-TC treated well plates and cultured at 37° C. in 5% CO$_2$ for growth, activation marker, and EGFP expression analysis at later times. Cell growth was monitored using trypan blue dye exclusion quantified using the Countess II cell counter. Additional IL-2 was added on days 2 and 4 after transfection and the cells were discarded on day 7, at a culture age of 24 d post-thaw and activation.

Figure 2:
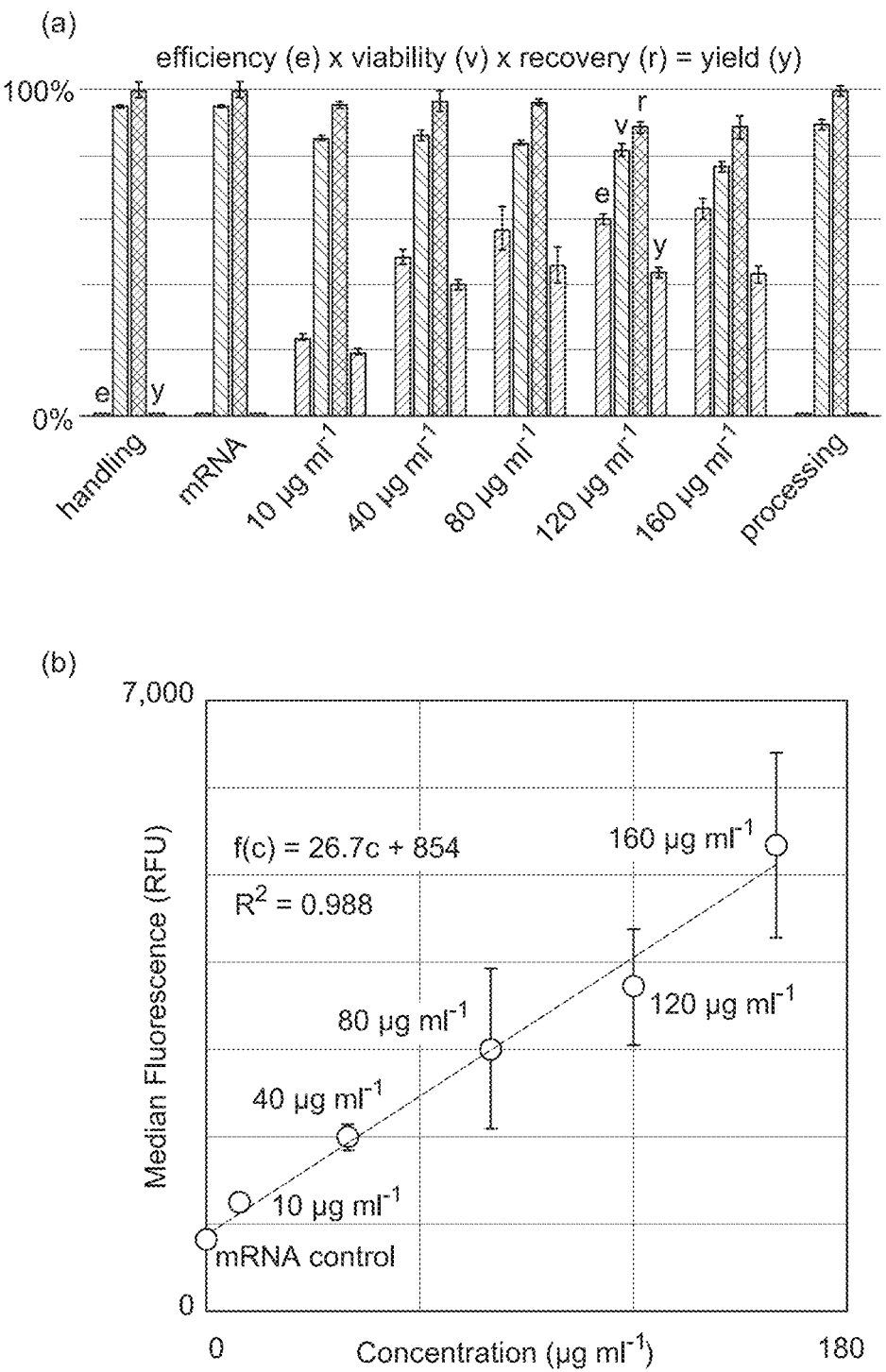
FIG. 2 is a graphical representation of primary T cell EGFP mRNA expression efficiency at 19 h post transfection using different mRNA transfection concentrations according to the method schematically represented in FIG. 1.
Figure 3:
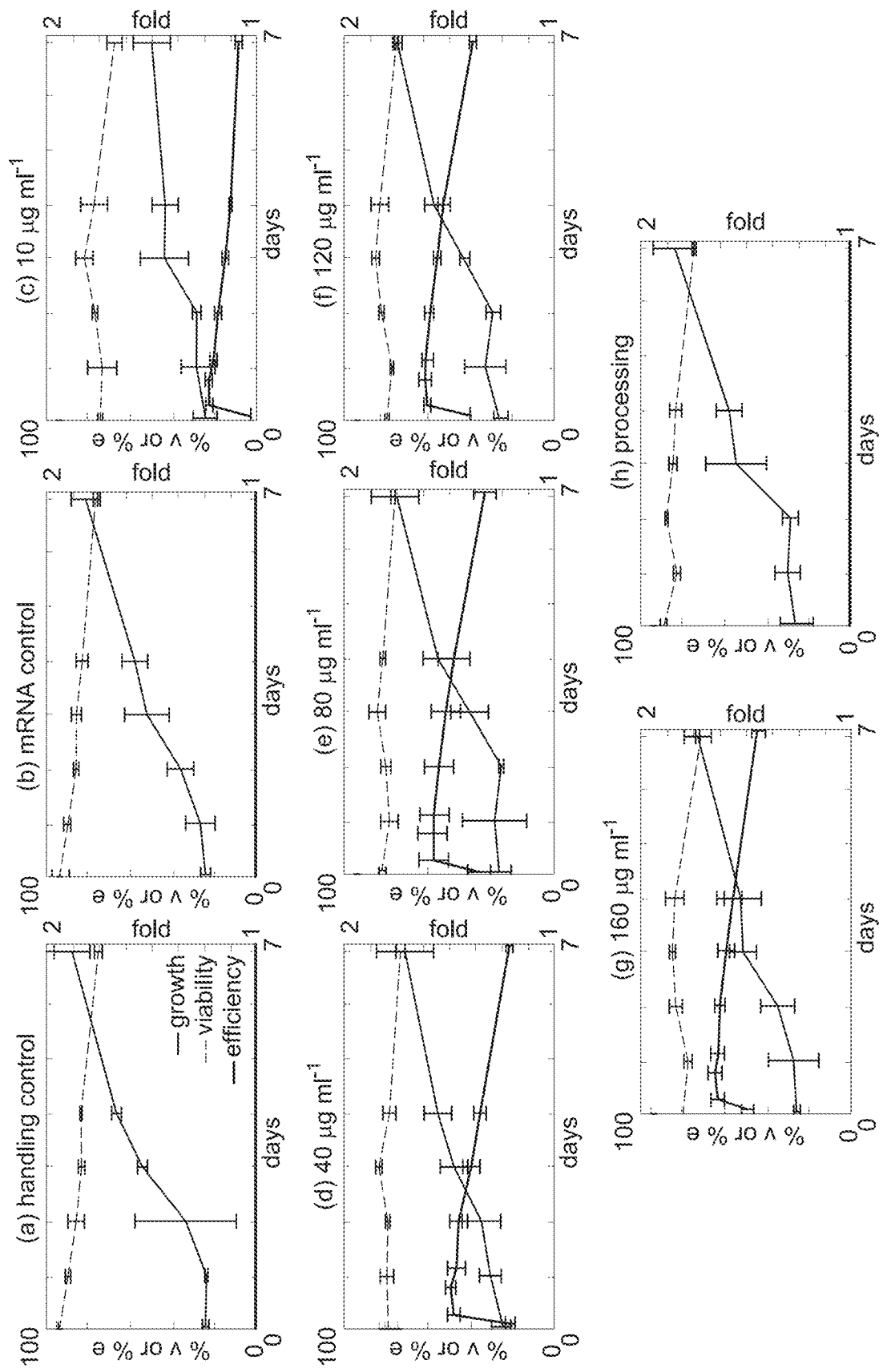
FIG. 3 is graphical representation of T cell growth, viability and EGFP mRNA expression efficiency over 1 week using different mRNA transfection concentrations according to the method schematically represented in FIG. 1.

Initial T cell viability and post processing concentration were quantified by counting a minimum of two unique samples from each sample replicate using the Countess and trypan blue staining. These counts were used to determine the recovery and yield shown in FIG. 2a. Cell growth and viability of each sample in growth medium was monitored over a period of seven days using Countess with trypan blue dye exclusion (FIG. 3). EGFP expression and persistence at different time points post transfection, FIG. 3, was monitored using flow cytometry (Attune N×T flow cytometer) and propidium iodide (1 µM final concentration, Sigma Aldrich) to exclude dead cells. FIG. 2 shows a graphical representation of primary T cell EGFP mRNA expression efficiency at 19 h post transfection using different mRNA transfection concentrations according to the method schematically represented in FIG. 1. Primary T cell EGFP mRNA expression efficiency at 19 h post transfection, post processing cell viability, cell recovery, and total yield of transfected cells using different mRNA transfection concentrations (n=3) was determined (FIG. 2(a)). In all conditions, high recovery (e.g., greater than 88%) and viability (e.g., greater than 77%) was achieved after µVS transfection. EGFP fluorescence intensity from live single T cells was analyzed via flow cytometry as a function of mRNA concentration at 19 h after transfection and return to culture (FIG. 2(b)). Transfection efficiency ranged from approximately 24% to 64% for 10 µg mL$^{-1}$ (30 nM) to 160 µg mL$^{-1}$ (473 nM). There was also a linear relationship between median population EGFP fluorescence (in relative fluorescence units) and mRNA concentration.

Expression efficiency along with cell recovery and cell viability were enumerated as a function of mRNA concentration to determine the mRNA concentration that results in the highest yield of recovered, viable and transfected cells where yield is defined as:

$$y = rve$$

where y is yield or the fraction of recovered, viable and transfected cells or percent of input cells that remained viable and expressed EGFP after device transfection. r is the fraction of recovered cells. v is the viability of the recovered cells. e the efficiency of transfection or the fraction of viable cells expressing EGFP.

Yield and efficiency of EGFP expression (FIG. 2b) was calculated using the highest EGFP expression value for the cultures, which occurred at approximately 19 hrs post-processing and return of the cells to culture medium.

Even Expression Profiles in T cell Subtypes from a Single Donor: Expression efficiency was examined among CD4$^+$ and CD8$^+$ T cell subtypes using fluorescent monoclonal antibody labeling and flow cytometry analysis. These cultures were analyzed 27 h after being returned to culture medium. Samples were removed from each of the 10, 80, and 160 µg mL$^{-1}$ cultures, placed in a v-bottom 96 well plate, diluted with DPBS, pelleted via centrifugation and supernatant aspirated. The cells were re-suspended in 100 µL$^{-1}$ of 25 µg mL$^{-1}$ each mouse anti-human CD3$^-$Alexafluor700 (ThermoFisher PN 56-0037-42), mouse anti-human CD4-PE-Cy7 (ThermoFisher PN 25-0048-42), and mouse anti-human CD8a-Super Bright 600 (ThermoFisher PN 63-0088-42) in DPBS containing 1% bovine serum albumin and 2 mM EDTA (FACS buffer). The previous antibodies were used to quantify the percentage of CD4$^+$ and CD8$^+$ T cell subtypes expressing EGFP. Cells were incubated in the antibody mixture on ice for 30 minutes, then diluted with 100 µL FACS buffer, pelleted via centrifugation, and supernatant aspirated. The samples were re-suspended in 200 µL FACS buffer, pelleted via centrifugation, and the supernatant aspirated as a second rinse step before being re-suspended in 200 µL FACS buffer and analyzed via flow cytometry. The experiment was compensated using a combination of AbC compensation beads (ThermoFisher) labelled with the antibodies and EGFP expressing cells (BL1 channel).

No Change in T cell Activation: To assess the impact of μVS-based mRNA delivery on T cell activation, handling control and device processed control (no mRNA) cells were labelled with fluorescent labelled antibodies against various activation markers 24 hours after return to culture. One sample per activation marker from each replicate in the control and device processed groups were removed from culture and diluted in a 96-well plate with DPBS. The cells were pelleted via centrifugation (1.5 min 800×g), supernatant removed by aspiration, and re-suspended in FACS buffer containing 25 μL mL$^{-1}$ of one of the following ThermoFisher monoclonal antibodies per sample: CD40L/CD154-FITC (PN 11-1548-42), CD25-PE (PN 120257-41), CCR7-APC-eFluor780 (PN 47-1979-42), CD44-APCeFluor780 (PN 47-0441-80), CD69-eFluor450 (PN 48-0699-42), CD45RA-Super Bright 702 (PN 67-0458-42). The samples were incubated on ice for 30 minutes, rinsed twice with FACS buffer, and analyzed via flow cytometry.

RESULTS & DISCUSSION: Device Design & Fabrication Deep reactive ion etched fused silica features resulting in vertical sidewalls (see FIG. 1h) and thermal bonding resulted in a bulk material bond. The microfluidic chips produced during the method could withstand operating pressures well above those required for this study. Moreover, the use of an optically-transparent fused silica substrate (see FIG. 1g) allowed for device inspection before and after processing.

TABLE 1

Summary of designed and fabricated device geometries

| Feature | Design | Fabrication | Difference |
|---|---|---|---|
| Flow cell height (h$_{fc}$) | 40.0 μm | 40.9 μm | 2.3% |
| Post diameter (d) | 40.0 μm | 42.2 μm | 4.0% |
| Row pitch (p$_r$) | 60.0 μm | 59.5 μm | −0.8% |
| Channel wall thickness (t) | 6.0 μm | 6.2 μm | 3.3% |

The use of semiconductor processes meant there was minimal variation (see Table 1) between designed device geometries and fabricated device geometries. Moreover, device yield or the percentage of successfully fabricated devices was typically 95%. This is attributed to relatively simple device geometries. The maximum fabricated feature aspect ratio, for example, was approximately 6.6. Deep reactive ion etching is frequently used to generate features with substantially higher aspect ratios.

Devices were designed containing inlet and outlet channels for more uniform flow conditions along with improved cell recovery. In preliminary experiments, device designs containing open or channel-free inlets and outlets were also capable of intracellular delivery or transfection. However, cell recovery was significantly lower and cell debris or build-up on the upstream side of the post was observed. These preliminary device designs were also prone to clogging when processing larger volumes of cells and at high cell densities. This clogging was attributed to mechanical lysis of cells after impacting a post.

The introduction of inlet and outlet channels substantially reduces the opportunity for this form of cell lysis along with the related device clogging. In the specific design used in this study fabricated posts occupy approximately 68.2% of the flow cell width whereas the fabricated inlet and outlet channels structures occupy approximately 10.3% of the same flow cell width. Cellular debris is still observed at the inlet of the channels after processing, but cell recovery rates remain high (see section regarding Pan T Cell culture) and the device are less prone to clogging particularly at the cell densities used in this study.

Experimental Rig Development: Microfluidics equipment is typically limited to low flow rates, small sample volumes and low operating pressures. Thus, custom test rig development was required to generate the high pressures required to generate μVS within the microfluidic chip. Direct measurement of microfluidic flow rates was not feasible with readily available commercial equipment due to the (1) significant flow rates, (2) sensitive nature of primary T cells, and (3) short flow times. For example, when processing a 400 μL sample containing cells at a density of 16 million cells mL$^{-1}$ using an operating pressure of 120 psig (8.2 ATM) the measured flow rates were typically 8 mL min$^{-1}$ resulting in a total sample flow time of approximately 3 seconds. Additionally, the brief sample flow time coupled with limited tubing lengths between the mass flow meter and the chip fitting meant artifacts caused by the diffusion and permeation of compressed nitrogen through the tubing wall was thought to be negligible, relative to flow of nitrogen driving the sample through the tubing and chip.

This purpose-built system allowed the inventors to quantify flow rates without disrupting (1) the hydrodynamic conditions within the chip or (2) flow of samples through the tubing. During preliminary experiments, it was observed that significant bends and kinks in the tubing would adversely affect both cell viability and recovery—this was attributed to high shear recirculation regions created within the deformed tubing. Furthermore, careful selection of tubing was required to generate the ideal flow conditions. Small changes in the inner diameter of the tubing would result in significant changes in volumetric flow rates and hydrodynamics conditions within the chip, while excessive tubing lengths increased total sample loss. This means due care was needed when engineering an experimental rig that allowed for quantitative flow measurements along with a pristine flow path. Cumulatively, this purpose-built experimental rig meant cells are only subject to precisely-controlled hydrodynamic conditions within the microfluidic chip.

Hydrodynamic Characterization & Simulation: Non-dimensional analysis was used to characterize flow conditions in the (1) device flow cell, (2) inlet channels, (3) between posts, and (4) around the posts. Hydrodynamic conditions were characterized and simulated using a kinematic viscosity of 1.004×10-6 m$^2$ s$^{-1}$ or that of water at 20° C., as cell medium consists mostly of water, and transfections were done at room temperature (approximately 20° C.). Different transfection media compositions were shown to have the same dynamic viscosity to water at 20° C. at high shear rates (not shown). Moreover, the purposes of the hydrodynamic characterization and simulation is to provide a reasonable analysis of the hydrodynamic conditions. To this end, a summary of the non-dimensional analyses is shown in the table (Table 2) below:

TABLE 2

Non-dimensional and hydrodynamic characterization of μVS

| Parameter | Units | Value |
|---|---|---|
| Flow cell Reynold's number (Re$_{fc}$) | — | 271 |
| Channel Reynold's number (Re$_c$) | — | 180 |
| Gap Reynold's number (Re$_g$) | — | 291 |

TABLE 2-continued

Non-dimensional and hydrodynamic characterization of μVS

| Parameter | Units | Value |
|---|---|---|
| Object Reynold's number ($Re_o$) | — | 146 |
| Strouhal number (St) | — | 0.18 |
| Frequency (f) | kHz | 14.8 |

The table above shows that flow conditions within the flow cell ($Re_{fc}$), channels ($Re_c$) and at the gap between posts ($Re_g$) are 271, 180, and 291, respectively. These values are well below the Reynolds number for the onset of transitional and turbulent flow. Thus, flow conditions upstream of the post array are laminar and the hydrodynamic conditions within the microfluidic device can be attributed solely to vortex shedding since $Re_o$=146 and vortex shedding is known to occur when $Re_o>40$. Microfluidic fluid dynamics are well studied with Reynolds number-matched micro- and macro-scale flows having the same characteristics in complex flow conditions. Furthermore, vortex shedding has been previously shown to occur in microfluidic post arrays. Vortex shedding occurs in the near wake behind posts, and due to the flow instability, resulting in fluctuating flow fields and thus drag and lift forces. Thus, it is reasonable to conclude vortex shedding is occurring in these specific microfluidic post arrays.

Simulation via computational fluid dynamics was also used to confirm the hydrodynamic flow conditions, showing the development of vortices in the wake and it was thereby possible to investigate the vortex shedding frequency, and determine flow development times for μVS. Flow development time was used to assess what percentage or fraction of each sample is exposed to fully-developed μVS and to approximate the minimal theoretical sample size. As shown in FIG. 1i, flow conditions are fully-developed after approximately $10^{-4}$ s. Furthermore, drag coefficient analyses suggests μVS flow development times is $3\times10^{-4}$ s at a device flow rate of 8 mL min$^{-1}$. Meaning, flow development times account for an estimated 0.01% of total sample flow time when 400 μL samples are processed. This is particularly significant when small samples are needed for research applications where minimal reagent consumption is ideal and cells in the sample are precious. In this flow condition, vortices occurs downstream of the cylindrical posts affected each other and near anti-phase synchronized regime is the dominant flow pattern.

The hydrodynamic characterization and simulation methods described in this example assume single-phase fluid dynamics. The region immediately between the fabricated posts contains a volume of approximately 4.6 pL, whereas each individual cell occupies a suspension volume of approximately 62.5 pL at a cell concentration of 16 million cells mL$^{-1}$—suspension volume refers to the total volume of a single cell and surrounding suspension medium assuming even distribution of medium between suspended cells in the medium. This means the total suspension volume per cell is 13.6-fold greater than the volume immediately between posts. It was assumed cells are individually processed with negligible cell-cell interaction when passing through the post array and single-phase fluid dynamics is a reasonable assumption when characterizing and simulating the flow conditions. Furthermore, pan T cells from this donor are typically 8 to 10 μm in diameter. A 9 μm diameter sphere has a volume of 0.38 pL—a typical pan T cell from this donor occupies a volume that is 12.1-fold smaller than the volume immediately between posts. Cell-post interaction is minimal for cells positioned near the middle of each channel. Channel widths and heights are approximately 6.6-fold and 4.4-fold greater than typical pan T cell from this donor suggesting most cells flow immediately between the posts. These relative volumes and geometries mean the major of interactions are fluid-cell or fluid-post interactions such that more advanced three-dimensional and multi-phase simulations were not warranted.

Pan T cell Culture: Cryopreserved pan T cells were expanded out from an individual sample of 5 million over a period of 16 days to a cell number that was sufficient for the experimental workflow. For development experiments, expanded T cells were transfected at or after two weeks from the initial activation, allowing the T cells to return to a resting state based on activation, and exhaustion marker expression.

EGFP mRNA Delivery to pan T Cells at Different Concentrations: High efficiency and low time requirement transfection methods like electroporation often results in reduction of cell viability and recovery in T cell transfection with mRNA. Comparatively, μVS-based molecule delivery substantially reduces processing time and impact on T cell health. Delivery of 30 nM to 473 nM EGFP mRNA to pan CD3$^+$ cells resulted in maximum EGFP expression ranging from approximately 20% to 65% of the live, processed cell population at 19 h (FIG. 2a-b). Interestingly, the median population EGFP fluorescence intensity is linearly correlated with mRNA concentration (FIG. 2(c)). The short processing time (e.g., approximately 3 s for 400 μL samples) allows for cells to be returned to cell culture medium immediately after processing. This promotes rapid recovery and reduces stress and damage that occurs to cells from long periods of time in low or serum free medium, such as the conditions required for chemical transfection. Additionally, μVS is a seemingly gentler intracellular delivery method when compared to electroporation, resulting in high recovery (e.g., greater than 88%) and viability (e.g., greater than 77%) in conditions tested, whereas electroporation can result in low viability and recovery, especially for primary immune cells.

It was found that the medium composition has a direct impact on cell recovery and viability as well as overall efficiency for μVS mRNA delivery. A variety of serum free media options were screened and found that over all yield (y) was highest for Immunocult-XF compared to other serum-free medium options, including the X-VIVO10 medium used to propagate the T cells. Trehalose was added to the media to enhance cell viability and recovery. Trehalose is commonly used as an excipient and has been demonstrated to reduce cell loss during electroporation. Finally, 5% v/v DMSO was added to the processing medium as a cosolvent, with the idea of increasing the ease of pore generation or perhaps size of the pore in the cell membrane upon exposure to μVS. DMSO has been used to increase cationic lipid chemical transfection efficiency, and to generate pores in mammalian cells for intracellular DNA delivery with polybrene. The addition of a cosolvent is thought to aid in the reduction of membrane resistance to poration.

Medium ionic strength or conductivity may also have an impact on the overall ease of pore generation and cell recovery with μVS. A trend of decreasing viability with increasing mRNA concentrations was observed, though this decrease was slight. This is potentially due to the higher percentage of mRNA solution added to samples containing higher concentrations of mRNA. For example, a 10 μg mL$^{-1}$ sample contained 1% v/v mRNA buffer in the processing medium, while 160 μg mL$^{-1}$ sample contained 16% v/v mRNA buffer. The mRNA solution is at a low ionic strength buffer (e.g., 1 mM sodium citrate) relative to lmmunocult-XF. This means that the reduction in total processing medium ionic strength associated with increasing mRNA concentration is likely the cause of decreasing viability trend. The presence of the mRNA solution also decreases the concentration of trehalose, which could also result in lower cell viability with increasing mRNA concentration.

Additionally, the decrease in viability and relatively lower growth rate of the 10 µg mL$^{-1}$ sample (see FIG. 3(c)) compared to the other concentration is hypothesized to be a result of extended time on ice (approximately 3 h total) after processing, as this as the first group to be processed and had the longest incubation period on ice and time between processing and return to medium. The decrease in viability of all groups compared to the handling control may be due to increased cell death upon return to culture due to unsuccessful membrane repair attempts, bulk mechanical lysis along with thermal shock, and medium stress.

The total cell recovery rates for µVS were exceptionally and surprisingly high. Conventional T cell recovery rates are typically 20% after electroporation, meaning, µVS offers a nearly 5-fold improved T cell recovery relative to conventional electroporation. Along with low recovery, electroporation is also known to adversely affect T cell viability. There are reported challenges with T cell viability with viability ranging from 15% to 40% after electroporation). There are also observations of further cell death over 2 to 3 days particularly when high concentrations of plasmid were used. µVS, on the other hand, does not affect cell viability nor cell growth relatively to handling and mRNA controls (FIG. 3). A slight decrease in T cell viability and growth is observed when comparing the mRNA control (FIG. 3b) to the 160 µg mL-1 (FIG. 3g), however, it is small. When comparing the device processed control cells (FIG. 3h) to the handling control (FIG. 3a), the growth rate and viability are nearly identical over the entire seven day culture period, indicating that the modest reduction in viability and growth rate for mRNA processed cells is likely due to the presence of the mRNA solution and not the effects of processing cells using µVS. Cumulatively, this suggests µVS is a gentler method for T cell intracellular delivery relative to electroporation while also allowing for significant EGFP mRNA expression efficiency—this resulted in substantial yield of recovered, viable and EGFP expressing T cells. FIG. 3 shows T cell growth, viability and EGFP mRNA expression efficiency over 1 week for the (a) handling control, (b) mRNA control, (c) 10 µg mL$^{-1}$, (d) 40 µg mL$^{-1}$, (e) 80 µg mL$^{-1}$, (f) 120 µg mL$^{-1}$, (g) 160 µg mL$^{-1}$ and (h) device processed control samples. After transfection and return to culture medium, the cell viability (blue line) and concentration (plotted as fold concentration increase, black line) from each group was monitored using trypan blue dye exclusion and an automated cell counter in triplicate. EGFP expression and persistence was quantified using flow cytometry at different time points after transfection. The resulting plots demonstrate that cell growth rate and viability was not adversely affected from on chip mRNA transfection using µVS. All groups demonstrated a 2-fold increase in concentration from post processing growth, except the 10 µg mL$^{-1}$ group, which may have undergone extra stress due to spending the longest time on ice between processing and recovery. Additionally, the persistence of EGFP protein was monitored (green line) and appeared to decrease in signal due to cell growth and protein degradation.

Even Expression Amongst T cell Subtypes from a Single Donor To assess if there was a population bias for µVS mRNA delivery, samples of T cells from three of the mRNA concentrations (10, 80, and 160 µg mL$^{-1}$) were labelled with CD3, CD4, and CD8a fluorescent antibodies. The hypothesis was that activation state, cell age, or phase of cell cycle may affect cell susceptibility to µVS induced poration. The samples were analyzed via flow cytometry and the distribution of T cell types analyzed for EGFP fluorescence. The results shown in FIG. 4 demonstrates the percentages of EGFP expressing cells is the same between all CD4$^+$ or CD8$^+$ populations throughout all experimental conditions. Additionally, the mRNA concentration-dependent fluorescent intensity profiles are also nearly identical showing reproducibility between the CD4$^+$ and CD8$^+$ T cell subtypes.

Figure 4A:
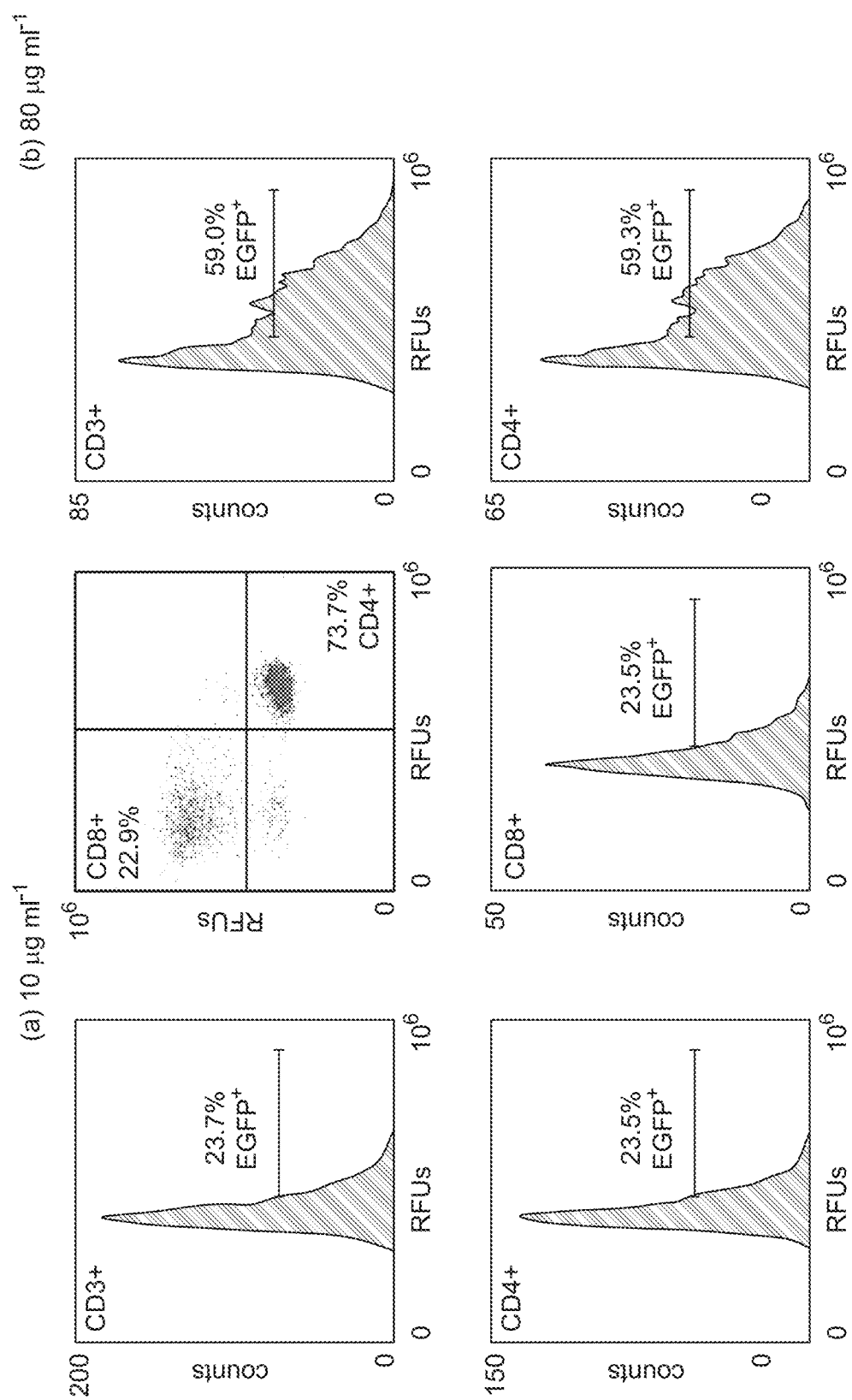
FIGS. 4A and 4B are graphical representations of EGFP mRNA expression that is equally distributed between the two types of CD3+ cells from a single donor.
Figure 4B:
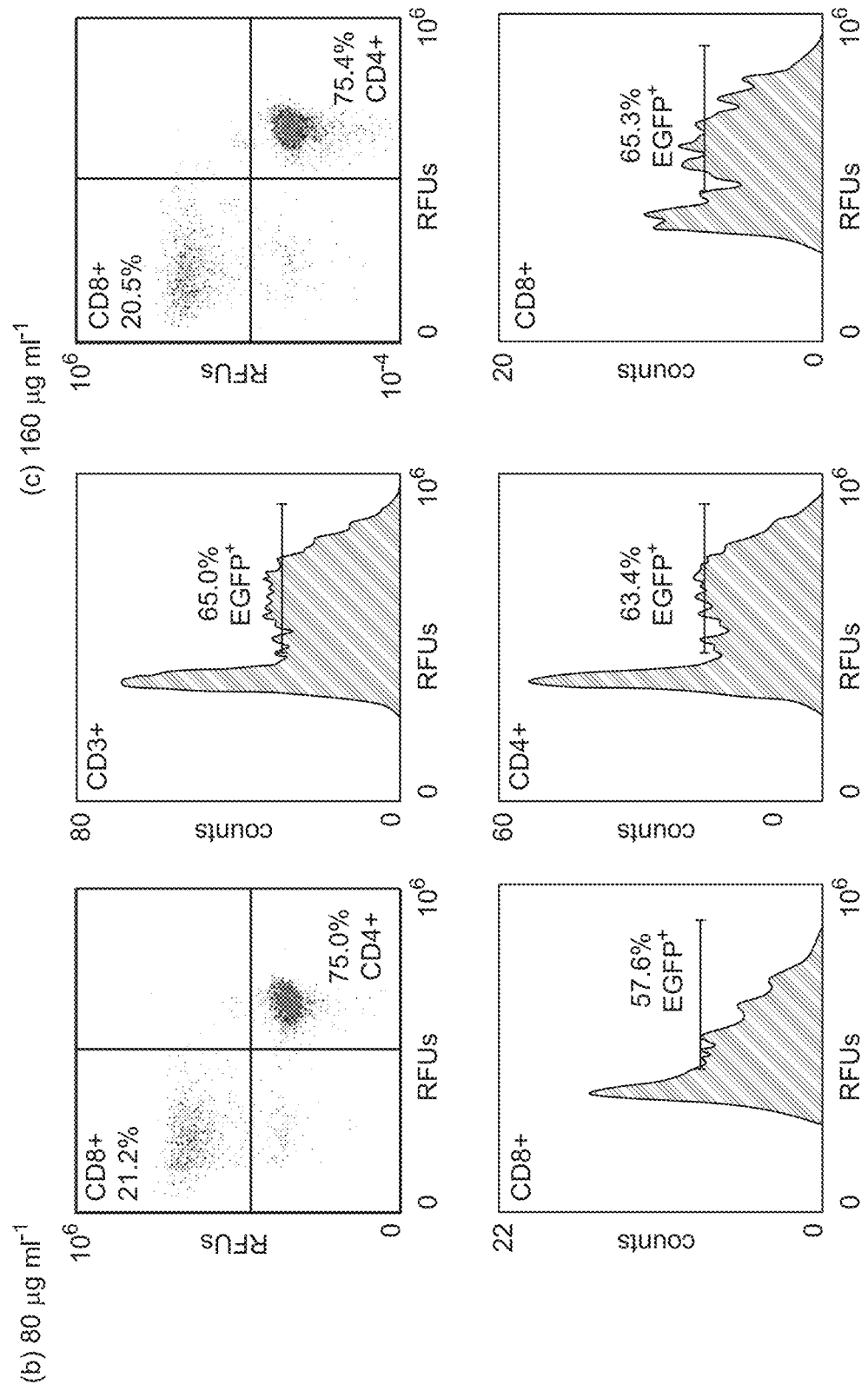

This equal distribution is advantageous for GMCTs focused on using mixtures of CD4$^+$ and CD8$^+$ T cells instead of isolating a pure population of T cells. It is also advantageous for point-of-care GMCT manufacturing where less pre-processing of PBMCs prior to genetic manipulation and re-infusion is preferred. These even distribution profiles may also be unique to µVS. Lentiviral transduction efficiencies are known to differ amongst T cell subtypes without a consistent trend between donors while electroporation is shown to adversely affect CD8$^+$ T cell populations resulting in 40% CD8$^+$ T cell viability. Furthermore, expression profiles are known to differ between CD4$^+$ and CD8$^+$ T cells after plasmid electroporation. Cumulatively, the data shown in FIG. 4 demonstrates even expression profiles amongst CD4$^+$ and CD8$^+$ T cell subtypes after cytosolic delivery of EGFP mRNA and suggests that µVS provide an additional advantage over electroporation and lentiviral transduction at least when considering cytosolic intracellular delivery. FIG. 4 shows EGFP mRNA expression is equally distributed between the two types of CD3$^+$ cells from a single donor. µVS-based mRNA delivery results in even distribution of expression among the CD8 and CD4 T cells, which is equal to that of the whole CD3$^+$ population EGFP expression. The percentage of CD3$^+$ cells expressing EGFP (upper left histogram) translates to the specific CD4 and CD8 T cell groups (bottom left and right histograms respectively), which were distinguished using fluorescent labelled antibodies (upper right scatter plot), demonstrating no bias for mRNA delivery for helper or cytotoxic T cells. EGFP positive percentages are shown for (a) 10 µg mL$^{-1}$, (b) 80 µg mL$^{-1}$, and (c) 160 µg mL$^{-1}$.

No Change in T cell Activation: It has been observed that electroporation of primary human immune cells increases activation markers in T cells. There have been observations that 24 hours after electroporation and return to culture, there was an increase in expression of CD69, an early marker of T cell activation, and CD154, activation marker that serves in co-stimulation of antigen presenting cells, indicating that electroporation results in activation of CD4$^+$ T cells. In this example, we examined whether processing cells using µVS would result in a change in the cell activation state compared to cells in culture (see FIG. 5). Each replicate from the handling control, and device processed control groups were individually labelled with different antibodies against various activation markers. CD69 and CD154, as well as the additional markers of activation CCR7, CD25, CD45RA, and CD44. CCR7 is a lymphoid homing cytokine receptor found on naïve T cells and is lost upon activation. CD25 is a later marker of activation compared to CD69, which increases upon cell activation and persists on activated the cell surface longer than CD69. CD45RA is found on naïve T cells and is lost upon activation and formation of memory. CD44 is a receptor for specific extracellular matrix components and is upregulated upon T cell activation. A shift in the histogram shape, population distribution, or change in fluorescence intensity for the device processed cells compared to that of the handling control would demonstrate that μVS exposure impacts T cell activation state of μVS processed cells. After the experiment, cells were returned to culture medium with IL-2 for 24 h to recover and allow time for activation marker expression or alteration of activation state. Isotype control for mouse IgG1 kappa was previously determined to have no off target or non-specific binding interactions with the T cells (not shown). Thus, shifts in fluorescence intensity for the various markers were due to specific interactions.

Figure 5:
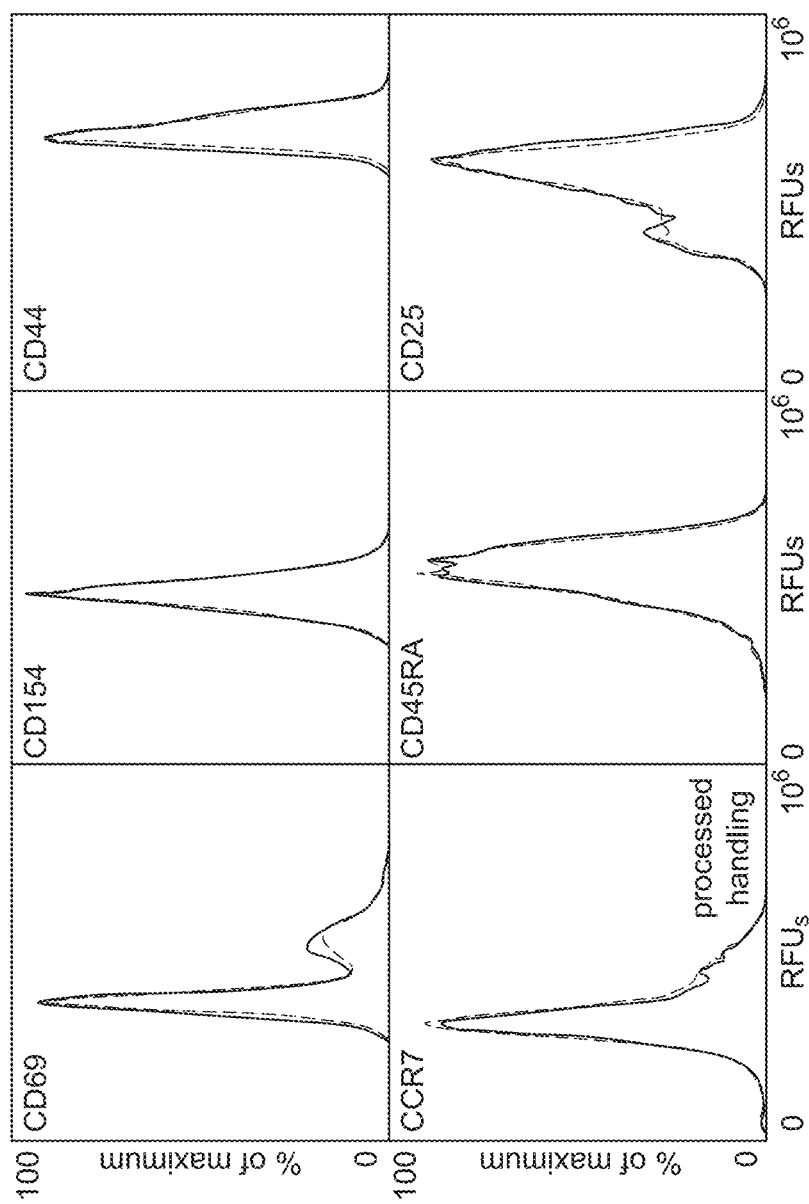
FIG. 5 is a graphical representation of a T-cell activation profile for CD69, CD154, CD44, CCR7, CD45RA and CD25.

Device processed cells and control cells showed the same expression for all markers (FIG. 5 shows representative data from a replicate from each group). Histogram data from both groups mapped almost identically, indicating that μVS does not alter the activation state of T cells 24 h after processing. This is advantageous as intracellular delivery with μVS results in high viability and recovery, but does not perturb the state of T cell activation in contradistinction to results seen using electroporation. FIG. 5 shows an overview of the T cell activation profile. After processing and 24 h of cell culture, each replicate from the handling control and processing control were individually labelled with fluorescent antibodies against markers of activation (CD69, CD154, CD44, CCR7, CD45RA and CD25) to assess if μVS exposure causes a change in T cell activation state. Replicates from each of the processed control cell and handling control cell group were plotted using FlowJo and the histogram data was overlaid. For all groups, the activation marker expression remained the same between control and device processed groups. Representative overlays of the flow cytometry data are plotted above with the processed control shown in dashed red and the handling control shown in blue. Based on the overlaid data, the activation state and activation/ naivety marker expression of pan T cells is not altered because of processing via μVS.

CONCLUSIONS: This example described the use of microfluidic post array used to create hydrodynamic conditions based on vortex shedding, or μVS, enabling the intracellular delivery of mRNA to human pan T cells. This method and device enabled the efficient delivery of mRNA to pan T cells with high cell recovery (e.g., 96.3±1.1%, mean±stdev), high cell viability (e.g., 83.7±0.7%) and meaningful EGFP expression (e.g., 57.4±6.8%) resulting in a yield of 46.3±5.6% recovered, viable, and EGFP expressing pan T cells when delivering mRNA at a concentration of 80 μg mL$^{-1}$ and at a processing rate of greater than 2 million cells s$^{-1}$. μVS is also shown to result in even EGFP expression profiles in the CD4$^+$ and CD8$^+$ T cell populations without changing the T cell activation state. Conveniently, the microfluidic devices may be fabricated with industry standard processes and relatively simple feature geometries allow for (1) high device yields that are thought to (2) readily scale.

Example 2

Hydrodynamic Plasmid Delivery

Figure 9:
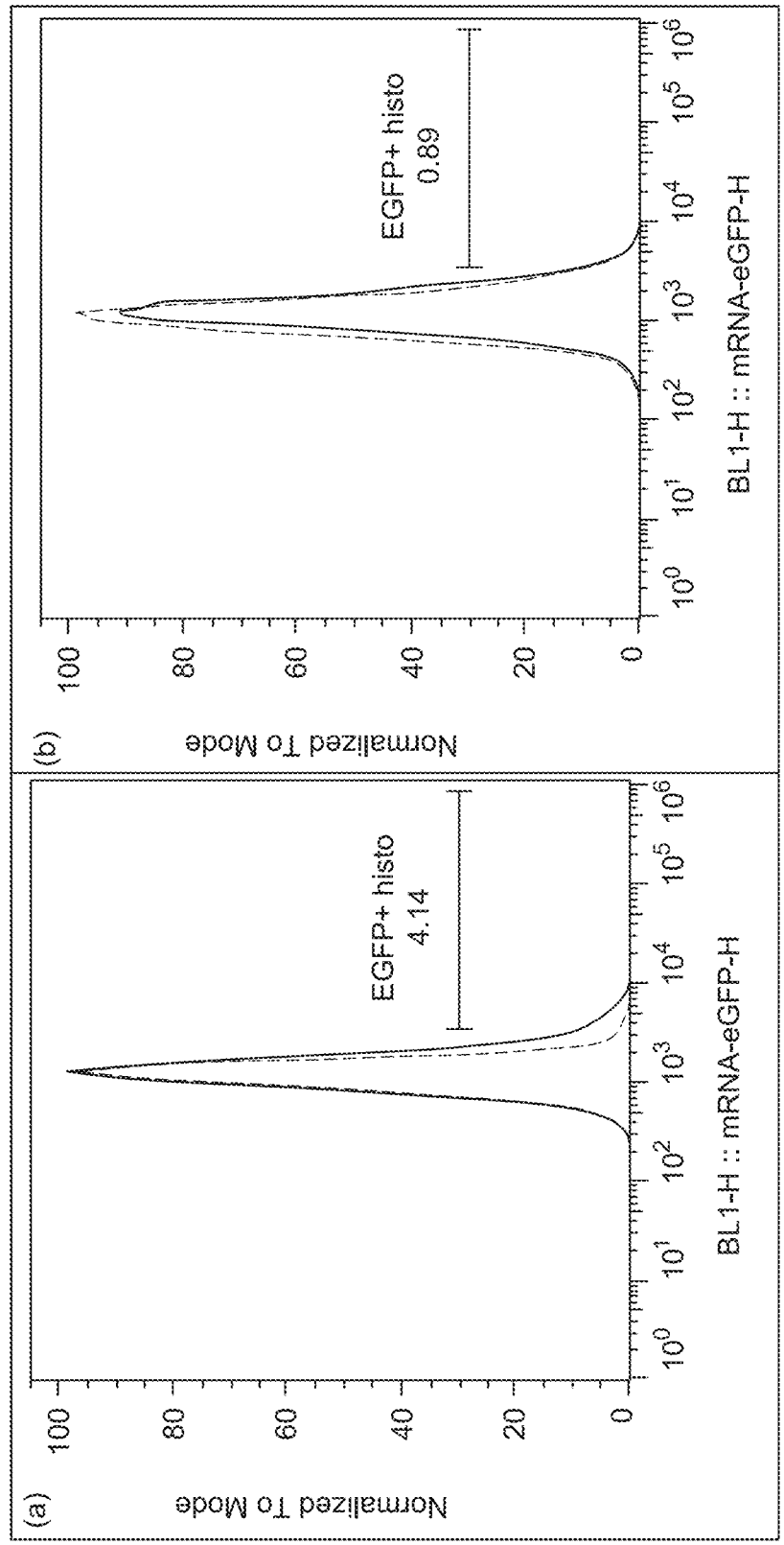
FIG. 9 is a graphical representation of EmGFP (emerald green fluorescent protein) plasmid expression after 5.7 kb plasmid delivery to human pan T cells using only µVS.

To assess the utility of intracellular delivery via hydrodynamic poration beyond just mRNA, the delivery of 5.7 kb DNA plasmids (pJTITM R4 Exp CMV EmGFP pA Vector, Thermofisher, A14146) using X-VIVOTM 20 media supplemented with 25 mM trehalose and 7.5% DMSO was looked at using the same protocols in Example 1 unless otherwise specified in this example. Pan T cells were activated once or twice prior to being re-suspended at a concentration of 16×10$^6$ cells ml-1 and mixed with EGFP plasmid at a concentration of 1.5 μg ml$^{-1}$ prior to being processed in the same devices described in Example 1 at an operating pressure of 120 psig. EGFP expression for the single-activated and double-activated cell populations was assessed between 43 hours after processing using industry standard flow cytometry techniques. As shown in FIG. 9a, 4.14% of activated, cultured for at least 7 days then processed cells followed by a second reactivation step were EGFP$^+$ and 0.75% of the single-activated pan T cells were EGFP$^+$ (see FIG. 9(b)). In effect, EmGFP (emerald green fluorescent protein) plasmid expression after 5.7 kb plasmid delivery to human pan T cells using only μVS. 4.14% EmGFP expression is achieved after activating, processing the human pan T cells with EmGFP plasmid using μVS followed by a post processing activation step, while 0.75% EGFP expression is achieve after single activation then processing of the pan T cells with μVS.

Cumulatively and relative to the mRNA data discussed in Example 1, this data shows that plasmid uptake is possible with μVS, however, expression levels are substantially lower than EGFP expression after mRNA delivery. This demonstrates a need for electrohydrodynamic intracellular delivery where an electric field coupled with hydrodynamic poration will enhance uptake and subsequent expression as seen when coupling, for example, cell squeezing with an electric field, along with when coupling electrosonic microjet ejection with an electric field.

Example 3

Optimization of Intracellular Delivery

Genetic modification via μVS is an optimal platform to support clinical and commercial manufacturing advancements and improvements for the production of GMCTs. Delivery efficiencies described in the examples above may be improved with electro-microfluidic vortex shedding (eμVS) using the different charged exogenous materials such as those described herein.

Figure 6:
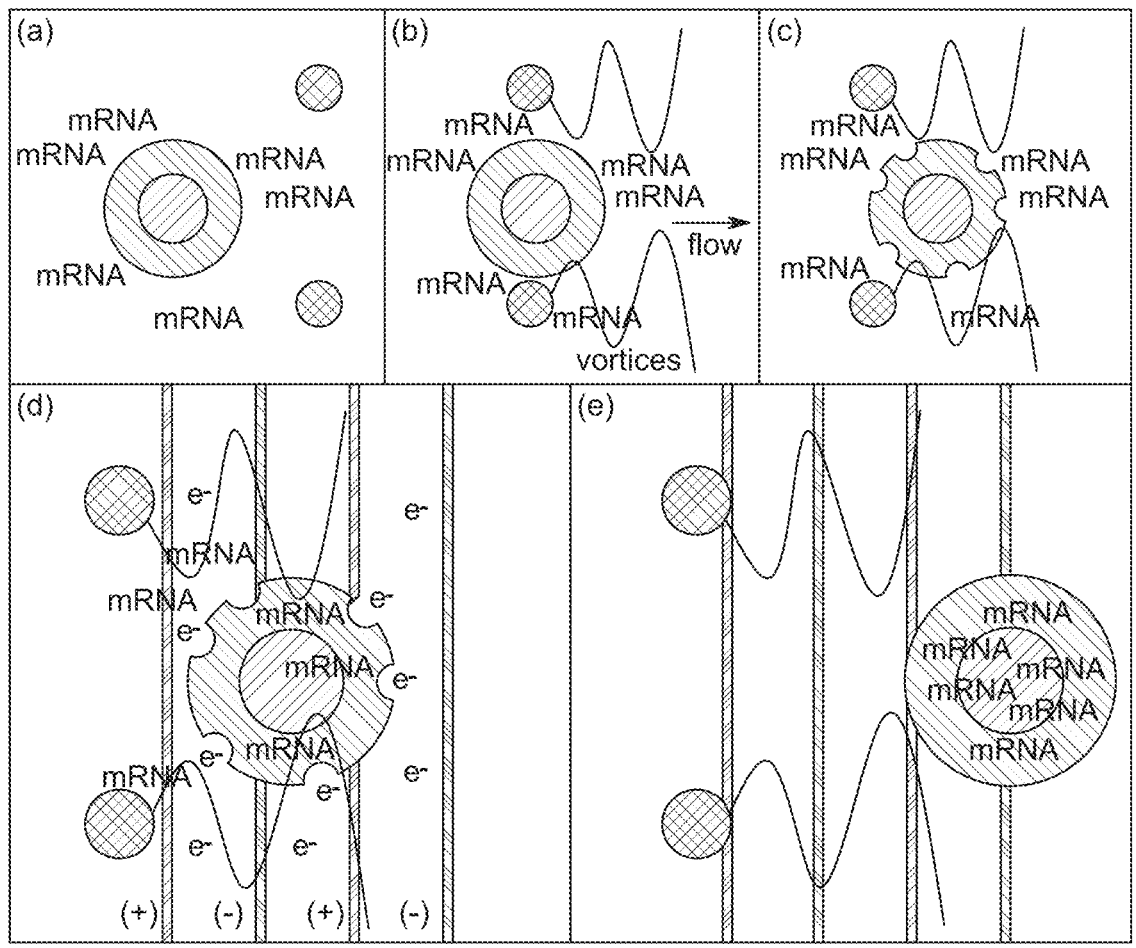
FIG. 6 is a schematic representation of an overview of electro-microfluidic vortex shedding (eµVS).

The delivery efficiency described above may be optimized through integration of interdigitated platinum electrodes for simultaneous or sequential (1) membrane permeabilization via μVS and (2) in situ active, electrophoretic delivery or intracellular delivery via electro-microfluidic vortex shedding (eμVS) as illustrated in FIG. 6. Platinum electrode integration may seek to determine if active (e.g., electrophoretic) transfer can enhance delivery efficiency of μVS without adversely affecting cell viability or perturbation of the cell state. eμVS may also be evaluated based on AC current at incremental DC offsets along with ±DC current. Additionally, eμVS may be coupled with cell selection (e.g., fluorescently activated cell sorting or FACS) to obtain high-purity genetically modified cell populations. FIG. 6 shows an overview of electro-microfluidic vortex shedding (eμVS) where (a) cell and mRNA or other exogenous materials are mixed in suspension, (b) flow of the suspension past posts creates vortices or unsteady flow, (c) vortices disrupt the cell membrane, (d) electric fields from interdigitated electrode then actively deliver mRNA or other exogenous materials into the cytosol prior to (e) the cell membrane recovering.

The hydrodynamic aspects of μVS have been developed such that the design geometry includes an approximately 4.8 mm×9.8 mm×1.4 mm (length×width×height or thickness) chip containing an approximately 7.5 mm×1 mm×0.04 mm deep reactive ion etched microfluidic flow cell with a single inlet and single outlet. The inlet and outlet are laser machined with an approximately 700-μm inner diameter. Within the flow cell is a post array consisting of 6 rows (flow-wise) and 17 columns of posts (flow-perpendicular) where the posts have a diameter of 40-μm and a 40-μm height that is equal to flow cell depth. Post rows have a 400-μm (flow-wise pitch) and post columns have a 60-μm (flow-perpendicular) pitch. A schematic of a typical μVS design geometry is shown FIG. 7. Specifically, FIG. 7 shows a schematic representation of a flow cell of one μVS design consisting of an approximately 4.8 mm×9.8 mm×1.4 mm (length×width×height or thickness) chip containing an approximately 7.5 mm×1 mm×0.04 mm deep reactive ion etched microfluidic flow cell with a single inlet and single outlet. The inlet and outlet are laser machined with an approximately 700-μm inner diameter. Within the flow cell is a post array consisting of 6 rows (flow-wise) and 17 columns of posts (flow-perpendicular) where the posts have a diameter of 40-μm and a 40-μm height that is equal to flow cell depth. Post rows have a 400-μm (flow-wise pitch) and post columns have a 60-μm (flow-perpendicular) pitch. The substrate also contains 8 thru holes for electrical access after bonding to the eμVS lid.

Figure 8:
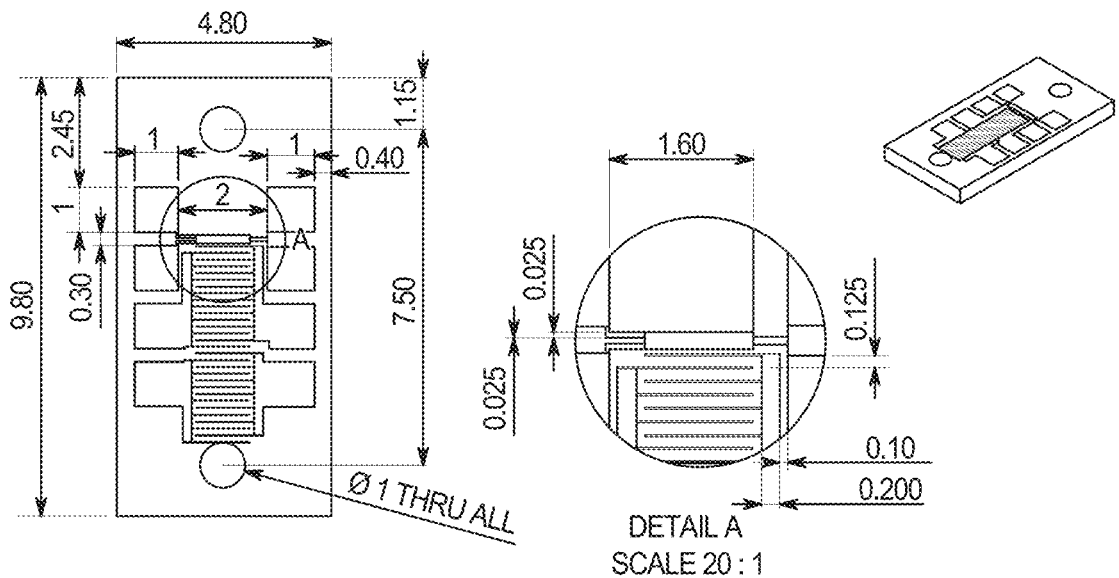
FIG. 8 is a schematic representation of an eµVS lid containing interdigitated platinum electrodes along with through holes for fluidic access.

In order to further optimize delivery efficiency, interdigitated platinum electrodes may be integrated into the quartz designs for in situ active, electrophoretic delivery or eμVS. This may be achieved through platinum electrode deposition via sputter coating and lift off on to a Borofloat substrate with laser machined inlet and outlet holes; and (3) anodic bonding of the lid (see FIG. 8) and flow cell substrates (see FIG. 7). Interdigitated platinum electrodes may span the entire flow cell (flow-perpendicular) with a 25-μm width (flow-wise) and a 150-μm pitch resulting in a 125-μm inter-electrode spacing. This helps ensure the ratio between electrode spacing and flow cell height is ~3.1 resulting in a uniform electric field between electrodes. An isolated array and outlet electrode arrays may be provided where each electrode array occupies an approximately 2-mm (flow-wise) region. Electrode arrays may be accessed through laser machined holes in the opposing substrate using micro pin probes or alternative conductive medium. Moreover, a thermocouple may also be integrated into the flow path to monitor changes in temperature. In particular, FIG. 8 shows a schematic representation of an eμVS lid containing interdigitated platinum electrodes along with through holes for fluidic access. This design is achieved through platinum electrode deposition via sputter coating and lift off on to a Borofloat substrate with laser machined inlet and outlet holes. Interdigitated platinum electrodes span the entire flow cell (flow-perpendicular) with a 25 μm width (flow-wise) and a 150 μm pitch resulting in a 125 μm inter-electrode spacing. There are also isolated arrays at the post array region and at the outlet region where each electrode array occupies an approximately 2 mm (flow-wise) region. Electrode arrays will be accessed through laser machined holes in the opposing substrate using micro pin probes or alternative conductive medium and the lid may be bonded to the flow cell substrate using anodic bonding, vacuum bonding or similar bonding technique.

Once fabricated, the electrodes may be characterized while flushed with transfection media (see Example 1) at room temperature (e.g., 20° C.) and at a representative volumetric flow rates (e.g., 1 ml s$^{-1}$) to measure (four-terminal) impedance between the electrodes and therefore measure the electric field strength (e.g., kV m$^{-1}$) for different applied peak-to-peak voltages (e.g., 1 to 10 Vpp). This may also be supplemented with changes in media composition or temperature. The maximum applied voltage may be determined by electrode degradation lifetime and alternating current may be used to minimize bubble formation at the electrodes. Estimated peak cell velocities within the design discussed above approach 15 to 50 m s$^{-1}$ resulting in a minimum 2.5 to 8.3-μs inter-electrode cell residence time—a 5 MHz AC sine wave may be used to ensure the sine wave period is significantly less (e.g., 12.5-fold) than the minimum and estimated inter-electrode cell residence time where lower frequencies may be used for lower peak cell velocities. It is envisioned that optimal μVS flow cell designs and electrode designs with vary with each specific cell type and optimal eμVS protocols may be needed for each specific exogenous material or agent.

Example 4 eμVS of mRNA to Resting PBMCs—Voltage Screen

To assess the utility of intracellular delivery via hydrodynamic poration in combination with a electrophoretic force, we looked at the delivery of mRNA to resting PBMCs using Resuspension Buffer T (ThermoFisher Cat no. MPK10096). Cells were pre-processed using the same protocols in Example 1 unless otherwise specified in this example. After filtering and counting, all cells were distributed to appropriate tubes in equal amounts to create the number of samples for the given experiment.

An external electric field force at a given voltage, frequency, DC-offset, and signal shape was configured on a benchtop function generator (Tektronix, AFG3011C) and linear power-supply (Pevono, PS305H 0-30V). The eμVS chip was connected in series to a 2200 Ohm current-limiting resistor, creating a voltage divider circuit for system monitoring of the electric field.

eμVS Experimental Rig Development: An experimental rig was developed to operate microfluidic devices. It can deliver between 0 and 150 psig and low- to high-voltages to the chip while fluid flows through the device. Platinum electrode pads on the chip were exposed to spring probes soldered on an external adapter with 8-electrical pin connections (McMaster Carr, 5949T62). A compressed nitrogen tank was regulated to deliver 140 PSI using a calibrated two-stage regulator. Volumetric flow rates were measured with a calibrated mass flow meter (Alicat Scientific, M-1SLPM-D). The samples were housed in a 1.5 mL Eppendorf tube and placed in a tube adaptor (Elveflow, KRXS) which was coupled to an in-house fixture with outlet tubing for sample collection as seen in FIG. 1(*a*). A 2-channel, digital storage oscilloscope (Tektronix, TBS1052B) is connected to monitor the input signal from the function generator and the output signal of the eμVS chip. The applied signal is sent to the interdigitated platinum electrodes which span the entire flow cell (flow-perpendicular) with a 25-μm width (flowise) and a 150-μm pitch resulting in a 125-μm inter-electrode spacing eμVS.

Electric Field Calibration & Characterization: Cells travel with a certain velocity, $v_{avg}$, within the eμVS device. The cells travel through an electric field, for a set amount of time, defined by the total distance of the electrode plates, $l_{e_{field}}$. The total time the cells spend in the electric field can be expressed by:

$$t_{e_{field}} = \frac{l_{e_{field}}}{v_{avg}}$$

The pulse duration of a signal applied to a bulk group of cells is related to the input frequency generated from the function generator:

$$T_{pulse} = \frac{1}{2\pi f}$$

where f is the input signal frequency in Hertz and $T_{pulse}$ is the single pulse duration delivered to the cells. The number of pulses the cells experience is related to the total time cells spend traveling across the electric field. It can be expressed as:

$$N_{pulses} = \frac{t_{efield}}{T_{pulse}}$$

As the cells and exogenous material travel through the eµVS chip, they experience an electric field force approximated by:

$$E_{field} = \frac{V_{applied}}{gap_{electrode}}$$

Where the applied voltage is the peak-to-peak voltage set by the function generator and the gap between the platinum electrode is designed and manufactured before testing is done. The success of the electrical delivery depends on the speed at which the cells pass through the electric field, (ii) the magnitude of this electric field, and (iii) the number of pulses the cell membranes experience. As the cells first experience physical deformation induced by the unsteady flow, cell membranes are slightly open and, traditionally, exogenous material diffuses into the cell. Instead, using eµVS, a low-voltage electrophoretic force aides the delivery of the exogenous material into the cell.

Peripheral Blood Mononuclear Cell (PBMC) Culture: Individual sample vials containing up to 50 million cryopreserved PBMCs were thawed and rested for a period of 1 day (16-32 h). For the experiments, resting PBMCs were transfected at 1 day (16-32 h) from the initial culture time.

PBMC sample preparation and processing: Immediately before transfection, 80 µL of eGFP mRNA (1 µg/µL TriLink Biotech PN L-6301-1000) was added to each sample to be transfected at a mRNA concentration of 200 µg/mL (1 to 5 ratio). The mRNA and cell samples at concentrations ranging from 5.0-7.0×106 cell/mL were mixed with pipetting. Cells were then processed through the experimental jig at varying pressures using nitrogen gas, varying electrical conditions, and captured in 15 mL falcon tubes containing XVIVO 10 or 15 preheated to 37° C. Flow rates and other experimental run details are recorded prior to delivery of mRNA to PBMCs.

Figure 10:
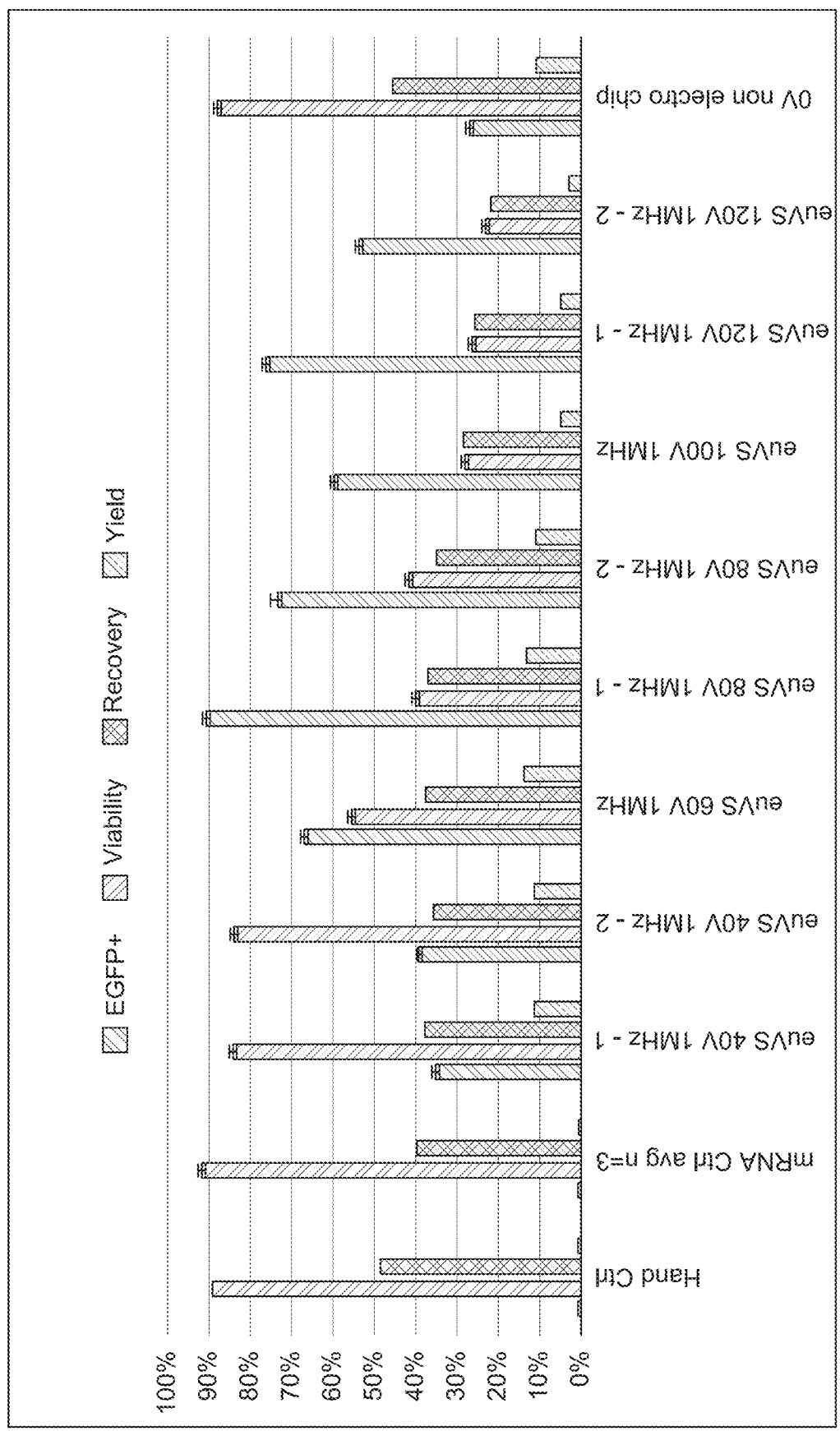
FIG. 10 is a graphical representation of EGFP expression, cell viability, yield, and recovery after EGFP mRNA delivery to resting PBMCs after µVS and eµVS processing at 21 hours.

EGFP mRNA Delivery to Resting PBMCs at Different Concentrations & Electrical Conditions: eµVS applies an electrical field to bulk cells in motion which reduces processing time and impact on T cell health. Over multiple experiments, delivery of 200 µg/mL mRNA to PBMCs resulted in EGFP expression ranging from approximately 28.9% to 91.1% of the live, processed cell population at 21 h (FIG. 10). This expression range corresponds to a delivery yield range of 2.73% to 16.31%, which represents a 0% to 34.35% enhancement relative to µVS. eµVS typically has a higher delivery efficiency and a slightly lower or equivalent cell viability (e.g., greater than 75%) at certain electrical conditions. Potential stress or damage can occur when cells are in low to serum free medium or in high voltage environments, for long periods of time. Like µVS, eµVS has a short processing time that allows for cells to be returned to cell culture medium shortly after processing. Thus, the low-voltage, electrophoretic force leads to an increase in efficiency compared to standard µVS without causing excessive stress and damage to the cells.

Considerations for optimizing eµVS include selecting appropriate electrical characteristics (e.g., voltage, frequency, DC-offset, signal type) and biological conditions (e.g., culture media, processing media, concentration of cells, exogenous material, and cell type, among others). Considerations also include optimizing the design of post-arrays as well as the configuration of the interdigitated platinum electrodes. These variables together may also have an impact on the overall ease of pore generation and cell recovery with eµVS. A trend of decreasing viability, similar to the viability percentages commonly seen when using electroporation to deliver mRNA to PBMCs, occurs after 60V at a frequency of 1 MHz with a 0V DC-offset for the first version of the eµVS chip design. This is equivalent to an estimated electric field force above 3.2 kV/cm applied to the cells, demonstrating the threshold voltage for which the applied electric field seems to kill the cells in the fluid flow. A variety of electrical conditions were set using the above mentioned equipment; it was found that a 40V, 1 MHz sine wave with a DC-offset of 10 V had a recovery, viability, and delivery efficiency of mRNA to resting PBMCs of 52%, 79.4%, and 38.1%, respectively. These results demonstrate that the addition of an electric field improves standard µVS yield by approximately 30%. Different processing media compositions, for example some that are more conductive or complementary to the combinatorial effect of eµVS, may improve these results.

The decrease in viability of all groups processed using eµVS compared to the handling control may be due to increased cell death upon return to culture due to unsuccessful membrane repair attempts, bulk mechanical lysis, ohmic heating as a result of the applied electric field, and medium stress.

Figure 11:
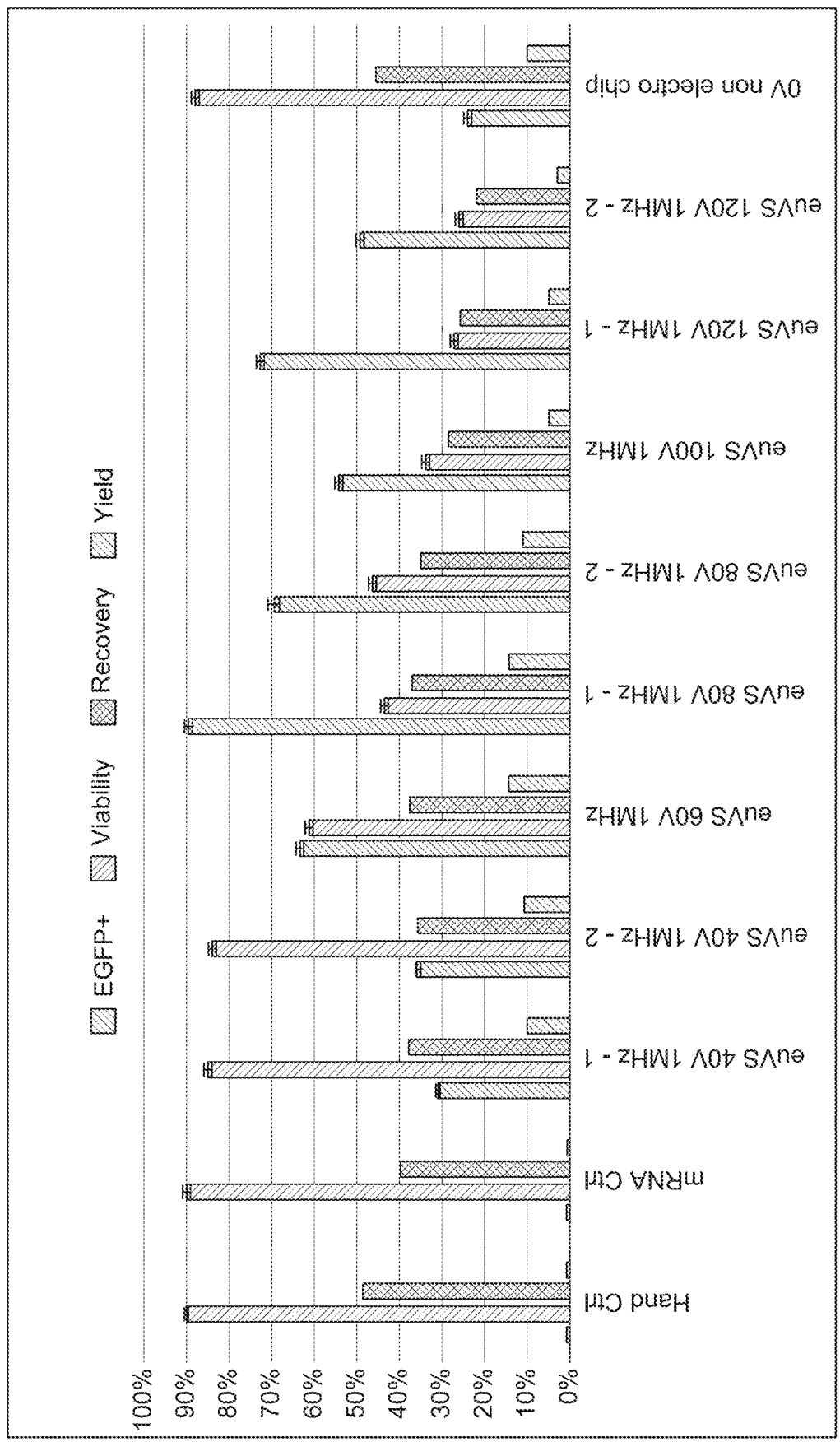
FIG. 11 is a graphical representation of EGFP expression, cell viability, yield, and recovery after EGFP mRNA delivery to resting PBMCs after µVS and eµVS processing at 42.5 hours.

Cumulative and relative to the mRNA data discussed in Example 1, this data shows that delivery enhancement of mRNA is possible with eµVS. Cell viabilities are preserved and delivery of exogenous material is enhanced relative to µVS (FIGS. 10 and 11). FIGS. 10 and 11 show EGFP expression, cell viability, yield, and recovery after EGFP mRNA delivery to resting PBMCs after µVS and eµVS processing (1) at 21 h and (2) at 42.5 h. EGFP expression (e) and viability (v) were measured and number of cells recovered (r) after processing were calculated. These three measures were then used to calculate yield (y) of live, EGFP expressing cells using the formula y=evr. Enhanced delivery of mRNA to resting PBMCs using eµVS was observed at different electrical conditions when compared to µVS. In addition, a reduction in cell viability was observed at increasing voltage levels above 60V at a frequency of 1 MHz with a 0V DC-offset, which led to a decrease in yield.

Figure 12:
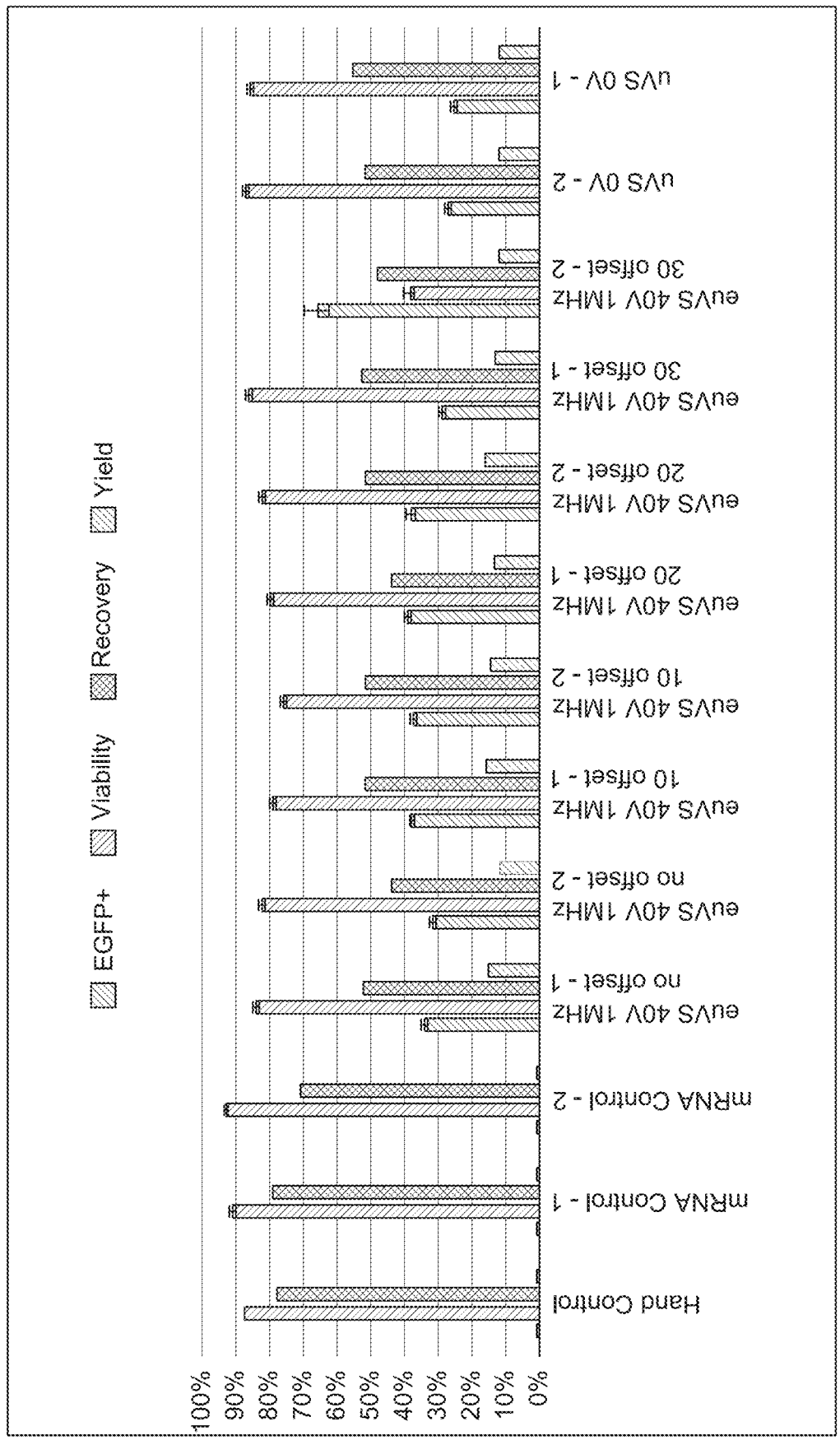
FIG. 12 is a graphical representation of EGFP expression, cell viability, yield, and recovery after EGFP mRNA delivery to resting PBMCs after eµVS processing at 20 hours.
Figure 13:
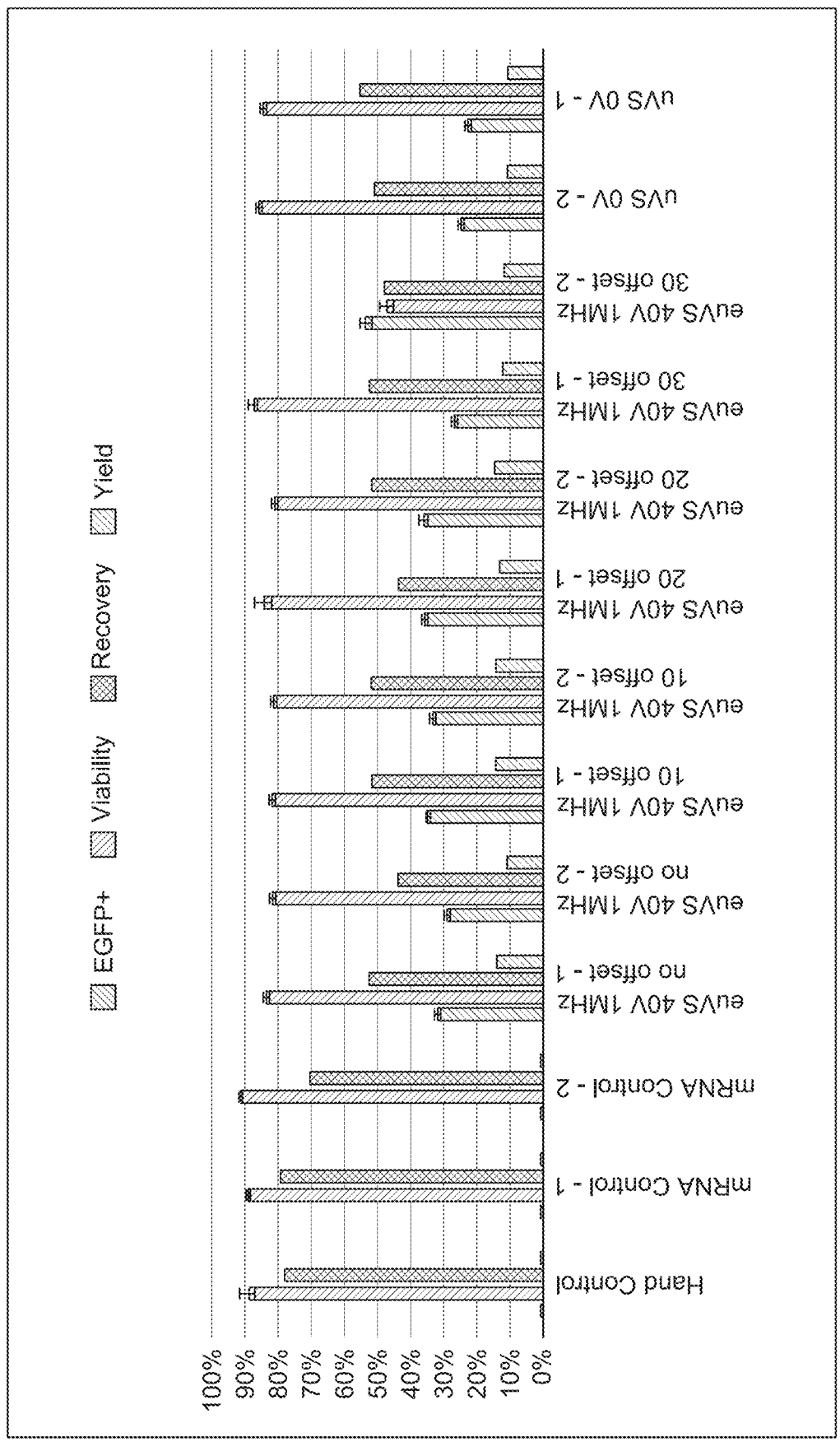
FIG. 13 is a graphical representation of EGFP expression, cell viability, yield, and recovery after EGFP mRNA delivery to resting PBMCs after eµVS processing at 43 hours.

FIGS. 12 and 13 shows graphical representations of EGFP expression, cell viability, yield, and recovery after EGFP mRNA delivery to resting PBMCs after eµVS processing at 20 hours (FIG. 12) and 43 hours (FIG. 13) at varying electrical conditions and DC-offsets ranging from 0V to 30V. EGFP expression (e) and viability (v) were measured and number of cells recovered (r) after processing were calculated. These three measures were then used to calculate yield (y) of live, EGFP expressing cells using the formula y=evr. Enhanced delivery of mRNA to resting PBMCs using eμVS was observed at different electrical conditions compared to μVS yet a reduction in cell viability was observed at increasing voltage levels above 40V at a frequency of 1 MHz with a 30V DC-offset which led to a decrease in yield. The low-frequency, DC-offset.

No Change in T Cell Activation: As mentioned in [0181], electroporation of primary immune cells increases activation markers in T cells. It is therefore important to examine the impact of eμVS on T cell activation (FIGS. 14-17). To assess the impact of μVS-based mRNA delivery on T cell activation, handling control cells, handling control cells activated overnight with CD3/CD28 Dynabeads, mRNA control cells, and device processed cells were labelled with fluorescently labelled antibodies against various activation markers 24 h-48 h (as indicated) after return to culture. One sample from each replicate in the controls and device processed groups were removed from culture and diluted in a 96-well plate with DPBS. The cells were pelleted by centrifugation (2 min 800×g), supernatant removed by aspiration, and re-suspended in FACS buffer containing 25 μL mL−1 of one of the following ThermoFisher monoclonal antibodies per sample: CD8a-PE (12-0088-42), CD45RA-PerCP-Cy5.5 (45-0458-42), CD45RO-PE-Cy7 (25-0457-42), CD137-Alexafluor 647 (A51019), CD3-AF700 (56-0037-42), CD4-APC-eF780(56-0037-42), CD69-eFluor450 (48-0699-42), Live Dead Aqua Stain (#), CD62L-Super Bright 600 (63-0629-42), CD25-Brilliant Violet 711 (302636). The samples were incubated on ice for 30 minutes, rinsed twice with FACS buffer, and analyzed via flow cytometry. Expression of markers of activation CD69, CD25, CD137, as well other markers downregulated upon activation CD45RA and CD62L, were looked at. CD25 is a late marker of activation compared to CD69, which increases upon cell activation and persists on an activated cell's surface longer than CD69. CD45RA is found on naïve T cells (Tn) and is lost upon activation and formation of memory (Tn=CD45+, CD62L+). CD45RO is a marker commonly found on memory cells, Tcm (Tcm=CD45−, CD62L+). CD62L is commonly downregulated upon activation. A shift in the histogram shape, population distribution, or change in fluorescence intensity for the device processed cells compared to that of the handling control would demonstrate that eμVS exposure impacts T cell activation state of eμVS processed cells. After the experiment, cells were returned to culture medium with IL-2 for 24 h-48 h to recover and allow time for activation marker expression or alteration of activation state. Isotype control for mouse IgG1 kappa was previously determined to have no off target or non-specific binding interactions with the T cells (not shown). Thus, shifts in fluorescence intensity for the various markers were due to specific interactions.

Figure 14B:
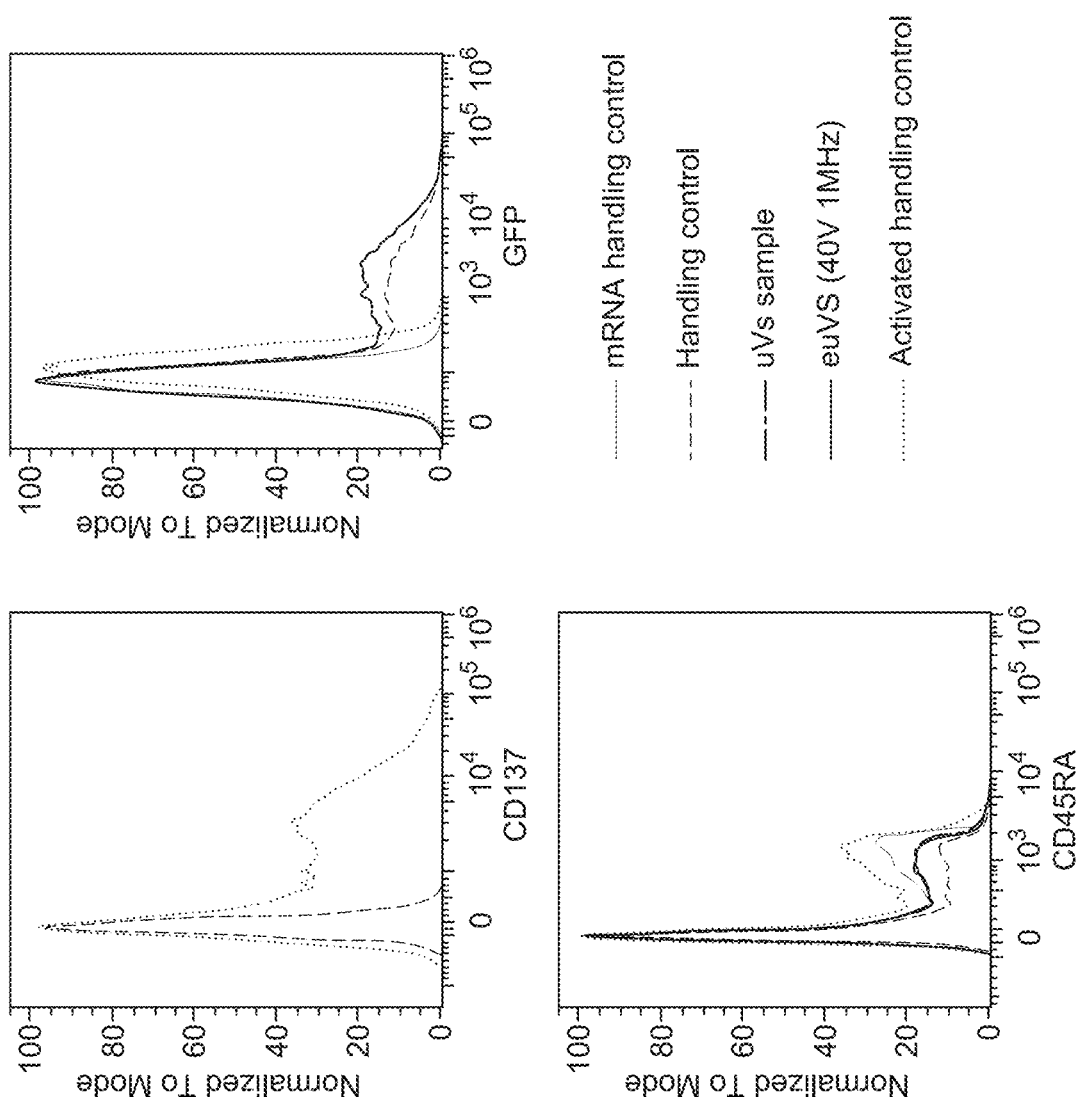
Figure 15B:
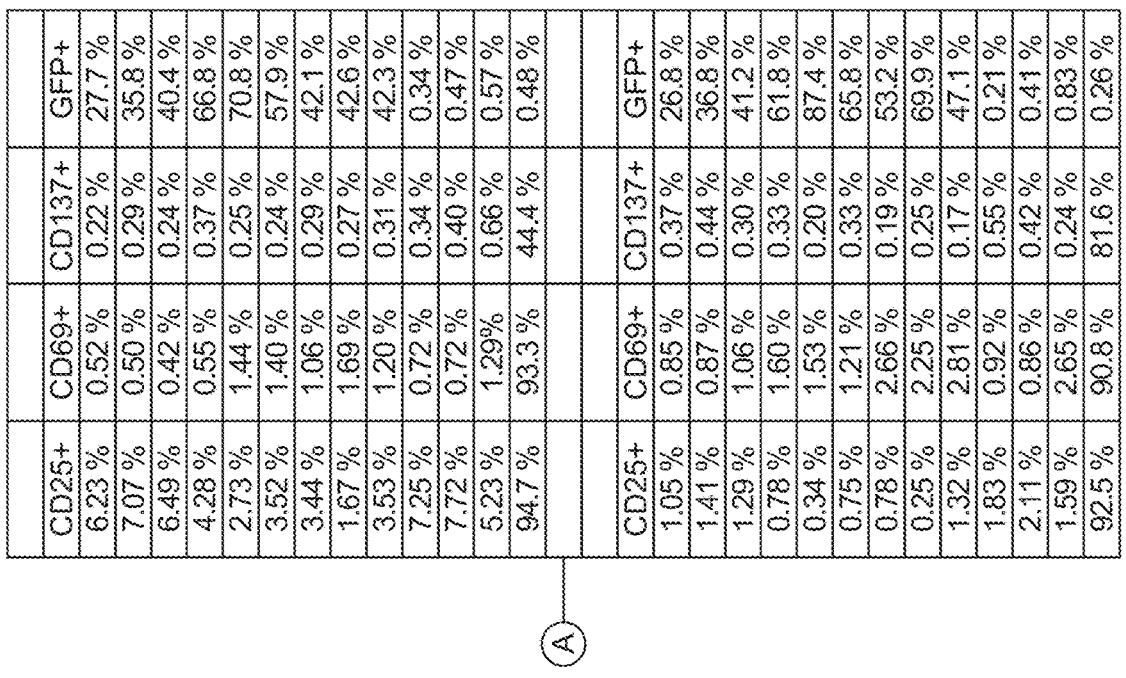
Figure 16A:
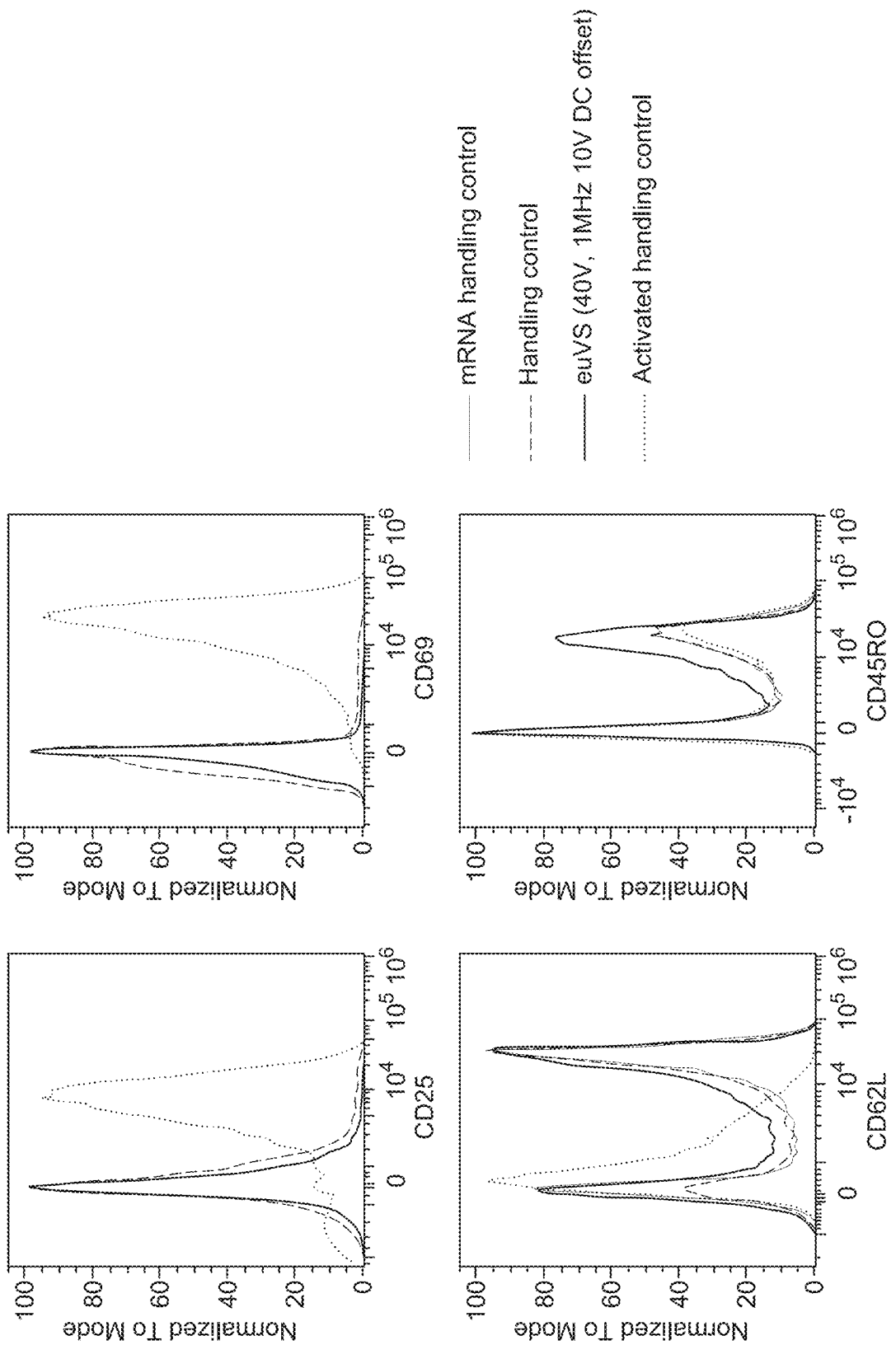
FIGS. 16A and 16B are graphical representations of representative histograms showing surface marker expression of eµVS processed samples of resting PBMCs at 24 hours after processing.
Figure 16B:
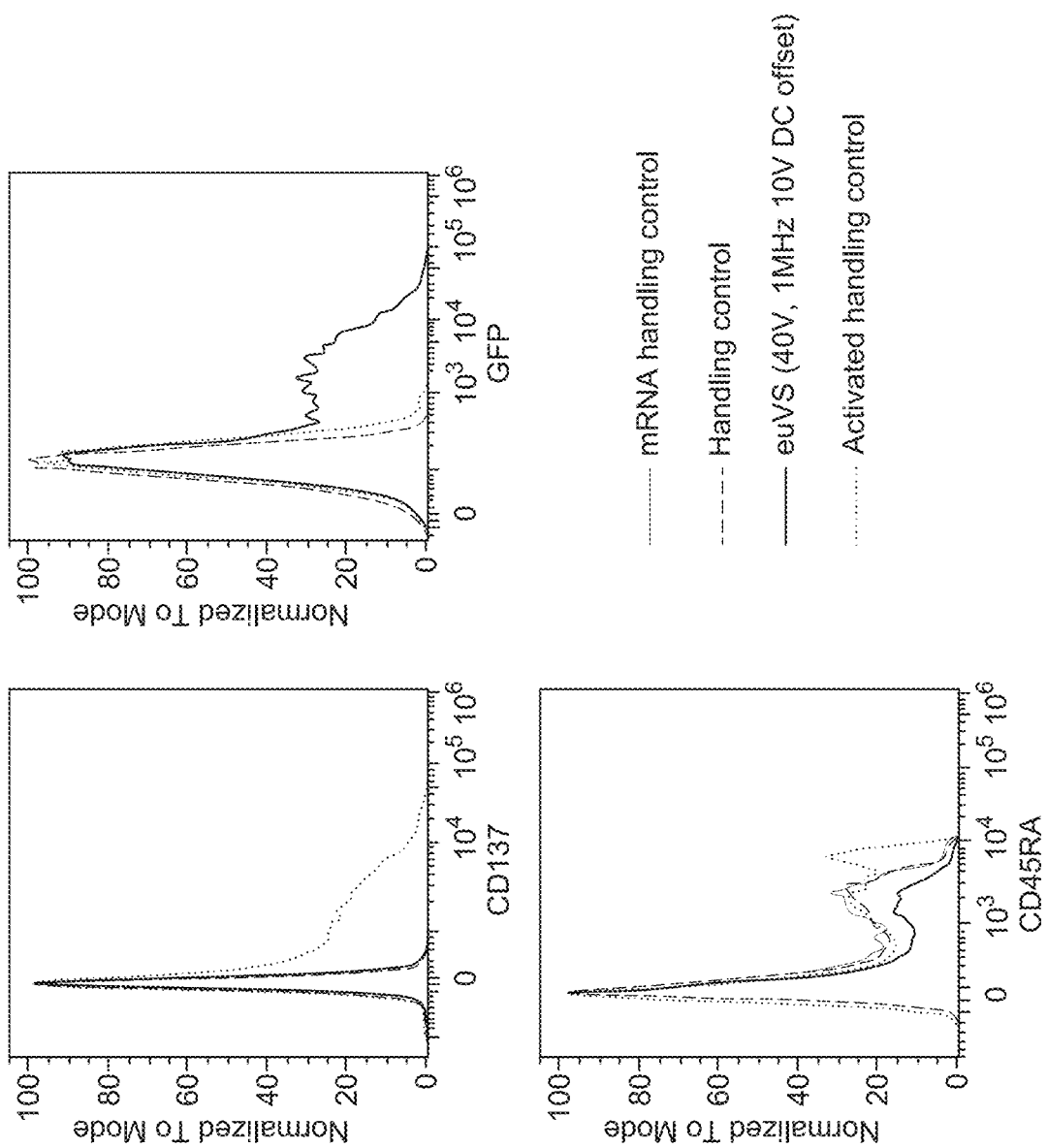
Figure 18:
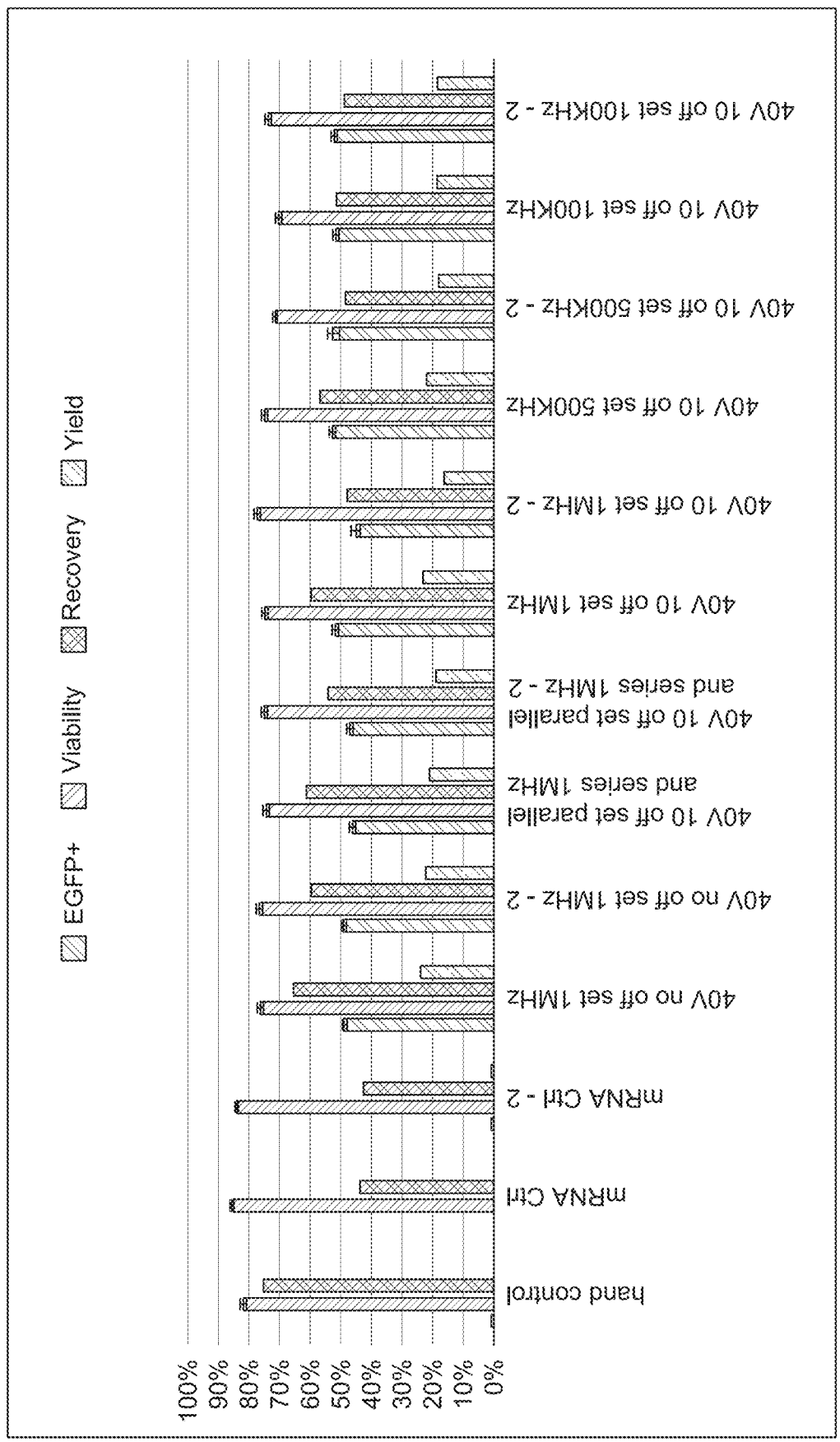
FIG. 18 is a graphical representation of EGFP expression, cell viability, yield, and recovery after EGFP mRNA delivery to overnight activated PBMCs using eµVS collected after 19.5-20 hours of transfection.
Figure 19:
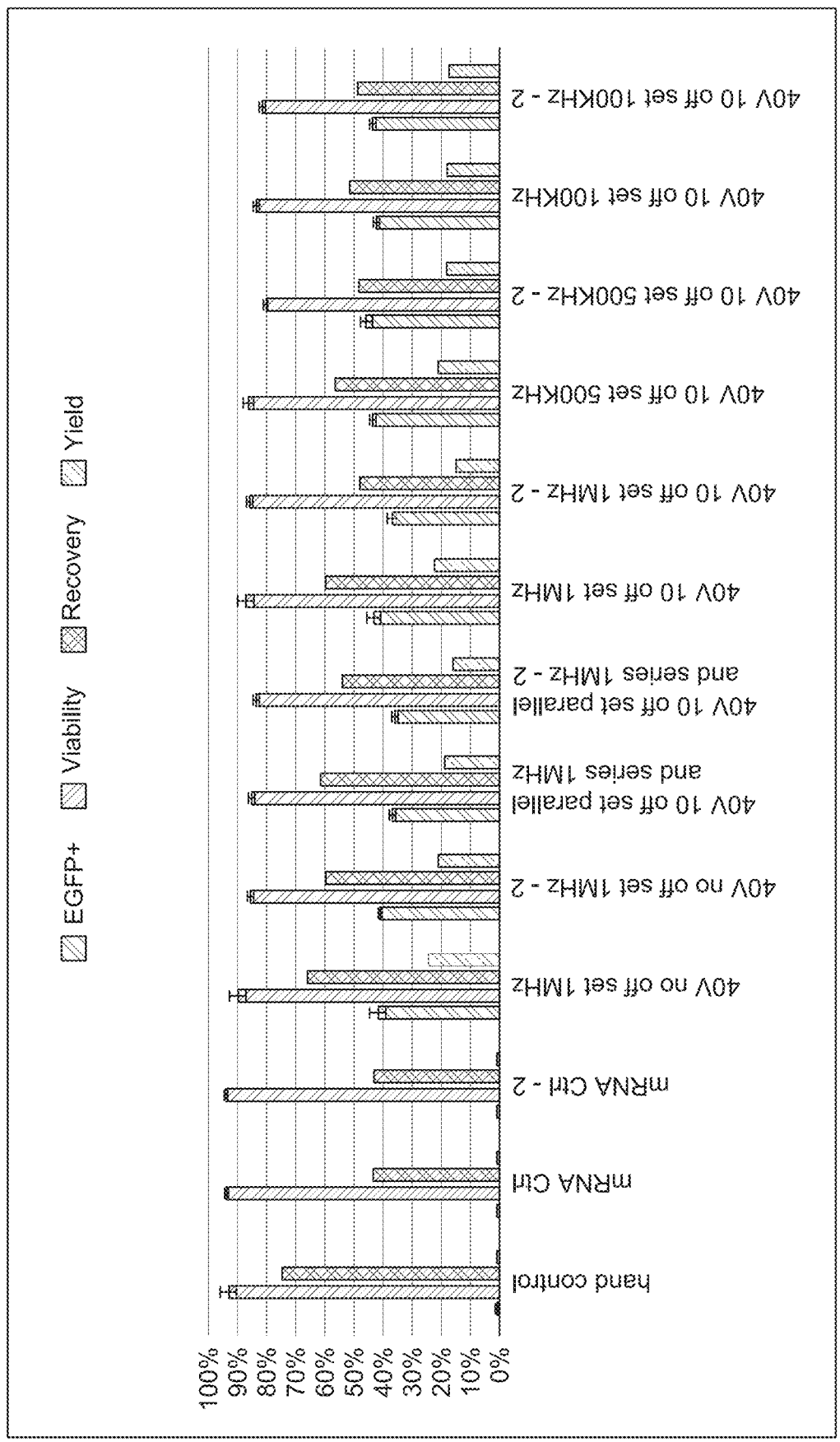
FIG. 19 is a graphical representation of EGFP expression, cell viability, yield, and recovery after EGFP mRNA delivery to overnight activated PBMCs using eµVS collected after 47.5 hours of transfection.

Device processed cells and control cells showed no change in activation marker expression for CD25, CD69, and CD137 compared to handling control or mRNA control in either μVS or eμVS treated samples (FIGS. 14-17 show representative data from a replicate from each group). No major changes in T cell subtype populations were seen. Histograms from both groups indicate that eμVS does not alter the activation state of T cells 24 h-48 h after processing. This is advantageous as intracellular delivery with eμVS results in higher efficiencies than μVS, but does not perturb the state of T cell activation. Specifically, FIG. 14 shows a graphical representation of representative histograms showing surface marker expression of μVS and eμVS processed samples of resting PBMCs at 48 hours after processing. CD25, CD69 and CD137 are markers normally seen on activated T cells, while CD62L is downregulated upon activation. CD45RO and CD45RA markers represent T cell subtypes of memory and naïve cells, respectively. EGFP expression was also plotted. Lines of progressively darker shades of gray represent mRNA handling control (lightest gray) and handling control (middle gray) which serve as negative controls. μVS sample is darkest gray while solid black line represents a eμVS (40V 1 MHz) sample. Dotted black lines correspond to activated handling control samples, which were activated by CD3/28 dynabeads overnight to serve as a positive control for T cell activation profile. No upregulation of activation marker expression or change in T cell subset phenotype was observed in either μVS or eμVS processed cells. FIG. 15 shows a representation of expression profiles of various activation or T cell lineage surface markers in CD3+ cells divided into CD4+ and CD8+ populations in resting PBMCs processed using μVS or eμVS at 48 hours. FIG. 16 shows a graphical representation of representative histograms showing surface marker expression of eμVS processed samples of resting PBMCs at 24 hours after processing. CD25, CD69 and CD137 are markers normally seen on activated T cells, while CD62L is downregulated upon activation. CD45RO and CD45RA markers represent T cell subtypes of memory and naïve cells, respectively. EGFP expression was also plotted. mRNA handling control (lightest gray) and handling control (dark gray) serve as negative controls. Solid black line represents eμVS (40V, 1 MHZ 10V offset) sample. Dotted black lines correspond to activated handling control samples, which were activated by CD3/28 dynabeads overnight to serve as a positive control for T cell activation profile. No upregulation of activation marker expression or change in T cell subset phenotype was observed in eμVS processed cells. FIG. 17 is a representation of expression profiles of various activation or T cell lineage surface markers in CD3+ cells divided into CD4+ and CD8+ populations in resting PBMCs processed using eμVS at 24 hours after processing. FIGS. 18 and 19 show EGFP expression, cell viability, yield, and recovery after EGFP mRNA delivery to overnight activated PBMCs using eμVS collected after 19.5-20 hours of transfection (FIG. 18) and after 47.5 hr (FIG. 19). These graphs illustrate the results of samples for different electrical conditions and demonstrates the effective enhancement of delivery without harming the cells and thus lowering overall cell viability.

The example set forth above describes the combinatorial use of microfluidic post arrays to create unsteady, hydrodynamic conditions, otherwise known as μVS, and a low-voltage electrophoretic force to enable the intracellular delivery of mRNA to resting and activated PBMCs, (eμVS). The method and device described in this example enabled the efficient delivery of mRNA to resting PBMCs with high recovery (52%), viability (82.4%), and increased efficiencies (38.1%) at an mRNA concentration of 200 μg mL−1. eμVS results in little to no T cell activation state change as seen by surface marker expression in both resting and activated PBMCs. The devices may be fabricated using industry standard processes and simple feature geometries, enabling (1) high device yields and (2) devices that are readily scalable for production.

Example 5

Activated PBMCs

Peripheral Blood Mononuclear Cell (PBMC) Culture: Individual sample vials containing up to 50 million cryopreserved PBMCs were thawed and allowed to recover and rest in culture for less than an hour. The PBMCs were then activated using Dynabeads Human T—Activator CD3/28 (ThermoFisher Cat No. 111.31D) within 1 hour of being placed in culture. For development experiments, activated PBMCs were transfected at 1 day (16-32 h) from the activation time.

Overnight activated PBMC preparation and processing: PBMCs were activated for 18.5 h and the Dynabeads were removed prior to cells being resuspended at a concentration of 3.4×106 cells ml$^{-1}$. Immediately before transfection, the samples were mixed with 80 µL of mRNA (1 µg/µL TriLink Biotech PN L-6301-1000) at a concentration of 1 µg/µL. The mRNA concentration of the total sample was 200 µg/mL which is a 1 to 5 ratio. Cells were then handled, transfected, processed, and cultured similarly to the resting PBMCs, detailed in section(s) [Example 4]. The pre-activated handling control was split into two groups during post-processing cell culture. One of the groups received an additional activation with Dynabeads Human T—Activator CD3/28.

Figure 20A:
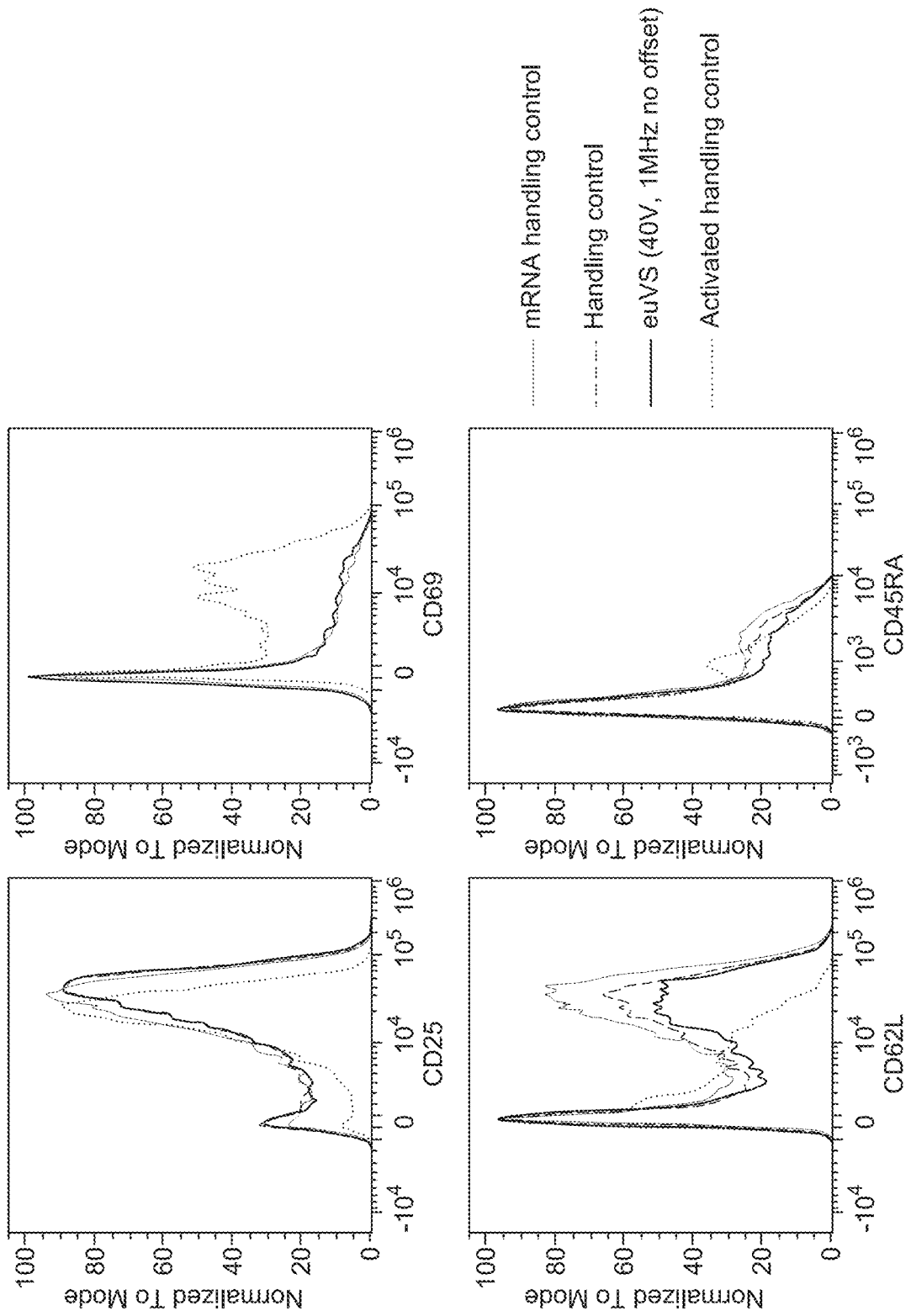
FIGS. 20A and 20B are graphics representations of representative histograms showing surface marker expression of eµVS processed samples of activated PBMCs at 24 hours after processing.
Figure 20B:
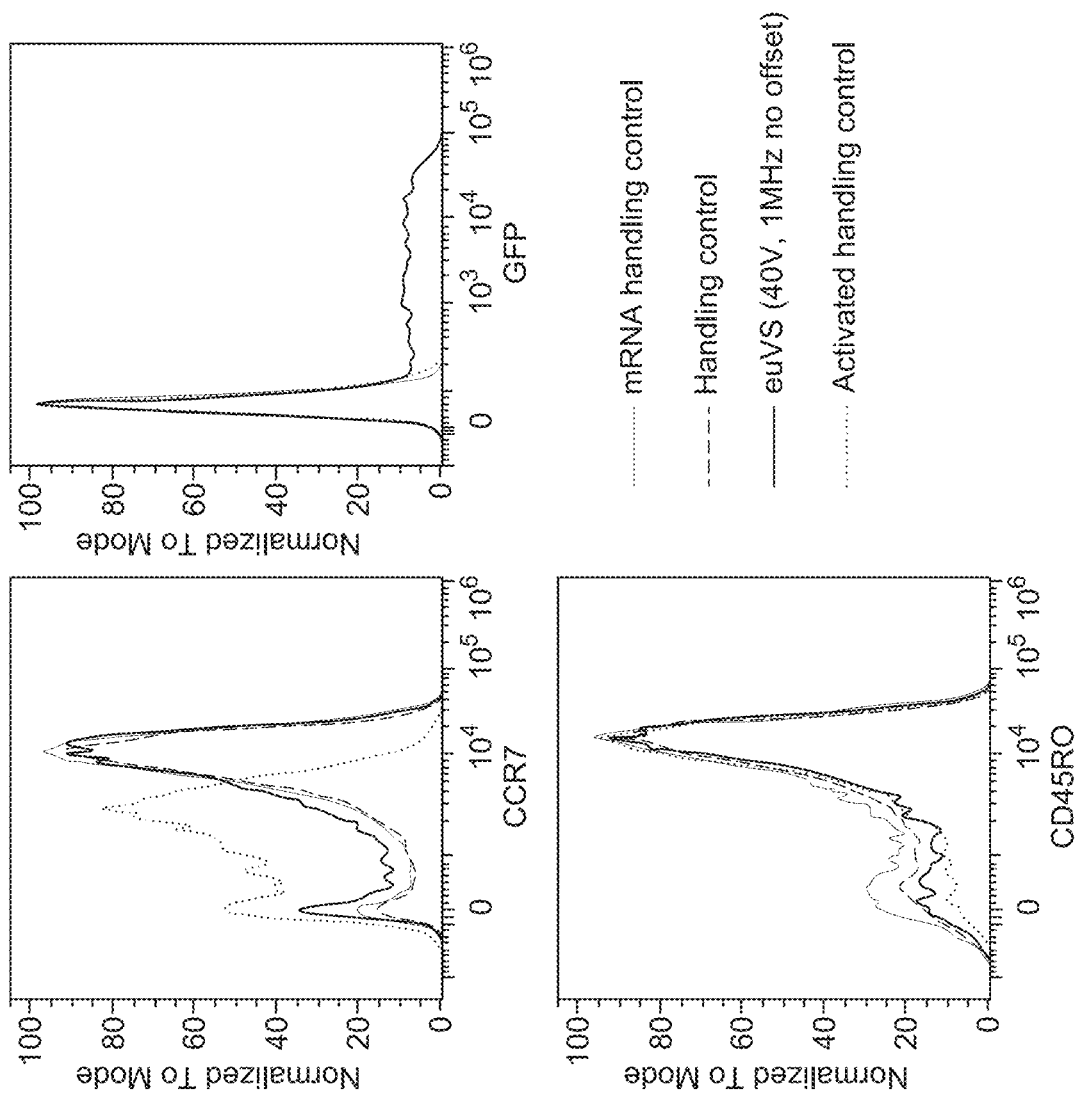

Expression and Phenotype of Activated PBMCs transfected with the eµVS method: An EGFP expression time point taken at 19.5 h of the processed overnight activated T cells using eµVS techniques, resulted in an optimal EGFP delivery, viability, recovery, and yield of 48.8%, 76.2%, 65.8%, and 24.51%, respectively (FIG. 18). The optimal electrical configuration was 40 V with 0 V DC-offset with a 1 MHz input frequency. Methods for activation phenotyping were same as described above for resting PBMCs, except a different activation panel was used: CD8a-PE (12-0088-42), CD45RA-PerCP-Cy5.5(45-0458-42), CD45RO-PE-Cy7 (25-0457-42), CD197-CCR7-Alexafluor 647 (353218), CD3-AF700 (56-0037-42), CD4-APC-eF780(56-0037-42), CD69-eFluor450 (48-0699-42), Live Dead Aqua Stain (#), CD62L-Super Bright 600 (63-0629-42), CD25-Brilliant Violet 711 (302636). Similar to the T cell activation profile of resting PBMCS transfected with µVS, the eµVS method to deliver mRNA to activated PBMCs also saw no significant change in the activation phenotype profile when compared to the activated post experiment handling control cells (FIGS. 20 and 21). FIG. 20 shows a graphical representation of representative histograms showing surface marker expression of eµVS processed samples of activated PBMCs at 24 hours after processing. CD25, CD69 and CD137 are markers normally seen on activated T cells, while CD62L is downregulated upon activation. CD45RO and CD45RA markers represent T cell subtypes of memory and naïve cells, respectively. EGFP expression was also plotted. mRNA handling control (lightest gray) and handling control (dark gray) serve as negative controls. Solid black line represents eµVS (40V, 1 MHZ no offset) sample. Dotted black lines correspond to activated handling control samples, which were activated by CD3/28 dynabeads overnight to serve as a positive control for T cell activation profile. No upregulation of activation marker expression or change in T cell subset phenotype was observed in eµVS processed cells. On the other hand, FIG. 21 shows expression profiles of various activation or T cell lineage surface markers in CD3+ cells divided into CD4+ and CD8+ populations in overnight activated PBMCs processed using eµVS after 24 hours.

The disclosure of every patent, patent application, computer program, algorithm, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the present disclosure without limiting the present disclosure to any one embodiment or specific collection of features. Those of skill in the art will therefore appreciate that, in light of the instant disclosure, various modifications and changes can be made in the particular embodiments exemplified without departing from the scope of the present disclosure. All such modifications and changes are intended to be included within the scope of the appended claims.

What is claimed is:

1. A method for introducing exogenous material into a cell, comprising:
    exposing the cell in suspension with the exogenous material to a pressure change under unsteady flow conditions to temporarily permeabilise a cell membrane without the cell becoming lysed; and
    exposing the cell to an electrical field to introduce the exogenous material into the cell while the membrane is permeabilised, the electric field being generated at an electric field strength insufficient to adversely perturb the cell state.

2. The method of claim 1, wherein the exogenous material is introduced into the cell through electro-microfluidic vortex shedding.

3. The method of claim 1, wherein the exogenous material is negatively charged.

4. The method of claim 1, wherein the exogenous material is positively charged.

5. The method of claim 1, wherein the exposure of the cell to the electric field occurs while the cell is in the unsteady flow.

6. The method of claim 1, wherein the electric field is generated using a direct current.

7. The method of claim 1, wherein the electric field is generated using an alternating current.

8. The method of claim 1, wherein the electric field includes an oscillating component and an offset sufficient to facilitate delivery of exogenous material.

9. The method of claim 1, wherein the exogenous material is selected from the group consisting of an organic molecule, a physiologically acceptable organic molecule derivative, a biomolecule, a physiologically acceptable biomolecule derivative, a physiologically acceptable biomolecule analogue, an inorganic molecule, a physiologically acceptable inorganic molecule derivative, a quantum dot, a carbon nanotube, a nanoparticle, and a gold particle.

10. A method for introducing exogenous material into a cell, comprising:
    exposing the cell in suspension with the exogenous material to a pressure change under unsteady flow conditions to temporarily permeabilise a cell membrane without the cell becoming lysed; and
    exposing the cell to an electrical field to introduce the exogenous material into the cell while the membrane is permeabilized, the electric field including an oscillating component and an offset insufficient to adversely perturb the cell state.

11. A method for introducing exogenous material into a cell, comprising:
- exposing the cell in suspension with the exogenous material to a pressure change under unsteady flow conditions to temporarily permeabilise a cell membrane without the cell becoming lysed; and
- exposing the cell to an electrical field to introduce the exogenous material into the cell while the membrane is permeabilized, the electric field being generated at a frequency insufficient to adversely perturb the cell state.

* * * * *